United States Patent
Kulikowski et al.

(10) Patent No.: US 10,772,894 B2
(45) Date of Patent: *Sep. 15, 2020

(54) COMPOSITIONS AND THERAPEUTIC METHODS FOR THE TREATMENT OF COMPLEMENT-ASSOCIATED DISEASES

(71) Applicant: Resverlogix Corp., Calgary (CA)

(72) Inventors: Ewelina B. Kulikowski, Calgary (CA); Dean E. Gilham, Calgary (CA); Sylwia Wasiak, Calgary (CA); Christopher R. A. Halliday, Calgary (CA); Henrik C. Hansen, Calgary (CA)

(73) Assignee: Resverlogix Corp., Calgary, Alberta (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/142,969

(22) Filed: Sep. 26, 2018

(65) Prior Publication Data

US 2019/0091235 A1 Mar. 28, 2019

Related U.S. Application Data

(63) Continuation of application No. 15/066,513, filed on Mar. 10, 2016, now Pat. No. 10,111,885.

(60) Provisional application No. 62/132,572, filed on Mar. 13, 2015, provisional application No. 62/264,768, filed on Dec. 8, 2015.

(51) Int. Cl.
| | |
|---|---|
| *A61K 31/551* | (2006.01) |
| *A61K 31/517* | (2006.01) |
| *C07D 403/04* | (2006.01) |
| *C07D 239/91* | (2006.01) |
| *C07D 403/12* | (2006.01) |
| *C07D 403/10* | (2006.01) |

(52) U.S. Cl.
CPC .......... *A61K 31/551* (2013.01); *A61K 31/517* (2013.01); *C07D 239/91* (2013.01); *C07D 403/04* (2013.01); *C07D 403/10* (2013.01); *C07D 403/12* (2013.01); *Y02A 50/473* (2018.01)

(58) Field of Classification Search
CPC .................................................. A61K 31/551
USPC ......................................................... 514/220
See application file for complete search history.

(56) References Cited

U.S. PATENT DOCUMENTS

| | | |
|---|---|---|
| 2,065,593 A | 12/1936 | Lubs |
| 2,065,900 A | 12/1936 | Laska et al. |
| 2,071,329 A | 2/1937 | Brown |
| 3,251,837 A | 5/1966 | Holland |
| 3,600,394 A | 8/1971 | Coyne et al. |
| 3,773,946 A | 11/1973 | Creger |
| 3,930,024 A | 12/1975 | Creger |
| 3,965,128 A | 6/1976 | Fürst et al. |
| 4,159,330 A | 6/1979 | Doria et al. |
| 4,251,531 A | 2/1981 | Doria et al. |
| 4,613,593 A | 9/1986 | Yamatsu et al. |
| 4,689,344 A | 8/1987 | Bar-Tana |
| 4,711,896 A | 12/1987 | Bar-Tana et al. |
| 4,825,005 A | 4/1989 | Frey et al. |
| 5,098,903 A | 3/1992 | Magarian et al. |
| 5,124,337 A | 6/1992 | Dugar et al. |
| 5,126,351 A | 6/1992 | Luzzio et al. |
| 5,244,904 A | 9/1993 | Nagase et al. |
| 5,280,024 A | 1/1994 | Bolland et al. |
| 5,354,749 A | 10/1994 | Dressel et al. |
| 5,407,942 A | 4/1995 | Dressel et al. |
| 5,409,930 A | 4/1995 | Spada et al. |
| 5,446,071 A | 8/1995 | Grese |
| 5,474,994 A | 12/1995 | Leonardi et al. |
| 5,480,883 A | 1/1996 | Spada et al. |
| 5,539,119 A | 7/1996 | Nagase et al. |
| 5,576,322 A | 11/1996 | Takase et al. |
| 5,595,974 A | 1/1997 | Tomaru |
| 5,693,652 A | 12/1997 | Takase et al. |
| 5,707,987 A | 1/1998 | Nakagawa et al. |
| 5,733,913 A | 3/1998 | Blankley et al. |
| 5,756,344 A | 5/1998 | Onda et al. |
| 5,756,544 A | 5/1998 | Bisgaier et al. |
| 5,756,736 A | 5/1998 | Arzeno et al. |
| 5,756,763 A | 5/1998 | Takeuchi et al. |
| 5,763,414 A | 6/1998 | Bok et al. |
| 5,783,577 A | 7/1998 | Houghten et al. |
| 5,792,461 A | 8/1998 | Bok et al. |
| 5,792,902 A | 8/1998 | Benoit et al. |
| 5,798,344 A | 8/1998 | Kuroki et al. |
| 5,801,180 A | 9/1998 | Takase et al. |
| 5,817,674 A | 10/1998 | Clemence et al. |
| 5,854,264 A | 12/1998 | Anthony et al. |
| 5,877,208 A | 3/1999 | Bok et al. |
| 5,922,866 A | 7/1999 | Miyata et al. |
| 5,965,556 A | 10/1999 | Takeuchi et al. |
| 6,022,901 A | 2/2000 | Goodman |
| 6,048,903 A | 4/2000 | Toppo |
| 6,054,435 A | 4/2000 | Or et al. |
| 6,133,241 A | 10/2000 | Bok et al. |
| 6,165,984 A | 12/2000 | Bok et al. |

(Continued)

FOREIGN PATENT DOCUMENTS

| | | |
|---|---|---|
| AU | 719140 B2 | 7/1998 |
| CA | 2104981 A1 | 3/1994 |

(Continued)

OTHER PUBLICATIONS

"Gildants", in *Remington. The Science and Practice of Pharmacy*. 21st Edition. David B. Troy (Ed.). Philadelphia, PA: Lippincott Williams & Wilkins, 2006; p. 893.

(Continued)

*Primary Examiner* — Yong L Chu
(74) *Attorney, Agent, or Firm* — Finnegan, Henderson, Farabow, Garrett & Dunner, LLP

(57) ABSTRACT

The invention comprises methods of modulating the complement cascade in a mammal and for treating and/or preventing diseases and disorders associated with the complement pathway by administering a compound of Formula I or Formula II, such as, for example, 2-(4-(2-hydroxyethoxy)-3,5-dimethylphenyl)-5,7-dimethoxyquinazolin-4(3H)-one or a pharmaceutically acceptable salt thereof.

6 Claims, 7 Drawing Sheets

(56) References Cited

U.S. PATENT DOCUMENTS

| | | |
|---|---|---|
| 6,168,776 B1 | 1/2001 | Klunk et al. |
| 6,239,114 B1 | 5/2001 | Guthrie et al. |
| 6,291,456 B1 | 9/2001 | Stein et al. |
| 6,303,629 B1 | 10/2001 | Kun |
| 6,340,759 B1 | 1/2002 | Ueno et al. |
| 6,414,037 B1 | 7/2002 | Pezzuto et al. |
| 6,455,577 B2 | 9/2002 | Bok et al. |
| 6,479,499 B1 | 11/2002 | Kuo et al. |
| 6,482,479 B1 | 11/2002 | Dübal et al. |
| 6,512,161 B1 | 1/2003 | Rouy et al. |
| 6,521,253 B1 | 2/2003 | Forsman et al. |
| 6,541,045 B1 | 4/2003 | Charters et al. |
| 6,541,522 B2 | 4/2003 | Inman et al. |
| 6,548,548 B2 | 4/2003 | Campbell et al. |
| 6,613,772 B1 | 9/2003 | Schindler et al. |
| 6,635,642 B1 | 10/2003 | Jackson et al. |
| 6,673,780 B2 | 1/2004 | Dasseux et al. |
| 6,703,422 B2 | 3/2004 | Dasseux et al. |
| 6,723,319 B1 | 4/2004 | Ito et al. |
| 7,087,612 B2 | 8/2006 | Rodriguez Sarmiento et al. |
| 7,173,128 B2 | 2/2007 | Ravichandran et al. |
| 7,244,776 B2 | 7/2007 | Ravichandran et al. |
| 7,655,699 B1 | 2/2010 | Boehm et al. |
| 7,846,915 B2 | 12/2010 | Wong et al. |
| 7,872,052 B2 | 1/2011 | Linschoten |
| 8,053,440 B2 | 11/2011 | Hansen |
| 8,093,273 B2 | 1/2012 | Wong et al. |
| 8,114,995 B2 | 2/2012 | Hansen et al. |
| 8,242,130 B2 | 8/2012 | Wong et al. |
| 8,242,144 B2 | 8/2012 | Wong et al. |
| 8,410,109 B2 | 4/2013 | Wong et al. |
| 8,440,196 B1 | 5/2013 | Funakoshi et al. |
| 8,569,288 B2 | 10/2013 | Kempen et al. |
| 8,691,747 B2 | 4/2014 | Kruidenier et al. |
| 8,884,046 B2 | 11/2014 | Lozanov et al. |
| 8,889,698 B2 | 11/2014 | Hansen |
| 8,952,021 B2 | 2/2015 | Hansen |
| 9,125,915 B2 | 9/2015 | Miyoshi et al. |
| 9,199,990 B2 | 12/2015 | Hansen |
| 9,238,640 B2 | 1/2016 | Hansen |
| 9,255,089 B2 | 2/2016 | Aktoudianakis et al. |
| 9,278,940 B2 | 3/2016 | Fairfax et al. |
| 9,328,117 B2 | 5/2016 | Albrecht et al. |
| 9,522,920 B2 | 12/2016 | Albrecht et al. |
| 9,610,251 B2 | 4/2017 | Shenoy |
| 9,624,244 B2 | 4/2017 | Albrecht et al. |
| 9,675,697 B2 | 6/2017 | Wang et al. |
| 9,695,179 B2 | 7/2017 | Vankayalapati et al. |
| 9,757,368 B2 | 9/2017 | Hansen et al. |
| 9,765,039 B2 | 9/2017 | Fairfax et al. |
| 9,814,728 B2 | 11/2017 | Sverdrup et al. |
| 9,861,637 B2 | 1/2018 | Liu et al. |
| 10,111,885 B2 * | 10/2018 | Kulikowski ......... A61K 31/551 |
| 2002/0004608 A1 | 1/2002 | Alig et al. |
| 2002/0025301 A1 | 2/2002 | Haremza et al. |
| 2002/0091263 A1 | 7/2002 | Trova |
| 2003/0064967 A1 | 4/2003 | Luchoomun et al. |
| 2003/0068526 A1 | 4/2003 | Kamatani et al. |
| 2003/0072964 A1 | 4/2003 | Kwong et al. |
| 2003/0105102 A1 | 6/2003 | Li et al. |
| 2003/0171429 A1 | 9/2003 | Chen et al. |
| 2004/0001834 A1 | 1/2004 | Kim et al. |
| 2004/0033480 A1 | 2/2004 | Wong |
| 2004/0058903 A1 | 3/2004 | Takasugi et al. |
| 2004/0097493 A1 | 5/2004 | Chen et al. |
| 2004/0198750 A1 | 10/2004 | Green et al. |
| 2004/0235888 A1 | 11/2004 | Yamamori et al. |
| 2004/0242615 A1 | 12/2004 | Yamamori et al. |
| 2004/0248950 A1 | 12/2004 | Ishizuka et al. |
| 2005/0043300 A1 | 2/2005 | Middleton et al. |
| 2005/0080021 A1 | 4/2005 | Tucker et al. |
| 2005/0080024 A1 | 4/2005 | Tucker et al. |
| 2005/0096391 A1 | 5/2005 | Holm et al. |
| 2005/0261319 A1 | 11/2005 | Deuschle et al. |
| 2006/0116364 A1 | 6/2006 | Hamaoka et al. |
| 2007/0032430 A1 | 2/2007 | Fogelman et al. |
| 2007/0099826 A1 | 5/2007 | Wong et al. |
| 2007/0185160 A1 | 8/2007 | Hattori et al. |
| 2007/0218155 A1 | 9/2007 | Kuhrts |
| 2008/0085911 A1 | 4/2008 | Rongen et al. |
| 2008/0152595 A1 | 6/2008 | Emigh et al. |
| 2008/0275069 A1 | 11/2008 | Mizutani et al. |
| 2010/0055173 A1 | 3/2010 | Penhasi et al. |
| 2010/0093636 A1 | 4/2010 | Schultz et al. |
| 2010/0137400 A1 | 6/2010 | Karavas et al. |
| 2010/0152213 A1 | 6/2010 | Gil Ayuso-Gontan et al. |
| 2011/0117659 A1 | 5/2011 | Haugland et al. |
| 2011/0201608 A1 | 8/2011 | Hoffman et al. |
| 2011/0294807 A1 | 12/2011 | Hansen |
| 2012/0040954 A1 | 2/2012 | Hansen |
| 2012/0121698 A1 | 5/2012 | Manku et al. |
| 2013/0281397 A1 | 10/2013 | McLure et al. |
| 2013/0281398 A1 | 10/2013 | McLure et al. |
| 2013/0281399 A1 | 10/2013 | McLure et al. |
| 2014/0107369 A1 | 4/2014 | Lozanov et al. |
| 2014/0140956 A1 | 5/2014 | Fairfax et al. |
| 2014/0227321 A1 | 8/2014 | Iadonato et al. |
| 2015/0366877 A1 | 12/2015 | Yu et al. |
| 2016/0106750 A1 | 4/2016 | Hansen |
| 2016/0137613 A1 | 5/2016 | Hansen |
| 2016/0206617 A1 | 7/2016 | Lebioda et al. |
| 2016/0244826 A1 | 8/2016 | Dube et al. |
| 2016/0263126 A1 | 9/2016 | Kulikowski et al. |
| 2017/0044127 A1 | 2/2017 | Wei et al. |
| 2017/0119767 A1 | 5/2017 | Shenoy |
| 2017/0233812 A1 | 8/2017 | Dube et al. |
| 2017/0260510 A1 | 9/2017 | Dawson et al. |
| 2017/0326143 A1 | 11/2017 | Hansen et al. |
| 2017/0333419 A1 | 11/2017 | Hansen et al. |

FOREIGN PATENT DOCUMENTS

| | | |
|---|---|---|
| CA | 2345406 A1 | 4/2000 |
| CA | 2676984 A1 | 8/2008 |
| CA | 2815127 A1 | 4/2012 |
| CA | 2851996 A1 | 5/2013 |
| CN | 1067070 C | 6/2001 |
| CN | 1430599 A | 7/2003 |
| CN | 101365446 B | 5/2013 |
| CN | 101641339 B | 7/2013 |
| CN | 104918912 A | 9/2015 |
| CN | 106176753 A | 12/2016 |
| CN | 106265679 A | 1/2017 |
| DE | 35 32 279 A1 | 3/1987 |
| DE | 36 01 417 A1 | 7/1987 |
| DE | 42 15 588 A1 | 11/1993 |
| DE | 196 51 099 A1 | 6/1998 |
| DE | 197 56 388 A1 | 6/1999 |
| DE | 199 34 799 A1 | 2/2001 |
| EP | 0 210 342 A2 | 2/1987 |
| EP | 0 182 213 B1 | 9/1990 |
| EP | 0 407 217 A1 | 1/1991 |
| EP | 0 410 834 A1 | 1/1991 |
| EP | 0 258 190 B1 | 11/1991 |
| EP | 0 488 602 A1 | 6/1992 |
| EP | 0 272 455 B1 | 2/1993 |
| EP | 0 375 404 B1 | 2/1994 |
| EP | 0 333 175 B1 | 6/1994 |
| EP | 0 343 499 B1 | 7/1994 |
| EP | 0 409 413 B1 | 8/1994 |
| EP | 0 420 511 B1 | 8/1994 |
| EP | 0 633 022 A2 | 1/1995 |
| EP | 0 569 795 B1 | 4/1995 |
| EP | 0 330 108 B1 | 12/1995 |
| EP | 0 747 051 A2 | 12/1996 |
| EP | 0 564 350 B1 | 5/1997 |
| EP | 0 643 119 B1 | 4/2000 |
| EP | 1 125 908 A1 | 8/2001 |
| EP | 0 498 723 B1 | 9/2001 |
| EP | 0 607 439 B1 | 1/2002 |

(56) References Cited

FOREIGN PATENT DOCUMENTS

| | | |
|---|---|---|
| EP | 0 776 893 B1 | 2/2002 |
| EP | 1 195 378 A1 | 4/2002 |
| EP | 1 277 738 A1 | 1/2003 |
| EP | 1 398 032 A1 | 3/2004 |
| EP | 1 418 164 A1 | 5/2004 |
| EP | 1 426 046 A1 | 6/2004 |
| EP | 1 477 481 A1 | 11/2004 |
| EP | 1 637 523 A1 | 3/2006 |
| EP | 1 757 594 A1 | 2/2007 |
| EP | 1 944 301 A1 | 7/2008 |
| EP | 2 005 941 A2 | 12/2008 |
| EP | 2 433 637 B1 | 6/2014 |
| FR | 2 244 492 | 4/1975 |
| FR | 2 244 493 | 4/1975 |
| GB | 472489 | 9/1937 |
| GB | 728767 | 4/1955 |
| GB | 1175808 | 12/1969 |
| GB | 1179019 | 1/1970 |
| GB | 2 292 149 A | 2/1996 |
| IE | 902587 A1 | 7/1990 |
| JP | 6-80656 A | 3/1994 |
| JP | 7-41442 A | 2/1995 |
| JP | 7-61942 A | 3/1995 |
| JP | 7-118241 A | 5/1995 |
| JP | 7-179380 A | 7/1995 |
| JP | 7-233109 A | 9/1995 |
| JP | 7-247289 A | 9/1995 |
| JP | 8-104679 A | 4/1996 |
| JP | 10-287678 A | 10/1998 |
| JP | 2004-511502 A | 4/2001 |
| JP | 2001-131151 A | 5/2001 |
| JP | 2001-139550 A | 5/2001 |
| JP | 2001-335476 A | 12/2001 |
| JP | 2002-249483 A | 9/2002 |
| JP | 2004-203751 A | 7/2004 |
| JP | 2004-307440 A | 11/2004 |
| JP | 2005-532275 A | 10/2005 |
| JP | 2008-503537 A | 2/2008 |
| JP | 2010-530438 A | 9/2010 |
| KR | 10-0707532 B1 | 8/2005 |
| NZ | 556545 A | 3/2009 |
| RU | 2261861 C1 | 10/2005 |
| WO | WO 91/18901 A1 | 12/1991 |
| WO | WO 92/09374 A1 | 6/1992 |
| WO | WO 92/18123 A2 | 10/1992 |
| WO | WO 92/20642 A1 | 11/1992 |
| WO | WO 92/21661 A1 | 12/1992 |
| WO | WO 93/07124 A1 | 4/1993 |
| WO | WO 93/08174 A1 | 4/1993 |
| WO | WO 93/12095 A1 | 6/1993 |
| WO | WO 94/14763 A1 | 7/1994 |
| WO | WO 95/03277 A1 | 2/1995 |
| WO | WO 95/23150 A1 | 8/1995 |
| WO | WO 96/15128 A2 | 5/1996 |
| WO | WO 96/31206 A2 | 10/1996 |
| WO | WO 97/10221 A1 | 3/1997 |
| WO | WO 97/15308 A1 | 5/1997 |
| WO | WO 97/28118 A1 | 8/1997 |
| WO | WO 97/28132 A1 | 8/1997 |
| WO | WO 97/28134 A1 | 8/1997 |
| WO | WO 97/29106 A1 | 8/1997 |
| WO | WO 97/48694 A1 | 12/1997 |
| WO | WO 98/11438 A1 | 3/1998 |
| WO | WO 98/26127 A1 | 6/1998 |
| WO | WO 98/30530 A1 | 7/1998 |
| WO | WO 98/50370 A1 | 11/1998 |
| WO | WO 98/51307 A1 | 11/1998 |
| WO | WO 98/51308 A1 | 11/1998 |
| WO | WO 98/55124 A1 | 12/1998 |
| WO | WO 99/00116 A2 | 1/1999 |
| WO | WO 99/11634 A1 | 3/1999 |
| WO | WO 99/18077 A1 | 4/1999 |
| WO | WO 99/29667 A1 | 6/1999 |
| WO | WO 99/47170 A1 | 9/1999 |
| WO | WO 00/10607 A1 | 3/2000 |
| WO | WO 00/13671 A1 | 3/2000 |
| WO | WO 00/17184 A1 | 3/2000 |
| WO | WO 00/23075 A1 | 4/2000 |
| WO | WO 00/35865 A2 | 6/2000 |
| WO | WO 00/44362 A2 | 8/2000 |
| WO | WO 00/55168 A1 | 9/2000 |
| WO | WO 00/64888 A1 | 11/2000 |
| WO | WO 01/00554 A2 | 1/2001 |
| WO | WO 01/60775 A1 | 8/2001 |
| WO | WO 01/82916 A2 | 11/2001 |
| WO | WO 01/83456 A1 | 11/2001 |
| WO | WO 01/90051 A1 | 11/2001 |
| WO | WO 02/32377 A2 | 4/2002 |
| WO | WO 02/044189 A1 | 6/2002 |
| WO | WO 02/074307 A1 | 9/2002 |
| WO | WO 02/087556 A2 | 11/2002 |
| WO | WO 02/096426 A1 | 12/2002 |
| WO | WO 03/007959 A1 | 1/2003 |
| WO | WO 03/011829 A1 | 2/2003 |
| WO | WO 03/016292 A1 | 2/2003 |
| WO | WO 03/018008 A1 | 3/2003 |
| WO | WO 03/040256 A2 | 5/2003 |
| WO | WO 03/040257 A1 | 5/2003 |
| WO | WO 03/070236 A2 | 8/2003 |
| WO | WO 03/076427 A1 | 9/2003 |
| WO | WO 03/099274 A1 | 12/2003 |
| WO | WO 03/106435 A1 | 12/2003 |
| WO | WO 2004/017920 A2 | 3/2004 |
| WO | WO 2004/019933 A1 | 3/2004 |
| WO | WO 2004/032846 A2 | 4/2004 |
| WO | WO 2004/037176 A2 | 5/2004 |
| WO | WO 2004/039795 A2 | 5/2004 |
| WO | WO 2004/041755 A2 | 5/2004 |
| WO | WO 2004/047755 A2 | 6/2004 |
| WO | WO 2004/054985 A1 | 7/2004 |
| WO | WO 2004/056355 A1 | 7/2004 |
| WO | WO 2004/058717 A1 | 7/2004 |
| WO | WO 2004/065392 A1 | 8/2004 |
| WO | WO 2004/072042 A2 | 8/2004 |
| WO | WO 2004/092196 A2 | 10/2004 |
| WO | WO 2004/094452 A2 | 11/2004 |
| WO | WO 2004/108139 A2 | 12/2004 |
| WO | WO 2004/112710 A2 | 12/2004 |
| WO | WO 2005/034960 A1 | 4/2005 |
| WO | WO 2005/042712 A2 | 5/2005 |
| WO | WO 2005/065183 A2 | 7/2005 |
| WO | WO 2005/066162 A1 | 7/2005 |
| WO | WO 2005/075431 A1 | 8/2005 |
| WO | WO 2005/115993 A1 | 12/2005 |
| WO | WO 2006/000420 A1 | 1/2006 |
| WO | WO 2006/012577 A2 | 2/2006 |
| WO | WO 2006/045096 A2 | 2/2006 |
| WO | WO 2006/071095 A1 | 7/2006 |
| WO | WO 2006/105081 A2 | 10/2006 |
| WO | WO 2007/016525 A2 | 10/2006 |
| WO | WO 2007/071055 A1 | 6/2007 |
| WO | WO 2008/059024 A1 | 5/2008 |
| WO | WO 2008/092231 A1 | 8/2008 |
| WO | WO 2008/152471 A1 | 12/2008 |
| WO | WO 2008/157575 A1 | 12/2008 |
| WO | WO 2010/015520 A1 | 2/2010 |
| WO | WO 2010/049466 A1 | 5/2010 |
| WO | WO 2010/056910 A1 | 5/2010 |
| WO | WO 2010/100178 A1 | 9/2010 |
| WO | WO 2010/127099 A2 | 11/2010 |
| WO | WO 2011/135376 A1 | 11/2011 |
| WO | WO 2012/052102 A1 | 4/2012 |
| WO | WO 2012/112531 A1 | 8/2012 |
| WO | WO 2013/156869 A1 | 10/2013 |
| WO | WO 2014/062428 A1 | 4/2014 |
| WO | WO 2014/080291 A2 | 5/2014 |
| WO | WO 2014/110090 A1 | 7/2014 |
| WO | WO 2015/025226 A2 | 2/2015 |
| WO | WO 2015/025228 A2 | 2/2015 |
| WO | WO 2016/123054 A2 | 8/2016 |
| WO | WO 2016/145294 A1 | 9/2016 |

(56) References Cited

FOREIGN PATENT DOCUMENTS

| WO | WO 2016/182904 A1 | 11/2016 |
|----|-------------------|---------|
| WO | WO 2016/201370 A1 | 12/2016 |

OTHER PUBLICATIONS

"RVX 208" R&D Insight Profile in *Drugs* 11(2):207-213 (2011).
Abbott et al., "High density lipoprotein cholesterol, total cholesterol screening, and myocardial infarction" *Arteriosclerosis* 8:207-211 (1988).
Abdel-Jalil et al., "Synthesis and Antitumor Activity of 2-Aryl-7-fluoro-6-(4-methyl-1-piperazinyl)-4(3H)-guinazolinones" *Heterocycles* 65(9):2061-2070 (2005).
Abdul-Rahman et al., "Dinuclear molybdenum complexes derived from diphenols: electrochemical interactions and reduced species" *Polyhedron* 16(24):4353-4362 (1997).
Acton et al., "Identification of Scavenger Receptor SR-BI as a High Density Lipoprotein Receptor" *Science* 271:518-520 (1996).
Adamis, "Is diabetic retinopathy an inflammatory disease?" *Br. J. Ophthamol.* 86:363-365 (2002).
Aiello et al. "ABCA1-Deficient Mice. Insights Into the Role of Monocyte Lipid Efflux in HDL Formation and Inflammation" *Arterioscler. Thromb. Vasc. Biol.* 23:972-980 (2003).
Alchi, B. and D. Jayne (2010) "Membranoproliferative glomerulonephritis" *Pediatr Nephrol*, 25:1409-1418.
Alla et al., "A Reappraisal of the Risks and Benefits of Treating to Target with Cholesterol Lowering Drugs" *Drugs* 73(10):1025-1054 (2013).
Anderson et al. (2010) "The pivotal role of the complement system in aging and age-related macular degeneration: Hypothesis revisited" *Prog. Retin. Eye Res.* 29(2):95-112. NIH Author Manuscript; available in PMC May 2, 2013 (40 pages).
Andersson, "Pharmacology of apolipoprotein A-I" *Curr. Opin. Lipidol.* 8:225-228 (1997).
Angelucci, F. and L. Colantoni (2010) "Facioscapulohumeral muscular dystrophy: Do neurotrophins play a role?" *Muscle Nerve*, 41:120-127.
Annunziata, P. and N. Volpi (1985) "High levels of $C_3c$ in the cerebrospinal fluid from amyotrophic lateral sclerosis patients" *Acta Neurol Scand*, 72:61-64.
Ansell et al., "The paradox of dysfunctional high-density lipoprotein" *Curr. Opin. Lipidol.* 18:427-434 (2007).
Apostolski, S. et al. (1991) "Serum and CSF immunological findings in ALS" *Acta Neurol Scand*, 83:96-98.
Assmann et al., "The Münster Heart Study (PROCAM). Results of Follow-up at 8 Years" *Eur. Heart J.* 19(A):A2-A11 (1998).
Asztalos, "High-Density Lipoprotein Metabolism and Progression of Atherosclerosis: New Insights from the HDL Atherosclerosis Treatment Study" *Curr. Opin. Cardiol.* 19:385-391 (2004).
ATBC Cancer Prevention Study Group, "The Alpha-Tocopherol, Beta-Carotene Lung Cancer Prevention Study: Design, Methods, Participant Characteristics, and Compliance" Elsevier Science Inc., *AEP* 4(1):1-10 (1994).
Atreya and Neurath, "Involvement of IL-6 in the Pathogenesis of Inflammatory Bowel Disease and Colon Cancer" *Clin. Rev. Allergy Immunol.*, 28:187-195 (2005).
Avicel PH, product information from FMC [online]; downloaded from http://www.fmcbiopolymercom/Portals/Pharm/Content/Docs.pdf on Aug. 15, 2013 (2 pages).
Avicel® PH-301, Product Specification Bulletin, FMC Corporation [online]; downloaded from http://www.signetchem.com/downloads/datasheets/Fmc-biopolymer/Avicel-Ph-301-Specifications.pdf, on May 13, 2015.
Baba et al., "Continuous intake of polyphenolic compounds containing cocoa powder reduces LDL oxidative susceptibility and has beneficial effects on plasma HDL-cholesterol concentrations in humans" *Am. J. Clin. Nutr.* 85:709-717 (2007).

Badimon et al. "Regression of Atherosclerotic Lesions by High Density Lipoprotein Plasma Fraction in the Cholesterol-fed Rabbit" *J. Clin. Invest.* 85: 1234-1241 (1990).
Badimon et al., "Role of High Density Lipoproteins in the Regression of Atherosclerosis" *Circulation* 86(Suppl. III):86-94 (1992).
Bagul et al., "Current Status of Tablet Disintegrants: A Review" Online: http://www.pharmainfo.net/reviews/current-status-tablet-disintegrantsa-review, 2006, 16 pages.
Bailey et al., "RVX-208: A small molecule that increases apolipoprotein A-I and high-density lipoprotein cholesterol in vitro and in vivo" *J Am Coll Cardiol*, 55:2580-2589 (2010).
Ballantyne, C.M. et al. (Aug. 19, 2008) "Statin Therapy Alters the Relationship Between Apolipoprotein B and Low-Density Lipoprotein Cholesterol and Non-High-Density Lipoprotein Cholesterol Targets in High-Risk Patients" *J Am Coll Cardiol*, 52(8):626-632.
Baron et al., "The pathogenesis of adoptive murine autoimmune diabetes requires an interaction between α4-integrins and vascular cell adhesion molecule-1" *J. Clin. Invest.*, 93:1700-1708 (1994).
Barrans et al., "Pre-β HDL: Structure and Metabolism" *Biochim. Biophys. Acta* 1300:73-85 (1996).
Barter et al., "Antiinflammatory Properties of HDL" *Circ. Res.* 95:764-772 (2004).
Barter et al., "High Density Lipoproteins and Coronary Heart Disease" *Atherosclerosis* 121:1-12 (1996).
Bauer and Hermann, "Interleukin-6 in clinical medicine" *Ann. Hematol.*, 62:203-210 (1991).
Bayly et al., "Electronic and magnetic metal-metal interactions in dinuclear oxomolybdenum(V) complexes across bis-phenolate bridging ligands with different spacers between the phenolate termini: ligand-centered vs. metal-centered redox activity" *J. Chem. Soc., Dalton Transactions* 9:1401-1414 (2001).
Bayraktar et al., "The clinical spectrum of catastrophic antiphospholipid syndrome in the absence and presence of lupus" *J. Rhematol.*, 34(2):346-352 (2007).
Beckers et al, "Single nucleotide polymorphisms in inflammation-related genes are associated with venous thromboembolism" *Eur. J. Int. Med.*, 21:289-292 (2010).
Belalcazar et al., "Long-Term Stable Expression of Human Apolipoprotein A-I Mediated by Helper-Dependent Adenovirus Gene Transfer Inhibits Atherosclerosis Progression and Remodels Atherosclerotic Plaques in a Mouse Model of Familial Hypercholesterolemia" *Circulation* 107:2726-2732 (2003).
Benson et al., "Topical steroid treatment of allergic rhinitis decreases nasal fluid $T_H2$ cytokines, eosinophils, eosinophil cationic protein, and IgE but has no significant effect on IFN-γ, IL-1β, TNF-α, or neutrophils" *J. Allergy Clin. Immunol.* 106:307-312 (2000).
Berentsen, S. (2015) "Role of Complement in Autoimmune Hemolytic Anemia" *Transfus Med Hemother*, 42:303-310.
Berentsen, S. et al. (2015) "Cold Agglutinin-Mediated Autoimmune Hemolytic Anemia" *Hematol Oncol Clin N Am*, 29:455-471.
Bergamaschini, L. et al. (1999) "Consumption of C4b-binding protein (C4BP) during in vivo activation of the classical complement pathway" *Clin Exp Immunol*, 116:220-224.
Berliner et al., "Atherosclerosis: Basic Mechanisms. Oxidation, Inflammation and Genetics" *Circulation*, 91:2488-2496 (1995).
Berman et al., "Emerging anti-inflammatory drugs for atherosclerosis" *Expert Opin. Emerg. Drugs*, 18:193-205 (2013).
Bertele et al., "Platelet Thromboxane Synthetase Inhibitors with Low Doses of Aspirin: Possible Resolution of the 'Aspirin Dilemma'" *Science* 220:517-519 (1983).
Beugelmans et al., "One-pot Synthesis of 1-Oxo-1,2-Dihydroisoquinolines (Isocarbostyrils) Via $S_{RN}1$ (Ar) Reactions" *Synthesis* 9:729-731 (1981).
Bhilare et al., "Ionic-Liquid-Influenced Expeditious and Stereoselective Synthesis of Olefins" *Synthetic Communications* 37(18):3111-3117 (2007).
Biesecker, G. and C.M. Gomez (1989) "Inhibition of acute passive transfer experimental autoimmune myasthenia gravis with Fab antibody to complement C6" *J Immunol*, 142:2654-2659.
Bindu et al., "Friend Turns Foe: Transformation of Anti-Inflammatory HDL to Proinflammatory HDL during Acute-Phase Response" *Cholesterol*, 2011: Article ID 274629 [online] doi:10.1155/2011/274629, 7 pages (2011).

(56) References Cited

OTHER PUBLICATIONS

Bisagni et al., "A Convenient Way to Dibenzo[c,h]-1,5-Naphthyridines (11-Aza-Benzo[c]phenanthridines)" *Tetrahedron* 52:10427-10440 (1996).
Bisgaier et al., "A Novel Compound that Elevates High Density Lipoprotein and Activates the Peroxisome Proliferator Activated Receptor" *J. Lipid Res.* 39:17-30 (1998).
Bjerre et al., "High osteopontin levels predict long-term outcome after STEMI and primary percutaneous coronary intervention" *Eur. J. Prev. Cardiol.* 20:922-929 (2013).
Blackburn Jr., W.D. et al., "Apolipoprotein A-I decreases neutrophil degranulation and superoxide production" *J. Lipid Res.* 32:1911-1918 (1991).
Bomback, A.S. et al. (2012) "Eculizumab for Dense Deposit Disease and C3 Glomerulonephritis" *Clin J Am Soc Nephrol*, 7:748-756.
Booth and Bishop, "TGF-β, Il-6, IL-17 and CTGF direct multiple pathologies of chronic cardiac allograft rejection" *Immunotherapy*, 2(4):511-520 (2010). Author manuscript, NIH Public Access, May 1, 2011.
Bora, N. et al. (2010) "Recombinant Membrane-targeted Form of CD59 Inhibits the Growth of Choroidal Neovascular Complex in Mice" *J Biol Chem*, 285:33826-33833.
Borgatti et al. (2010) "Induction by TNF-α of IL-6 and IL-8 in Cystic Fibrosis Bronchial IB3-1 Epithelial Cells Encapsulated in Alginate Microbeads," *J. Biomed. Biotechnol.* 2010: Article ID 907964, doi: 10.1155/2010/907964 (11 pages).
Boyce et al., "The Acylation and Alkylation of o-Tolunitrile. A New Route to 3-Substituted Isocarbostyrils" *J. Org. Chem.* 31:3807-3809 (1966).
Bradsher et al., "A New Isoquinoline Synthesis Via ORTHO-Substituted Benzylamines" *Tetrahedron Lett.* 31:3149-3150 (1972).
Bradsher et al., "α-Acyl-o-Tolunitriles as Intermediates in the Preparation of 3-Substituted Isoquinolines and 1-Amino-2-benzopyrylium Derivatives" *J. Org. Chem.* 43:3817-3820 (1978).
Brennan, F. et al. (2016) "Therapeutic targeting of complement to modify disease course and improve outcomes in neurological conditions" *Seminars in Immunology*, 28:292-308.
Brewer, Jr. et al., "Human plasma proapoA-I: Isolation and amino-terminal sequence" *Biochem. Biophys. Res. Commun.* 113:626-632 (1983).
Brodsky, R. (2015) "Complement in hemolytic anemia" *Blood*, 126:2459-2465.
Brown et al., "NF-kappaB Directs Dynamic Super Enhancer Formation in Inflammation and Atherogenesis" *Mol. Cell* 56:219-231 (2014). NIH Public Access Author Manuscript, available in PMC Oct. 23, 2015 (24 pages).
Brugaletta et al., "NIRS and IVUS for Characterization of Atherosclerosis in Patients Undergoing Coronary Angiography" *JACC: Cardiovasc Imaging* 4(6):647-655 (2011).
Buhle et al., "Trivalent Carbon. II. Unsymmetrical Hexaaryldimethylperoxides" *J. Am. Chem. Soc.* 65:584-586 (1943).
Burkly et al., "Protection against adoptive transfer of autoimmune diabetes mediated through very late antigen-4 integrin" *Diabetes*, 43:529-534 (1994).
Cabot Corporation, "Untreated Fumed Silica: CAB-O-SIL® M-5" Product Information, PDS-147 (2004) (2 pages).
Cahlin et al., "Experimental Cancer Cachexia: The Role of Host-derived Cytokines Interleukin (IL)-6, IL-12, Interferon-γ, and Tumor Necrosis Factor α Evaluated in Gene Knockout, Tumor-bearing Mice on C57 BI Background and Eicosanoid-dependent Cachexia" *Cancer Res.*, 60:5488-5493 (2000).
Campbell et al, "Essential role for interferon-γ and interleukin-6 in autoimmune insulin-dependent diabetes in NOD/Wehi mice" *J. Clin. Invest.*, 87(2):739-742 (1991).
Campbell et al., "Neurologic disease induced in transgenic mice by cerebral overexpression of interleukin 6" *Proc. Natl. Acad. Sci. USA*, 90(21):10061-10065 (1993).

CAPLUS Accession No. 1991:449453, Liu et al. "Synthesis of 2-aryl-9-bromo-4-oxo-4H-pyrano[3,2-c]quinolines" [online]. Retrieved from STN on Jan. 31, 2011. Also published in: *Youji Huaxue* 11(2):191-195 (1991).
CAPLUS Accession No. 2003:554477, Qin et al., "Synthesis and fungicidal activity of novel diazaflavanones" [online]. Retrieved from STN on Jan. 31, 2011. Also published in: *Nongyaoxue Xuebao* 4(4):28-32 (2002).
CAPLUS Accession No. 2004:11346, Hu et al., "Synthesis and fungicidal activity of flavanone derivatives containing isopentenyl group" [online]. Retrieved from STN on Jan. 31, 2011. Also published in: *Yingyong Huaxue* 20(12):1161-1165 (2003).
CAPLUS Accession No. 2005:46491, Qin et al., "Synthesis and fungicidal activity of 5,7-dihydroxyldiazinflavanones" [online]. Retrieved from STN on Jan. 31, 2011. Also published in: *Huazhong Shifan Daxue Xuebao Zirankexueban* 38(3):323-325 (2004).
Castelli, "The triglyceride issue: A view from Framingham" *Am. Heart J.* 112:432-437 (1986).
Castillo et al., "Associations of four circulating chemokines with multiple atherosclerosis phenotypes in a large population-based sample: results from the Dallas Heart Study" *J Interferon Cytokine Res*, 30:339-347 (2010).
Chakrabarty et al., "Induction of apoptosis in human cancer cell lines by diospyrin, a plant-derived bisnaphthoquinonoid, and its synthetic derivatives" *Cancer Letters* 188(1-2):85-93 (2002).
Chambon, "A decade of molecular biology of retinoic acid receptors" *FASEB J.* 10:940-954 (1996).
Chang et al, "Biomarkers for neuromyelitis optica" *Clin. Chim. Acta*, 440:64-71 (2015).
Chartier et al., "Synthèse de diazaflavones" *Bull. Soc. Chim. Fr.* 11-12(Pt. 2):1916-1918 (1976). English abstract on p. 1916. Abstract.
Cheng et al., "Lipoprotein (a) and its relationship to risk factors and severity of atherosclerotic peripheral vascular disease" *Eur. J. Vasc. Endovasc. Surg.* 14:17-23 (1997).
Cheon, S.H. et al., "Structure-Activity Relationship Studies of Isoquinolinone Type Anticancer Agent" *Arch Pharm Res*, 24(4):276-280 (2001).
Cherubini et al., "Role of Antioxidants in Atherosclerosis: Epidemiological and Clinical Update" *Curr. Pharm. Des.* 11:2017-2032 (2005).
Cho et al., "Molecular Modeling of 3-Arylisoquinoline Antitumor Agents Active Against A-549. A Comparative Molecular Field Analysis Study" *Bioorg. Med. Chem.* 10:2953-2961 (2002).
Cho et al., "Synthesis and Antitumor Activity of 3-Arylisoquinoline Derivatives" *Arch. Pharm. Res.* 20:264-268 (1997).
Cho et al., "Synthesis and Biological Evaluation of 3-Arylisoquinolines As Antitumor Agents" *Bioorg. Med. Chem. Lett.* 8:41-46 (1998).
Cho et al., "Synthesis and Comparative Molecular Field Analysis (CoMFA) of Antitumor 3-Arylisoquinoline Derivatives" *Bioorg. Med. Chem.* 6(12):2449-2458 (1998).
Choudhary and Ahlawat, "Interleukin-6 and C-Reactive Protein in Pathogenesis of Diabetic Nephropathy" *Iran J. Kidney Dis.*, 2:72-79 (2008).
Chung et al., "Characterization of the Role of IL-6 in the Progression of Prostate Cancer" *The Prostate*, 38(3):199-207 (1999).
Chyu et al., "Differential Effects of Green Tea-Derived Catechin on Developing Versus Established Atherosclerosis in Apolipoprotein E-Null Mice" *Circulation* 109:2448-2453 (2004).
Clarkson et al., "Inhibition of Postmenopausal Atherosclerosis Progression: A Comparison of the Effects of Conjugated Equine Estrogens and Soy Phytoestrogens" *J. Clin. Endocrinol. Metab.* 86(1):41-47 (2001).
Clauson-Kaas et al., "Reactions of 3,4-dihydor-2H-pyrrido[3,2-b]-1,4-oxazines" *Acta Chemica Scandinavica* 25(8):3135-3143 (1971). Retrieved from STN, file HCAPLUS, Accession No. 1972:34186 (Abstract).
clinical trials.gov, U.S. National Institutes of Health, "ApoA-I Synthesis Stimulation and Intravascular Ultrasound for Coronary Atheroma Regression Evaluation (ASSURE I)" Study Identifier NCT01067820; first received Feb. 10, 2010. [online] Retrieved from: www.clinicaltrials.gov (4 pages).

(56) References Cited

OTHER PUBLICATIONS clinical trials.gov, U.S. National Institutes of Health, "Investigate the Efficacy and Safety of GSK1070806 in Obese Subjects With T2DM" Study Identifier NCT01648153; first received Jul. 12, 2012. [online] Retrieved from: www.clinicaltrials.gov (4 pages).
clinical trials.gov, U.S. National Institutes of Health, "The Study of Quantitative Serial Trends in Lipids With Apolipoprotein A-I Stimulation (SUSTAIN)" Study Identifier NCT01423188; first received Aug. 22, 2011. [online] Retrieved from: www.clinicaltrials.gov (4 pages).
Colaizzi and Klink (1969) "pH-Partition Behavior of Tetracyclines" *J. Pharm. Sci.*, 58(10):1184-1189.
Colotta et al., "Cancer-related inflammation, the seventh hallmark of cancer: links to genetic instability" *Carcinogenesis*, 30(7):1073-1081 (2009).
Connolly et al., "Synthesis of quinazolinones and quinazolines" *Tetrahedron* 61(43):10153-10202 (2005).
Cooper et al., "Wine polyphenols and promotion of cardiac health" *Nutr. Res. Rev.* 17:111-129 (2004).
Córdoba-Lanús et al., "Association of IL-6 Gene Polymorphisms and COPD in a Spanish Population" *Respiratory Medicine*, 102:1805-1811 (2008).
Cramer et al., "New Syntheses of Aryl Fluorides and Aryl Fluorosulfonates from Oxyflourides of Sulfur" *J. Org. Chem.* 26:4164-4165 (1961).
Csuka, D. et al. (2014) "Activation of the ficolin-lectin pathway during attacks of hereditary angioedema" *J Allergy Clinical Immunol*, 134:1388-1393e1.
Cui et al., "Interleukin-6 receptor blockade suppresses subretinal fibrosis in a mouse model" *Int. J. Ophthalmol.*, 7(2):194-197 (2014).
Daha, M. et al. (2016) "Role of complement in IgA nephropathy" *J Nephrol*, 29:1-4.
Dai et al., "Synthesis of 3,4-Disubstituted Isoquinolines via Palladium-Catalyzed Cross-Coupling of 2-(1-alkynyl)benzaldimines and Organic Halides" *J. Org. Chem.* 68:920-928 (2003).
Dai et al., "Synthesis of 3-Substituted 4-Aroylisoquinolines via Pd-Catalyzed Carbonylative Cyclization of 2-(1-Alkynyl)benzaldimines" *J. Org. Chem.* 67:7042-7047 (2002).
Daina, E. et al. (2012) "Eculizumab in a Patient with Dense-Deposit Disease" *N Engl J Med*, 366(12):1161-1163.
Dalakas, M. (2004) "Intravenous Immunoglobulin in Autoimmune Neuromuscular Diseases" *J Am Med Assoc*, 291(19):2367-2375.
Dansky et al., "High-Density Lipoprotein and Plaque Regression. The Good Cholesterol Gets Even Better" *Circulation* 100:1762-1763 (1999).
Dashti et al., "Leptin and Interleukin-6 in End-Stage Renal Disease" *Pak. J. Med. Sci.*, 24(5):694-697 (2008).
Dave, Rutesh H., "Overview of pharmaceutical excipients used in tablets and capsules" *Drug topics*, published Oct. 24, 2008 [online]. Retrieved from the Internet: http://drugtopics.modernmedicine.com/drug-topics/news/modernmedicine/modern-medicine-news/overview-pharmaceutical-excipients-used-tablets, on Mar. 11, 2015 (11 pages).
Dawson et al. (2011) "Inhibition of BET recruitment to chromatin as an effective treatment for MLL-fusion leukaemia" *Nature*, 478:529-533. Europe PMC Funders Group Author Manuscript; available in PMC Jun. 12, 2013 [online]. Retrieved from: https://www.ncbi.nlm.nih.gov/pmc/articles/PMC3679520/, on Feb. 27, 2018 (12 pages).
De Jager et al., "Chemokines CCL3/MIP1alpha, CCL5/RANTES and CCL18/PARC are independent risk predictors of short-term mortality in patients with acute coronary syndromes" *PloS one* 7:e45804 (2012).
De Paepe, B. and De Bleecker, J.L. (2013) "Cytokines and Chemokines as Regulators of Skeletal Muscle Inflammation: Presenting the Case of Duchenne Muscular Dystrophy" *Mediators of Inflammation*, vol. 2013, Article 540370 (10 pages).
Decossin et al., "Subclasses of LpA-I in Coronary Artery Disease: Distribution and Cholesterol Efflux Ability" *Eur. J. Clin. Invest.* 27:299-307 (1997).

Delmore et al. (2011) "BET Bromodomain Inhibition as a Therapeutic Strategy to Target c-Myc" *Cell*, 146:904-917.
Depta et al., "New approaches to inhibiting platelets and coagulation" *Annu. Rev. Pharmacol. Toxicol.* 55:373-397 (2015).
Devitt et al., "Synthesis of Heterocyclic-Substituted Chromones and Chalcones" *J. Org. Chem.* 26:4941-4944 (1961).
Diaz et al., "Critical Role for IL-6 in Hypertrophy and Fibrosis in Chronic Cardiac Allograft Rejection" *Am. J. Transplant.*, 9(8):1773-1783 (2009). NIH Public Access Author Manuscript; available in PMC Aug. 1, 2010 (20 pages).
Diepenhorst et al. (2009) "Complement-mediated ischemia-reperfusion injury: lessons learned from animal and clinical studies" *Ann. Surg.* 249(6):889-899.
Discipio (1982) "The activation of the alternative pathway C3 convertase by human plasma kallikrein" *Immunology* 45(3):587-595.
Dunkelberger and Song (2010) "Complement and its role in innate and adaptive immune responses" *Cell Res.* 20(1):34-50.
Duong et al., "The molecular physiology of nuclear retinoic acid receptors. From health to disease" *Biochim. Biophys. Acta* 1812:1023-1031 (2011).
Edwards et al., "Inhibition of myeloperoxidase release from rat polymorphonuclear leukocytes by a series of azachalcone derivatives" *J. Med. Chem.* 37(25):4357-4362 (1994).
Ehrlich, M. and M. Lacey (Aug. 2012) "Deciphering transcription dysregulation in FSH muscular dystrophy" *J Hum Genet*, 57(8):477-484. NIH Public Access Author Manuscript; available in PMC Feb. 1, 2013 (17 pages).
Eiden et al., "1,2-Bisbenzopyranyl-ethene" *Archiv. der Pharmazie* 313(2):120-128 (1980) (German). English abstract on p. 120.
Emilie et al., "Administration of an anti-interleukin-6 monoclonal antibody to patients with acquired immunodeficiency syndrome and lymphoma: effect on lymphoma growth and on B clinical symptoms" *Blood*, 84:2472-2479 (1994).
Endo, M. et al. (1998) "Glomerular deposition of mannose-binding lectin (MBL) indicates a novel mechanism of complement activation in IgA nephropathy" *Nephrology Dialysis Transplantation*, 13:1984-1990.
Esmon (2004) "The impact of the inflammatory response on coagulation" *Thromb Res.* 114(5-6):321-327.
Esterbauer et al., "Continuous Monitoring of In Vitro Oxidation of Human Low Density Lipoprotein" *Free Rad. Res. Comms.* 6:67-75 (1989).
Exner et al., "Interleukin-6 Promoter Genotype and Restenosis after Femoropopliteal Balloon Angioplasty: Initial Observations" *Radiology* 231:839-844 (2004).
Extended European Search Report dated Mar. 24, 2017, in European Patent Application No. 14837690.8, filed by Resverlogix Corp. (16 pages).
Extended European Search Report, including Supplementary Search Report and Opinion, dated Apr. 29, 2015 in European Patent Application 13846466, by Resverlogix Corp. (8 pages).
Extended European Search Report, including Supplementary Search Report and Opinion, dated Jun. 1, 2015, in European Patent Application 12844794.3, filed May 12, 2014, by Resverlogix Corp.
Farini, A. et al. (May 19, 2014) "Influence of Immune Responses in Gene/Stem Cell Therapies for Muscular Dystrophies" *BioMed Res International*, vol. 2014, Article 818107 (16 pages).
Fattori et al., "Development of Progressive Kidney Damage and Myeloma Kidney in Interleukin-6 Transgenic Mice" *Blood*, 83(9):2570-2579 (1994).
Feng et al., "Human ApoA-I Transfer Attenuates Transplant Arteriosclerosis via Enhanced Incorporation of Bone marrow-derived Endothelial Progenitor Cells" *Arterioscler. Thromb. Vasc. Biol.*, 28:278-283 (2008).
Ferreira et al., "Diversity of Structure and Function in Oligomeric Flavanoids" *Tetrahedron* 48:1743-1803 (1992).
Fiane et al. (1999) "Compstatin, a peptide inhibitor of C3, prolongs survival of ex vivo perfused pig xenografts" *Xenotransplantation* 6(1):52-65.
Fielding et al., "Molecular Physiology of Reverse Cholesterol Transport" *J. Lipid Res.* 36:211-228 (1995).

(56) References Cited

OTHER PUBLICATIONS

Fieser, L.F., "The potentials of some unstable oxidation-reduction systems" *J. Am. Chem. Soc.* 52:4915-4940 (1930).
Filippakopoulos et al., "Histone recognition and large-scale structural analysis of the human bromodomain family" *Cell* 149:214-231 (2012).
Filippakopoulos et al., "Selective inhibition of BET bromodomains" *Nature*, 468:1067-1073 (2010).
Finkel et al, "Interleukin-6 (IL-6) as a Mediator of Stunned Myocardium" *Am. J. Cardiol.*, 71:1231-1232 (1993).
Fisher Center for Alzheimer's Research Foundation, "Alzheimer's Disease: 'Good' Cholesterol May Help Keep Alzheimer's at Bay" The Ninth International Conference on Alzheimer's Disease and Related Disorders, Philadelphia, PA, Jul. 22, 2004. Retrieved from the Internet: http://www.alzinfo.org/newsarticle/templates/archivenewstemplate.asp?articleid=156&zoneid=7 on Jul. 28, 2010.
Fisher et al., "High-Density Lipoprotein Function, Dysfunction, and Reverse Cholesterol Transport" *Arterioscler. Thromb. Vasc. Biol.* 32:2813-2820 (2012).
Fisher et al., "Increased post-traumatic survival of neurons in IL-6-knockout mice on a background of EAE susceptibility" *J. Neuroimmunol.*, 119:1-9 (2001).
Flammang et al., "2,3-Benzodiazepines: 2-Aminoisoquinolinones From Ring Contraction of 1-oxo-2,3-Benzodiazepines" *C R Acad. Sci. Paris, Series C* 290:361-363 (1980) (French). English abstract on p. 361.
Floege, J. et al. (2014) "New insights into the pathogenesis of IgA nephropathy" *Semin Immunopathol*, 36:431-442.
Fokialakis et al., "A New Class of Phytoestrogens: Evaluation of the Estrogenic Activity of Deoxybenzoins" *Chem. Biol.* 11:397-406 (2004).
Folkman and Shing, "Angiogenesis" *J. Biol. Chem.*, 267(16):10931-10934 (1992).
Fonseca et al. (2009) "Treatment with a C5aR antagonist decreases pathology and enhances behavioral performance in murine models of Alzheimer's disease" *J. Immunol.* 183(2):1375-1383.
Forastiero et al. "Circulating levels of tissue factor and proinflammatory cytokines in patients with primary antiphospholipid syndrome or leprosy related antiphospholipid antibodies" *Lupus*, 129-136 (2005).
Francone et al., "Disruption of the murine procollagen C-proteinase enhancer 2 gene causes accumulation of pro-apoA-I and increased HDL levels" *J. Lipid Res.*, 52:1974-1983 (2011).
Frank, M. (2010) "Complement disorders and hereditary angioedema" *J Allergy Clin Immunol*, 125:S262-S271.
Frei et al., "Interleukin-6 is elevated in plasma in multiple sclerosis" *J. Neuroimmunol.*, 31:147-153 (1991).
Freireich et al., "Quantitative Comparison of Toxicity of Anticancer Agents in Mouse, Rat, Hamster, Dog, Monkey, and Man" *Cancer Chemother. Reports*, 50(4):219-244 (1966).
Frisullo, G. et al. (2011) "CD8+ T Cells in Facioscapulohumeral Muscular Dystrophy Patients with Inflammatory Features at Muscle MRI" *J Clin Immunol*, 31:155-166.
Fukuyo et al., "IL-6-accelerated calcification by induction of ROR2 in human adipose tissue-derived mesenchymal stem cells is STAT3 dependent" *Rheumatology*, 53:1282-1290 (2014).
Furuya et al., "Interleukin-6 as a Potential Therapeutic Target for Pulmonary Arterial Hypertension" *Int. J. Rheumatol.*, 2010:Article ID 720305, doi:10.1155/2010/720305, 8 pages (2010).
Gabay, "Interleukin-6 and chronic inflammation" *Arthritis Research & Therapy*, 8(Suppl 2):S3 (2006).
Gaziano et al., "Multivitamins in the Prevention of Cancer in Men—The Physicians' Health Study II Randomized Controlled Trial" *JAMA* 308(18):1871-1880 (2012) (Corrected 2014).
Gaziano et al., "Relation Between Systemic Hypertension and Blood Lipids on the Risk of Myocardial Infarction" *Am. J. Cardiol.* 84(7):768-773 (1999).

Gehrs et al. (2010) "Complement, age-related macular degeneration and a vision of the future" *Arch. Ophthalmol.* 128(3):349-358. HHS Public Access Author Manuscript; available in PMC Apr. 21, 2015 (21 pages).
Genetics Home Reference (Nov. 1, 2016) "C3 glomerulopathy" [online]. U.S. National Institutes of Health. Retrieved from: https://ghr.nlm.nih.gov/condition/c3-glomerulopathy.
Gerritsen et al., "Flavenoids inhibit cytokine-induced endothelial cell adhesion protein gene expression" *Am. J. Pathol.* 147(2):278-292 (1995).
Gidez et al., "Separation and Quantitation of Subclasses of Human Plasma High Density Lipoproteins by a Simple Precipitation Procedure" *J. Lipid Res.* 23:1206-1223 (1982).
Gilham et al., "RVX-208, a BET-inhibitor for treating atherosclerotic cardiovascular disease, raises ApoA-I/HDL and represses pathways that contribute to cardiovascular disease" *Atherosclerosis* 247:48-57 (2016).
Gordin et al., "Osteopontin is a strong predictor of incipient diabetic nephropathy, cardiovascular disease, and all-cause mortality in patients with type 1 diabetes" *Diabetes Care* 37:2593-2600 (2014).
Gordon et al., "High Density Lipoprotein As a Protective Factor Against Coronary Heart Disease" *Am. J. Med.* 62(5):707-714 (1977).
Gordon et al., "High-density lipoprotein cholesterol and cardiovascular disease. Four prospective American studies" *Circulation* 79:8-15 (1989).
Gosmini et al., "The discovery of I-BET726 (GSK1324726A), a potent tetrahydroquinoline ApoA1 up-regulator and selective BET bromodomain inhibitor" *J. Med. Chem.* 57:8111-8131 (2014).
Grau, "Implications of cytokines in immunopathology: experimental and clinical data" *Eur. Cytokine Netw.*, 1(4):203-210 (1990).
Greene, T.W. and P.G.M. Wuts (Eds.), *Protective Groups in Organic Synthesis*. 3rd ed. John Wiley & Sons., Inc., 1999; pp. 552-559.
Grossman et al., "Interleukin 6 is expressed in high levels in psoriatic skin and stimulates proliferation of cultured human keratinocytes" *Proc. Natl. Acad. Sci. USA* 86:6367-6371 (1989).
Grundy et al., "Assessment of cardiovascular risk by use of multiple-risk-factor assessment equations. A statement for healthcare professionals from the American Heart Association and the American College of Cardiology" *J. Am. Coll. Cardiol.* 34:1348-1359 (1999).
Grundy et al., "Definition of Metabolic Syndrome. Report of the National Heart, Lung and Blood Institute/American Heart Association Conference on Scientific Issues Related to Definition" *Circulation* 109:433-438 (2004).
Gugler et al., "Disposition of Quercetin in Man after Single Oral and Intravenous Doses" *Eur. J. Clin. Pharmacol.* 9:229-234 (1975).
Guillory, J.K., "Generation of Polymorphs, Hydrates, Solvates, and Amorphous Solids" Brittain, Harry G. (ed.) *Polymorphism in Pharmaceutical Solids*, vol. 95. Marcel Dekker, Inc., New York; pp. 202-208 (1999).
Hafiane et al., "HDL, Atherosclerosis, and Emerging Therapies" *Cholesterol* 2013:891403 (2013) (18 pages).
Hakamata et al., "Differential effects of an acyl-coenzyme A: cholesterol acyltransferase inhibitor on HDL-induced cholesterol efflux from rat macrophage foam cells" *FEBS Letters* 363:29-32 (1995).
Haneke, "trans-Resveratrol, [501-36-0], Review of Toxicological Literature" Nat. Inst. Environ. Health Sciences Contract No. N01-ES-65402 (Mar. 2002).
Hazra et al., "New diospyrin derivatives with improved tumour inhibitory activity towards Ehrlich ascites carcinoma" *Medical Science Research* 22(5):351-353 (1994).
Hazra et al., "Synthesis of an antitumor derivative of diospyrin" *IRCS Medical Science* 14(1):35-36 (1986).
He et al., "Local inflammation occurs before systemic inflammation in patients with COPD" *Respirology*, 15:478-484 (2010).
Heeg et al., "Plasma Levels of Probucol in Man after Single and Repeated Oral Doses" *La Nouvelle Presse Medicale* 9:2990-2994 (1980). English abstract on p. 2990.
Heeringa and Cohen (2012) "Kidney diseases caused by complement dysregulation: Acquired, inherited, and still more to come" *Clin. Dev. Immunol.* 2012:Article ID 695131, 6 pages.
Hemingway et al., "A gas-liquid chromatographic examination of stilbene derivatives" *J. Chromatog.* 50(3):391-399 (1970).

(56) References Cited

OTHER PUBLICATIONS

Hertle et al., "The complement system in human cardiometabolic disease" *Mol. Immunol.* 61:135-148 (2014).
Hertog et al., "Dietary Antioxidant Flavonoids and Risk of Coronary Heart Disease: the Zutphen Elderly Study" *Lancet* 342:1007-1011 (1993).
Hidaka et al., "Affinity Purification of the Hepatic High-Density Lipoprotein Receptor Identifies Two Acidic Glycoproteins and Enables Further Characterization of Their Binding Properties" *Biochem. J.* 284:161-167 (1992).
Hietala et al. (2002) "Complement deficiency ameliorates collagen-induced arthritis in mice" *J. Immunol.* 169(1):454-459.
Hill et al., "Thrombosis in paroxysmal nocturnal hemoglobinuria" *Blood*, 121(25):4986-4996 (2013).
Hill, A. et al. (2005) "Sustained response and long-term safety of eculizumab in paroxysmal nocturnal hemoglobinuria" *Blood*, 106:2559-2565.
Hinterseher, I. et al. (2011) "Role of Complement Cascade in Abdominal Aortic Aneurysms" *Arterioscler Thromb Vasc Biol*, 31(7):1653-1660.
Hirano et al., "Biological and clinical aspects of interleukin 6" *Immunol. Today*, 11:443-449 (1990).
Hirano et al., "Excessive production of interleukin 6/B cell stimulatory factor-2 in rheumatoid arthritis" *Eur. J. Immunol.* 18(11):1797-1801 (1988).
Hirano et al., "Genetic Cholesteryl Ester Transfer Protein Deficiency Is Extremely Frequent in the Omagari Area of Japan. Marked Hyperalphalipoproteinemia Caused by CETP Gene Mutation Is Not Associated With Longevity" *Arterioscler Thromb. Vasc. Biol.* 17:1053-1059 (1997).
Hisano et al., "Studies on Organosulfur Compounds. XII. Syntheses and Pharmacological Activities of 2-Heterocyclic Substituted 4(3H)-Quinazolinones" *Chem. Pharm. Bull.* 23(9):1910-1916 (1975).
Höochsmann, B. et al. (2014) "Targeted Therapy with Eculizumab for Inherited CD59 Deficiency" *N Engl J Med*, 370(1):90-92.
Hoekzema et al., "Analysis of Interleukin-6 in Endotoxin-Induced Uveitis" *Invest. Ophthalmol. Vis. Sci.* 32(1):88-95 (1991).
Holland et al. (2004) "Synthetic small-molecule complement inhibitors" *Curr. Opin. Investig. Drugs* 5(11):1164-1173.
Hopkins, "Molecular biology of atherosclerosis" *Physiol. Rev.* 93:1317-1542 (2013).
Hoppensteadt et al., "Dystregulation of Inflammatory and Hemostatic Markers in Sepsis and Suspected Disseminated Intravascular Coagulation" *Clin. Appl. Thromb. Hemost.*, 21(2):120-127 (2015).
Hour, M-J. et al. (2000) "6-Alkylamino- and 2,3-Dihydro-3'-methoxy-2-phenyl-4-quinazolinones and Related Compounds: Their Synthesis, Cytotoxicity, and Inhibition of Tubulin Polymerization" *J. Med. Chem.* 43(23):4479-4487 (2000).
Huang et al., "Synthesis of Isoquinolines by Palladium-Catalyzed Cyclization, Followed by a Heck Reaction" *Tetrahedron Lett.* 43:3557-3560 (2002).
Hughes et al., "Shiga toxin-1 regulation of cytokine production by human proximal tubule cells" *Kidney Intl.*, 54:1093-1106 (1998).
Humbert et al., "Increased Interleukin-I and Interleukin-6 Serum Concentrations in Severe Primary Pulmonary Hypertension" *Am. J. Respir. Crit. Care Med.*, 151:1628-1631 (1995).
Hunziker and Nissen (1926) "Lactose Solubility and Lactose Crystal Formation. I. Lactose Solubility" *J. Dairy Sci.*, 9(6):517-537.
Husten, "Global epidemic of cardiovascular disease predicted" *Lancet* 352:1530 (1998).
Husten, "More data reported for HDL's role in heart disease" *Lancet* 352:1603 (1998).
Hwang et al., "Synergistic inhibition of LDL oxidation by phytoestrogens and ascorbic acid" *Free Radical Biology and Medicine* 29(1):79-89 (Jul. 1, 2000).
Ifergan et al., "Statins Reduce Human Blood-Brain Barrier Permeability and Restrict Leukocyte Migration: Relevance to Multiple Sclerosis" *Ann. Neurol.*, 60:45-55 (2006).

Inman, M. et al. (2015) "Eculizumab-induced reversal of dialysis-dependent kidney failure from C3 glomerulonephritis" *Clinical Kidney Journal*, 8(4):445-448.
International Search Report and Written Opinion issued in International Application No. PCT/CA2004/001818; dated Feb. 28, 2005.
International Search Report and Written Opinion issued in International Application No. PCT/CA2007/000146; dated Oct. 29, 2007.
International Search Report and Written Opinion issued in International Application No. PCT/IB2010/000159; dated Aug. 5, 2010.
International Search Report and Written Opinion issued in International Application No. PCT/IB2010/000826; dated Oct. 12, 2010.
International Search Report and Written Opinion issued in International Application No. PCT/IB2012/002721; dated Mar. 14, 2013.
International Search Report and Written Opinion issued in International Application No. PCT/IB2013/003031; dated May 28, 2014.
International Search Report and Written Opinion issued in International Application No. PCT/IB2014/002546; dated Mar. 13, 2015.
International Search Report and Written Opinion issued in International Application No. PCT/IB2015/002560; dated Mar. 19, 2015.
International Search Report and Written Opinion issued in International Application No. PCT/IB2016/000443; dated Jun. 22, 2016.
International Search Report and Written Opinion issued in International Application No. PCT/US2005/037719; dated Mar. 9, 2007.
International Search Report and Written Opinion issued in International Application No. PCT/US2005/038048; dated Mar. 7, 2007.
International Search Report and Written Opinion issued in International Application No. PCT/US2006/029827; dated Apr. 16, 2007.
International Search Report and Written Opinion issued in International Application No. PCT/US2009/048457; dated Oct. 16, 2009.
International Search Report and Written Opinion issued in International Application No. PCT/US2010/031870; dated Jul. 1, 2010.
Ishibashi et al., "Hypercholesterolemia in Low Density Lipoprotein Receptor Knockout Mice and its Reversal by Adenovirus-Mediated Gene Delivery" *J. Clin. Invest.* 92:883-893 (1993).
Ishibashi et al., "Massive Xanthomatosis and Atherosclerosis in Cholesterol-Fed Low Density Lipoprotein Receptor-Negative Mice" *J. Clin. Invest.* 93:1885-1893 (1994).
Ishihara and Hirano, "Il-6 in autoimmune disease and chronic inflammatory proliferative disease" *Cytokine Growth Factor Rev.*, 13(4-5):357-368 (2002).
Itzen et al., "Brd4 activates P-TEFb for RNA polymerase II CTD phosphorylation" *Nucl. Acids Res.* 42:7577-7590 (2014).
Iwata et al., "The Role of Cytokine in the Lupus Nephritis" *J. Biomed. Biotechnol.*, 2011:Article IDS 594809, doi:10.1155/2011/5948009, 7 pages (2011).
Jafri et al., "Baseline and on-treatment high-density lipoprotein cholesterol and the risk of cancer in randomized controlled trials of lipid-altering therapy" *J Am Coll Cardiol*, 55:2846-2854 (2010).
Jahagirdar et al. (2014) "A novel BET bromodomain inhibitor, RVX-208, shows reduction of atherosclerosis in hyperlipidemic ApoE deficient mice" *Atherosclerosis* 236:91-100.
Japanese Office Action issued in Japanese Patent Application No. 2008-524272, dated Jul. 24, 2012, with English translation.
Jayatilake et al., "Kinase Inhibitors From *Polygonum cuspidatum*" *J. Nat. Prod.* 56:1805-1810 (1993).
Jensen et al., "Serum Lipids and Anthropometric Factors Related to the Prevalence of Intermittent Claudication" *Eur. J. Vasc. Endovasc. Surg.* 30:582-587 (2005).
Jeong et al., "Hypocholesterolemic activity of hesperetin derivatives" *Bioorg. Med. Chem. Lett.* 13:2663-2665 (2003).
Jiang et al. (2011) "Stable knockdown of MYCN by lentivirus-based RNAi inhibits human neuroblastoma cells growth in vitro and in vivo" *Biochem. Biophys. Res. Commun.*, 410:364-370.
Jilka et al., "Increased osteoclast development after estrogen loss: mediation by interleukin-6" *Science*, 257(5066):88-91 (1992).
Jin et al., "Antiplatelet and antithrombotic activities of CP201, a newly synthesized 1,4-naphthoquinone derivative" *Vasc. Pharmacol.* 41(1):35-41 (2004).
Jones, M. et al. (2014) "Evidence for classic complement activity in neuromyelitis optica" *Clin Neuropathol*, 33:251-252, No. 3/2014.
Kalusa et al., "An efficient synthesis of 2,3-diaryl (3H)-quinazolin-4-ones via imidoyl chlorides" *Tetrahedron Letters* 49(41):5840-5842 (2008).

(56) References Cited

OTHER PUBLICATIONS

Kamel et al. "Pharmaceutical significance of cellulose: A review" *eXPRESS Polymer Letters* 2(11):758-778 (2008).
Kaminski, H. et al. (2004) "Complement regulators in extraocular muscle and experimental autoimmune myasthenia gravis" *Experimental Neurology*, 189:333-342.
Kannel et al., "Fibrinogen and risk of cardiovascular disease. The Framingham Study" *JAMA* 258:1183-1186 (1987).
Karpman, D. (2012) "Management of Shiga toxin-associated *Escherichia coli*-induced haemolytic uraemic syndrome: randomized clinical trials are needed" *Nephrol Dial Transplant*, 27:3669-3674.
Kawamatsu et al., "2-Amino-4-Phenylthiazole Derivatives As Anti-Atherogenic Agents" *Eur. J. Med. Chem.—Chimica Therapeutica* 16(4):355-362 (1981).
Kawauchi et al. (2012) "A mouse model of the most aggressive subgroup of human medulloblastoma" *Cancer Cell*, 21:168-180.
Kayikcioglu et al., "Benefits of statin treatment in cardiac syndrome-$X^1$" *Eur. Heart. J.*, 24:1999-2005 (2003).
Keel and Trentz (2005) "Pathophysiology of polytrauma" *Injury* 36(6): 691-709.
Kempen et al., "Stimulation of Hepatic Apolipoprotein A-I Production by Novel Thieno-Triazolodiazepines: Roles of the Classical Benzodiazepine Receptor, PAF Receptor, and Bromodomain Binding" *Lipid Insights* 6:47-54 (2013).
Kerr et al., "Review. Interleukin 6 and Haemostasis" *Br. J. Haematol.*, 115:3-12 (2001).
Khera et al., "Cholesterol efflux capacity, high-density lipoprotein function, and atherosclerosis" *N. Engl. J. Med.*, 364:127-135 (2011).
Khetani et al, "Microscale culture of human liver cells for drug development" *Nat Biotechnol* 26:120-126 (2008).
Kilbourne et al., "Involvement of Early Growth Response Factor Egr-1 in Apolipoprotein Al Gene Transcription" *J. Biol. Chem.* 270:7004-7010 (1995).
Kim et al., "Hypothetical Drug Binding Receptor Site Analysis Using CoMFA Method for 3-Arylisoquinolines Active Against SK-OV-3 Tumor Cell Line" *Yakhak Hoechi* 46(4):219-225 (2002). English abstract on p. 219.
Kishimoto and Hirano., "Molecular regulation of B lymphocyte response" *Ann. Rev. Immunol.*, 6:485-512 (1988).
Kishimoto, "The biology of interleukin-6" *Blood*, 74:1-10 (1989).
Kita et al., "Daily Serum Interleukin-6 Monitoring in Multiple Organ Transplantation With or Without Liver Allografts" *Transplant. Proc.*, 28(3):1229-1234 (1996).
Klein et al. (1991) "Murine anti-interleukin-6 monoclonal antibody therapy for a patient with plasma cell leukemia" *Blood*, 78:1198-1204.
Klein et al. (2005) "Complement factor H polymorphism in age-related macular degeneration" *Science* 308(5720):385-389. NIH Public Access Author Manuscript; available in PMC Jul. 18, 2006 (12 pages).
Kobayashi et al., "Regulation mechanism of ABCA1 expression by statins in hepatocytes" *Eur. J. Pharmacol.* 662:9-14 (2011).
Koch et al, "Angiogenesis mediated by soluble forms of E-selectin and vascular cell adhesion molecule-1" *Nature*, 376:517-519 (1995).
Koch et al., "Immunolocalization of endothelial and leukocyte adhesion molecules in human rheumatoid and osteoarthritic synovial tissues" *Lab. Invest.*, 64:313-322 (1991).
Kostis and Dobrzynski, "The Effect of Statins on Erectile Dysfunction: A Meta-Analysis of Randomized Trials" *J. Sex Med.*, 11:1626-1635 (2014).
Koudinov et al., "Alzheimer's amyloid beta and lipid metabolism: a missing link?" *FASEB J.* 12:1097-1099 (1998).
Kublak et al., "The preparation of the aza-spirobicyclic system of discorhabdin C via an intramolecular phenolate alkylation" *Tetrahedron Lett.* 31(27):3845-3848 (1990).
Kukielka et al., "Interleukin-8 Gene Induction in the Myocardium after Ischemia and Reperfusion In Vivo" *J. Clin. Invest.*, 95:89-103 (1995).
Kulkarni et al., "Quantification of $HDL_2$ and $HDL_3$ Cholesterol by the Vertical Auto Profile-II (VAP-II) Methodology" *J. Lipid Res.* 38:2353-2364 (1997).
Kurata et al., "A Candidate High Density Lipoprotein (HDL) Receptor, $HB_2$, with Possible Multiple Functions Shows Sequence Homology with Adhesion Molecules" *J. Atheroscler Thromb.* 4:112-117 (1998).
Kuroda, H. et al. (2013) "Increase of complement fragment C5a in cerebrospinal fluid during exacerbation of neuromyelitis optica" *J Neuroimmunol*, 254:178-182.
Kurowska et al., "Essential Amino Acids in Relation to Hypercholesterolemia Induced in Rabbits by Dietary Casein" *J. Nutr.* 120:831-836 (1990).
Kurzrock, R. et al. (1993) "Serum Interleukin 6 Levels Are Elevated in Lymphoma Patients and Correlate with Survival in Advanced Hodgkin's Disease and with B Symptoms" *Cancer Research*, 53:2118-2122.
Kuwahata et al., "High expression level of Toll-like receptor 2 on monocytes is an important risk factor for arteriosclerotic disease" *Atherosclerosis* 209:248-254 (2010).
Kuzuya et al., "Probucol Prevents Oxidative Injury to Endothelial Cells" *J. Lipid Res.* 32:197-204 (1991).
Laarhoven et al., "Syntheses, infrared spectra and molecular refractions of some sterically hindered p,p'-dimethoxystilbenes. Influence of non-planarity in styrene and stilbene derivatives IV" *Recueil des Travaux Chimiques des Pays-Bas* 80:775-791 (1961).
Lagrost et al., "Opposite Effects of Cholesteryl Ester Transfer Protein and Phospholipid Transfer Protein on the Size Distribution of Plasma High Density Lipoproteins" *J. Biol. Chem.* 271:19058-19065 (1996).
Lambertsen et al., "Inflammatory cytokines in experimental and human stroke" *J. Cerebral Blood Flow & Metabol.*, 32:1677-1698 (2012).
Lamon-Fava, "Genistein activates apolipoprotein A-I gene expression in the human hepatoma cell line Hep G2" *J. Nutrition* 130:2489-2492 (2000).
Lamotte et al. (2012) "Identification of a novel series of BET family Bromodomain inhibitors: binding mode and profile of I-BET151 (GSK1210151A)" *Bioorg Med Chem Lett*, Accepted manuscript, doi: 10.1016/j.bmcl.2012.02.041 (14 pages). Final publication in 22(8):2968-2972.
Landi et al., "HDL-cholesterol and physical performance: results from the ageing and longevity study in the sirente geographic area (ilSirente Study)" *Age and Ageing*, 36(5):514-520 (2007).
Landshulz et al., "Regulation of Scavenger Receptor, Class B, Type I, a High Density Lipoprotein Receptor, in Liver and Steroidogenic Tissues of the Rat" *J. Clin. Invest.* 98:984-995 (1996).
Lapeyraque, A. (2011) "Eculizumab in Severe Shiga-Toxin—Associated Hus" *N Engl J Med*, 364(26):2561-2563.
Larach et al., "Targeting high density lipoproteins in the prevention of cardiovascular disease?" *Curr. Cardiol. Rep.* 14:684-691 (2012). NIH Public Access Author Manuscript, available in PMC Dec. 1, 2013 (12 pages).
Lechner, J. et al. (2016) "Higher plasma levels of complement C3a, C4a and C5a increase the risk of subretinal fibrosis in neovascular age-related macular degeneration" *Immunity & Ageing*, 13(4):1-9.
Lee and Parks, "ATP-binding cassette transporter Al and its role in HDL formation" *Curr. Opin. Lipidol.* 16:1925 (2005).
Lefer et al., "Vascular effects of HMG CoA-reductase inhibitors (statins) unrelated to cholesterol lowering: new concepts for cardiovascular disease" *Cardiovasc. Res.*, 49:281-287 (2001).
Lefkowitz, D.L. and S.S. Lefkowitz (2005) "Fascioscapulohumeral muscular dystrophy: A progressive degenerative disease that responds to diltiazem" *Medical Hypotheses*, 65:716-721.
Legendre, C. et al. (2013) "Terminal Complement Inhibitor Eculizumab in Atypical Hemolytic—Uremic Syndrome" *N Engl J Med*, 368(23):2169-2181.
Leszczynska and Mesquida, "IL-6 Receptor Antagonist: Tocilizumab" in *Advances in the Treatment of Noninfectious Uveitis with Biologics: Anti-TNF and Beyond*. Marina Mesquida (Ed.), OMICS Group eBooks, Foster City, CA, 2014; 9 pages [online]. www.esciencecentral.org/ebooks.

(56) References Cited

OTHER PUBLICATIONS

Letan, "The Relation of Structure to Antioxidant Activity of Quercetin and some of Its Derivatives. I. Primary Activity" *J. Food Sci.* 13(4):518-523 (1966).

Libby et al., "Inflammation and Atherosclerosis" *Circulation* 105:1135-1143 (2002).

Libby, "The Forgotten Majority: Unfinished Business in Cardiovascular Risk Reduction" *J. Am. Coll. Cardiol.* 46(7):1225-1228 (2005).

Liebman and Feinstein (2003) "Thrombosis in patients with paroxysmal nocturnal hemoglobinuria is associated with markedly elevated plasma levels of leukocyte-derived tissue factor" *Thromb. Res.* 111(4-5):235-238.

Lim, W. (2011) "Complement and the antiphospholipid syndrome" *Current Opinion in Hematology*, 18:361-365.

Lin et al., "Chemoprevention of Cancer and Cardiovascular Disease by Resveratrol" *Proc. Natl. Sci. Counc. Roc (B)* 23:99-106 (1999).

Lin et al., "Potential bioreductive alkylating agents. 7. Antitumor effects of phenyl-substituted 2-chloromethyl-3-phenyl-1,4-naphthoquinones" *J. Med. Chem.* 19(11):1336-1338 (1976).

Lin et al., "Solvent Effects on Aza-Anionic Cycloaromatization of 2-(2-Substituted-Ethynyl)Benzonitriles" *J. Chinese Chem. Soc.* 48:211-214 (2001).

Lin et al., "The Role of Absorption, Distribution, Metabolism, Excretion and Toxicity in Drug Recovery" *Curr. Top. Med. Chem.* 3:1125-1154 (2003).

Linnell et al. "Isomers of stilbestrol. II." *Q. J. Pharm. Pharmacol.* 15:384-388 (1942).

Lipo, E. et al. (2013) "Aurintricarboxylic Acid Inhibits Complement Activation, Membrane Attack Complex, and Choroidal Neovascularization in a Model of Macular Degeneration" *Investigative Ophthalmology & Visual Science*, 54(10):7107-7114.

Litalien et al., "Circulating inflammatory cytokine levels in hemolytic uremic syndrome" *Pediatr. Nephrol.*, 13:840-845 (1999).

Liu, F. et al. (2011) "The Role of Complement in the Pathogenesis of Artery Aneurysms" *Etiology, Pathogenesis and Pathophysiology of Aortic Aneurysms and Aneurysm Rupture*, [online]. Downloaded from: http://www.intechopen.com/books/etiology-pathogenesis-andpathophysiology-of-aortic-aneurysms-and-aneurysm-rupture, ISBN 978-953-307-523-5, InTech.

Lonze, B. et al. (2010) "Eculizumab and Renal Transplantation in a Patient with CAPS" *N Engl J Med*, 362(18):1744-1745.

Lopez et al., "The Synthesis of Substituted 2-Aryl-4(3H)-quinazolinones using NaHSO₃/DMA. Steric Effect Upon the Cyclisation-Dehydrogenation Step" *J. Chem. Research (S)*, pp. 258-259 (2000).

Lowenstein and Matsushita, "The acute phase response and atherosclerosis" *Drug Discovery Today: Disease Mechanisms* 1:17-22 (2004).

Lucchinetti, C. et al. (2002) "A role for humoral mechanisms in the pathogenesis of Devic's neuromyelitis optica" *Brain*, 125:1450-1461.

Maher et al., "Lipoprotein (a) and coronary heart disease" *Curr. Opin. Lipidol.* 6:229-235 (1995).

Mahto et al., "Synthesis of 3-Aryl-7-Hydroxy Isochromenes" *Asian J. Chem.* 11(2):431-435 (1999).

Malik et al. (2012) "A hybrid CFHR3-1 gene causes familial C3 glomerulopathy" *J. Am. Soc. Nephrol.* 23(7):1155-1160.

Mammen, A.L. and V. Sartorelli (2015) "IL-6 Blockade as a Therapeutic Approach for Duchenne Muscular Dystrophy" *EBioMedicine*, 2:274-275.

Manach et al., "Polyphenols and prevention of cardiovascular diseases" *Curr. Opin. Lipidol.* 16:77-84 (2005).

Mantovani, S. et al. (2014) "Elevation of the terminal complement activation products C5a and C5b-9 in ALS patient blood" *Journal of Neuroimmunology*, 276:213-218.

Markiewski et al. (2007) "Complement and coagulation: strangers or partners in crime?" *Trends Immunol.* 28(4):184-192.

Marks, F., "Epidermal Growth Control Mechanisms, Hyperplasia, and Tumor Promotion in the Skin" *Cancer Res.* 36:2636-2343 (1976).

Martin et al., "Modified Flavinoids As Strong Photoprotecting UV-Absorbers and Antioxidants" *Strategies for Safe Food*. Eklund, T. et al. (Eds.), vol. 1, pp. 288-291 (2003).

Mazzone et al., "Cardiovascular disease risk in type 2 diabetes mellitus: insights from mechanistic studies" *Lancet* 371(9626): 1800-1809 (2008).

McCaughan, J.A. et al. (2012) "Recurrent Dense Deposit Disease After Renal Transplantation: An Emerging Role for Complementary Therapies" *American Journal of Transplantation*, 12:1046-1051.

McFarlane et al., "Pleiotropic Effects of Statins: Lipid Reduction and Beyond" *J. Clin. Endocrinol. Metab.*, 87:1451-1458 (2002).

McGrowder et al., "The role of high density lipoproteins in reducing the risk of vascular diseases, neurogenerative disorders, and cancer" *Cholesterol*, 2011, Article 496925, 9 pages.

McKee et al., "Some Basically Substituted Quinazolines" *J. Am. Chem. Soc.* 68(10):1902-1903 (1946).

McLure et al., "RVX-208, an Inducer of ApoA-I in Humans, Is a BET Bromodomain Antagonist" *PLOS One*, 8(12):e83190 (2013) (12 pages).

Meckes et al., "The effects of chrysin and pinostrobin, 2 flavonoids isolated from *Teloxys graveolens* leaves, on isolated guinea-pig ileum" *Phytomedicine* 5(6):459-463 (1998).

Melani et al., "Tricyclic heterocyclic systems: pyrazolo[5',4':4,5]- and pyrazolo-[3',4':4,5]pyrano[2,3-B]pyridine derivatives" *J. Heterocyclic Chem.* 25:1367-1371 (1988).

Merriam-Webster Dictionary, "Prevention" Definition [online]. Retrieved from: http://www.merriam-webster.com/dictionary/prevention, on Oct. 19, 2016 (1 page).

Mertz et al. (2011) "Targeting MYC dependence in cancer by inhibiting BET bromodomains" *Proc Natl Acad Sci USA*, 108(40):16669-16674.

Messina, S. et al. (2011) "Activation of NF-kB pathway in Duchenne muscular dystrophy: relation to age" *Acta Myol*, 30(1):16-23.

Middleton et al., "Quercetin inhibits lipopolysaccharide-induced expression of endothelial cell intracellular adhesion molecule-1" *Int. Arch. Allergy Immunol.* 107:435-436 (1995).

Millán et al., "Lipoprotein ratios: Physiological significance and clinical usefulness in cardiovascular prevention" *Vascular Health and Risk Management*, 5:757-765 (2009).

Mills, "Pharmaceutical excipients—an overview including considerations for paediatric dosing" Presented at the World Health Organization Training Workshop: Pharmaceutical Development with Focus on Paediatric Formulations, Beijing, China, Jun. 21-25, 2010; pp. 1, 3, 10, and 13.

Minoretti et al., "Prognostic significance of plasma osteopontin levels in patients with chronic stable angina" *Eur. Heart J.* 27:802-807 (2006).

Mirguet et al., "From ApoA1 upregulation to BET family bromodomain inhibition: Discovery of I-BET151" Article in Press, *Bioorg. Med. Chem. Lett.*, doi:10.1016/j.bmcl.2012.01.125 (Feb. 8, 2012) (5 pages.) Final publication in 22:2963-2967 (Apr. 15, 2012).

Mitchell et al., "Bromination of 4,6-dimethoxyindoles" *Tetrahedron* 68(39):8163-8171 (2012).

Miyazaki, et al. "Intravenous Injection of Rabbit Apolipoprotein A-I Inhibits the Progression of Atherosclerosis in Cholesterol-Fed Rabbits," *Arterioscler. Thromb. Vasc. Biol.* 15: 1882-1888 (1995).

Mizutani, Y. et al. (1995) "Sensitization of Human Renal Cell Carcinoma Cells to cis-Diamminedichloroplatinum(II) by Anti-Interleukin 6 Monoclonal Antibody or Anti-Interleukin 6 Receptor Monoclonal Antibody" *Cancer Research*, 55:590-596.

Moffett, "Azacoumarins" *J. Org. Chem.* 35(11):3596-3600 (1970).

Molnár and Balázs, "High Circulating IL-6 Level in Graves' Ophthalmopathy" *Autoimmunity*, 25:91-96 (1997).

Mondal et al., "Two-Stage Chemical Oncogenesis in Cultures of C3H/10T1/2 Cells" *Cancer Res*, 36:2254-2260 (1976).

Morales-Ducret et al., "α4/β1 integrin (VLA-4) ligands in arthritis. Vascular cell adhesion molecule-1 expression in synovium and on fibroblast-like synoviocytes" *J. Immunol.* 149:1424-1431 (1992).

Moreau et al., "Elevated IL-6 and TNF-α levels in patients with ALS: Inflammation or hypoxia?" *Neurology*, 65:1958-1960 (2005).

(56) References Cited

OTHER PUBLICATIONS

Morgan and Harris, "Complement, a target for therapy in inflammatory and degenerative diseases" *Nat. Rev. Drug Disc.* 14:857-877 (2015).
Mozaffarian et al., "Heart disease and stroke statistics—2015 update. A report from the American Heart Association" *Circulation* 131:e29-e322 (2015).
Muller et al. "Bromodomains as therapeutic targets" *Expert Rev. Mol. Med.* 13:e29 (2011).
Murphy, B. et al. (2002) "Factor H—Related Protein-5: A Novel Component of Human Glomerular Immune Deposits" *American Journal of Kidney Diseases*, 39(1):24-27.
Murray and Lopez, "Mortality by cause for eight regions of the world: Global Burden of Disease Study" *Lancet* 349:1269-1276 (1997).
Muscari et al. (1988) "Association of serum IgA and C4 with severe atherosclerosis" *Atherosclerosis* 74(1-2):179-186.
Muscari et al. (1995) "Association of serum C3 levels with the risk of myocardial infarction" *Am. J. Med.* 98(4):357-364.
Musselman et al., "Higher than normal plasma interleukin-6 concentrations in cancer patients with depression: preliminary findings" *Am. J. Psychiatry*, 158:1252-1257 (2001).
Naden, C., "Methaqualone" in *The Facts About the A-Z of Drugs*. Tarrytown, NY: Marshall Cavendish Benchmark, 2008; pp. 92-94.
Nagasaki, T. et al. (2014) "Interleukin-6 released by colon cancer-associated fibroblasts is critical for tumour angiogenesis: anti-interleukin-6 receptor antibody suppressed angiogenesis and inhibited tumour—stroma interaction" *Br J Cancer*, 110:469-478.
Nakagiri et al., "Immunology Mini-review: The Basics of $T_H17$ and Interleukin-6 in Transplantation" *Transplantation Proceedings*, 44:1035-1040 (2012).
Naughton et al. "A stereotypic, transplantable liver tissue-culture system" *Appl. Biochem. Biotechnol.* 54:65-91 (1995).
Naughton et al., "Stereotypic culture systems for liver and bone marrow: Evidence for the development of functional tissue in vitro and following implantation in vivo" *Biotechnol. Bioeng*, 43:810-825 (1994).
Navab et al., "Apolipoprotein A-I Mimetic Peptides" *Arterioscler Thromb. Vasc. Biol.* 25:1325-1331 (2005).
Navab et al., "HDL and cardiovascular disease: atherogenic and atheroprotective mechanisms" *Nat. Rev. Cardiol.* 8:222-232 (2011).
Nayer, A. et al. (2014) "Catastrophic antiphospholipid syndrome: a clinical review" *Journal of Nephropathology*, 3(1):9-17.
Neurath and Finotto, "IL-6 signaling in autoimmunity, chronic inflammation and inflammation-associated cancer" *Cytokine & Growth Factor Reviews* 22:83-89 (2011).
Neves et al., "Anemia and Interleukin-6 Are Associated with Faster Progression to End-Stage Renal Disease" *Dialysis & Transplantation* 36(8):445-456 (2007).
New et al., "Calcific Uremic Arteriolopathy in Peritoneal Dialysis Populations" *Int. J. Nephrol.*, 2011:Article ID 982854, doi:10.4061/2011/982854, 9 pages (2011).
Nicholls et al. (2006) "Relationship Between Cardiovascular Risk Factors and Atherosclerotic Disease Burden Measured by Intravascular Ultrasound" *J. Am. Coll. Cardiol.* 47(10):1967-1975.
Nicholls et al. (2007) "Statins, High-Density Lipoprotein Cholesterol, and Regression of Coronary Atherosclerosis" *JAMA* 297(5):499-508 (2007).
Nicholls et al. (2011) "Effect of Two Intensive Statin Regimens on Progression of Coronary Disease" *N. Engl. J. Med.* 365:2078-2087.
Nicholls et al. (2011) "Efficacy and Safety of a Novel Oral Inducer of Apolipoprotein A-I Synthesis in Statin-Treated Patients with Stable Coronary Artery Disease" *J. Am. Coll. Cardiol.* 57(9):1111-1119.
Nicholls et al. (2012) "ApoA-I induction as a potential cardioprotective strategy: Rationale for the SUSTAIN and ASSURE studies" *Cardiovasc. Drugs Ther.* 26:181-187.
Nicodeme et al., "Suppression of inflammation by a synthetic histone mimic" *Nature* 468:1119-1123 (2010).
Nigam et al., "Synthesis and Pharmacological Screening of Some New 2-(Phenyl/Chloromethyl)-3-[4 (N, N-Disubstituted Aminocarbonyl) Phenyl]-8-Substituted-4 (3H)-Quinazolones" *Indian Drugs* 27(4):238-243 (1990).
Nissen et al., "Effect of Intensive Compared with Moderate Lipid-Lowering Therapy on Progression of Coronary Atherosclerosis: A Randomized Controlled Trial" *JAMA* 291(9):1071-1080 (2004).
Nissen et al., "Effect of Recombinant ApoA-I Milano on Coronary Atherosclerosis in Patients with Acute Coronary Syndroms: A Randomized Controlled Trial" *JAMA* 290(17):2292-2300 (2003).
Nissen et al., "Effect of Very High-Intensity Statin Therapy on Regression of Coronary Atherosclerosis: The Asteroid Trial" *JAMA* 295(13):1556-1565 (2006).
Noris and Remuzzi (2009) "Atypical hemolytic-uremic syndrome" *N. Engl. J. Med.* 361(17):1676-1687.
Nourooz-Zadeh, "Ferrous Ion Oxidation in Presence of Xylenol Orange for Detection of Lipid Hydroperoxides in Plasma" *Methods Enzymol.* 300:58-62 (1999).
Nozaki, M. et al. (2006) "Drusen complement components C3a and C5a promote choroidal neovascularization" *Proceedings of the National Academy of Sciences USA*, 103(7):2328-2333.
Nytrova, P. et al. (2014) "Complement activation in patients with neuromyelitis optica" *Journal of Neuroimmunology*, 274:185-191.
O'Brien et al., "Interleukin-18 as a therapeutic target in acute myocardial infarction and heart failure" *Mol. Med.* 20:221-229 (2014).
Office Action dated Sep. 20, 2016 in Russian Patent Application No. 2014115427/15(024178), filed Oct. 31, 2012, by Resverlogix Corp., CA: (English translation, 7 pages).
Ogata et al. (1989) "Sequence of the gene for murine complement component C4" *J. Biol. Chem.* 264(28):16565-16572.
Ohkawara et al., "In situ expression of the cell adhesion molecules in bronchial tissues from asthmatics with air flow limitation: in vivo evidence of VCAM-1/VLA-4 interaction in selective eosinophil infiltration" *Am. J. Respir. Cell Mol. Biol.*, 12:4-12 (1995).
Ohta et al., "Detection and clinical usefulness of urinary interleukin-6 in the diseases of the kidney and the urinary tract" *Clin. Nephrol.*, 38(4):185-189 (1992).
Ohtomo et al., "Comparative activities of daidzein metabolites, equol and O-desmethylangolensin, on bone mineral density and lipid metabolism in ovariectomixed mice and in osteoclast cell cultures" *Eur. J. Nutr.* 47(5):273-279 (2008).
Okroj et al. (2007) "Rheumatoid arthritis and the complement system" *Ann. Med.* 39(7):517-530.
Oku, K. et al. (2009) "Complement activation in patients with primary antiphospholipid syndrome" *Annals of the Rheumatic Diseases*, 68:1030-1035.
Ono et al., "Increased interleukin-6 of skin and serum in amyotrophic lateral sclerosis" *J. Neurol. Sci.*, 187:27-34 (2001).
Ordovas, J.M., "Gene-diet interaction and plasma lipid responses to dietary intervention" *Biochem. Soc. Trans.* 30(2):68-73 (2002).
Orosz et al., "Role of the endothelial adhesion molecule VCAM in murine cardiac allograft rejection" *Immunol. Lett.*, 32(1):7-12 (1992).
Orth, D. et al. (2009) "Shiga Toxin Activates Complement and Binds Factor H: Evidence for an Active Role of Complement in Hemolytic Uremic Syndrome" *Journal of Immunology*, 182:6394-6400.
Park et al., "Serum biomarkers for neurofibromatosis type 1 and early detection of malignant peripheral nerve-sheath tumors" *BMC Med.*, 11:109, 9 pages (2013).
Parra et al., "A Case-Control Study of Lipoprotein Particles in Two Populations at Contrasting Risk for Coronary Heart Disease" *Arterioscler Thromb.* 12:701-707 (1992).
Patani et al., "Bioisosterism: A Rational Approach in Drug Design" *Chem. Rev.* 96(8):3147-3176 (1996).
Pearson et al., "The ortho Bromination of Phenols" *J. Org. Chem.* 32:2358-2360 (1967).
Pecoits-Filho et al., "Interleukin-6 is an independent predictor of mortality in patients starting dialysis treatment" *Nephrol. Dial. Transplant.*, 17:1684-1688 (2002).
Pecoits-Filho et al., "Updated on interleukin-6 and its role in chronic renal failure" *Nephrol. Dial. Transplant.*, 18:1042-1045 (2003).

(56) References Cited

OTHER PUBLICATIONS

Pei et al. (2012) "An Animal Model of MYC-Driven Medulloblastoma" *Cancer Cell*, 21:155-167.
Pelosi, L. et al. (2015) "Functional and Morphological Improvement of Dystrophic Muscle by IL6 Receptor Blockade" *EBioMedicine*, 2:285-293.
Peng et al. (2005) "Role of C5 in the development of airway inflammation, airway hyperresponsiveness, and ongoing airway response" *J. Clin. Invest.* 115(6):1590-1600.
Perez-Villa et al., "Elevated Levels of Serum Interleukin-6 Are Associated With Low Grade Cellular Rejection in Patients With Heart Transplantation" *Transplant. Proc.* 38:3012-3015 (2006).
Pettit et al., "Antineoplastic Agents. 465. Structural Modification of Resveratrol: Sodium Resverastatin Phosphate" *J. Med. Chem.* 45:2534-2542 (2002).
Phuan, P. et al. (2013) "C1q-targeted monoclonal antibody prevents complement-dependent cytotoxicity and neuropathology in in vitro and mouse models of neuromyelitis optica" *Acta Neuropathologica*, 125(6):829-840.
Picaud et al., "RVX-208, an inhibitor of BET transcriptional regulators with selectivity for the second bromodomain" *Proc Natl Acad Sci USA* 110:19754-19759 (2013).
Pickering, M. et al. (2006) "Prevention of C5 activation ameliorates spontaneous and experimental glomerulonephritis in factor H-deficient mice" *Proceedings of the National Academy of Sciences USA*, 103(25):9649-9654.
Pickering, M. et al. (2011) "Complement and glomerular disease: new insights" *Current Opinion in Nephrology and Hypertension*, 20:271-277.
Pickering, M. et al. (2013) "C3 glomerulopathy: consensus report" *Kidney International*, 84:1079-1089.
Pilewski et al., "Cell adhesion molecules in asthma: homing, activation, and airway remodeling" *Am. J. Respir. Cell Mol. Biol.*, 12:1-3 (1995).
Pittock, S. et al. (2013) "Eculizumab in AQP4-IgG-positive relapsing neuromyelitis optica spectrum disorders: an open-label pilot study" *Lancet Neurology*, 12:554-562.
Plump et al., "Human apolipoprotein A-I gene expression increases high density lipoprotein and suppresses atherosclerosis in the apolipoprotein E-deficient mouse" *Proc. Natl. Acad. Sci. USA* 91:9607-9611 (1994).
Prinjha et al. (2012) "Place your BETs: the therapeutic potential of bromodomains" *Trends Pharmacol Sci*, 33(3):146-153.
Puri et al., "Effects of an apolipoprotein A-1 inducer on progression of coronary atherosclerosis and cardiovascular events in patients with elevated inflammatory markers" *J. Am. Coll. Cardiol.* 63:S0735-1097 (2014).
Qiu and Hill, "Atorvastatin Inhibits ABCA1 Expression and Cholesterol Efflux in THP-1 Macrophages by an LXR-dependent Pathway" *Cardiovasc. Pharmacol.* 51: 388-395 (2008).
Quinones et al., "The egr-1 gene is induced by DNA-damaging agents and non-genotoxic drugs in both normal and neoplastic human cells" *Life Sciences* 72(26):2975-2992 (2003).
Quintanilla et al., "Interleukin-6 induces Alzheimer-type phosphorylation of tau protein by deregulating the cdk5/p35 pathway" *Exp. Cell Res.*, 295:245-257 (2004).
Rabb et al., "The role of the leukocyte adhesion molecules VLA-4, LFA-1, and Mac-1 in allergic airway responses in the rat" *Am. J. Respir. Care Med.*, 149:1186-1191 (1994).
Ragione et al., "Antioxidants induce different phenotypes by a distinct modulation of signal transduction" *FEBS Letters* 523:289-294 (2002).
Ragione et al., "p21$^{CIP}$1 Gene Expression Is Modulated by Egr1: A Novel Regulatory Mechanism Involved in the Resveratrol Antiproliferative Effect" *J. Biol. Chem.* 278:23360-23368 (2003).
Rajakumar et al., "TiCl$_4$, Dioxane—A facile and efficient system for de-O-benzylation, de-O-allylation, and de-O-xylylation of phenolic ethers" *Synthetic Communications* 33(22):3891-3896 (2003).
Reitz et al., "Association of higher levels of high-density lipoprotein cholesterol in elderly individuals and lower risk of late-onset Alzheimer Disease" *Arch Neurol*, 67(12):1491-1497 (2010).
Resverlogix Corp. (Nov. 29, 2010) "Successful ASSERT Trial Results in Resverlogix Filing New RVX-208 Patent" News Release [online]. Retrieved from: http://www.resverlogix.com/media/press-release.html?article=30026#.WH8uSnrZRAM, on Jan. 18, 2017 (2 pages).
Resverlogix Corp. (Sep. 1, 2011) "Resverlogix Presents Two Abstracts on Analysis of the Phase 2 ASSERT Clinical Trial at the ESC Congress 2011" News Release [online]. Retrieved from: http://www.resverlogix.com/media/press-release.html?article=55966#.WH8sGnrZRAN, on Jan. 18, 2017 (2 pages).
Resverlogix Corp. (Aug. 28, 2012) "Resverlogix's BET Protein Inhibitor RVX-208 Meets Primary Endpoint in SUSTAIN Clinical Trial in Patients With High Risk Cardiovascular Disease" News Release [online]. Retrieved from: http://www.resverlogix.com/media/press-release.html?id=475#.WHiF_XrZRAM, on Jan. 13, 2017 (2 pages).
Resverlogix Corp. (Sep. 3, 2013) "Further Analysis of the ASSURE Data Finds a Responder Group for RVX-208 With Statistically Significant Regression of Coronary Atherosclerosis" News Release [online]. Retrieved from: http://www.resverlogix.com/media/press-release.html?article=134163#.WHiHP3rZRAM, on Jan. 13, 2017 (3 pages).
Reynolds, R. et al. (2009) "Plasma Complement Components and Activation Fragments: Associations with Age-Related Macular Degeneration Genotypes and Phenotypes" *Investigative Ophthalmology & Visual Science*, 50(12):5818-5827.
Rice-Evans, "Flavonoids and Isoflavones: Absorption, Metabolism, and Bioactivity" *Free Radical Biol. Med.* 36:827-828 (2004).
Ricklin and Lambris (2007) "Complement-targeted therapeutics" *Nat. Biotechnol.* 25(11):1265-1275.
Ricklin and Lambris (2013) "Progress and Trends in Complement Therapeutics" *Adv. Exp. Med. Biol.* 735:1-22. NIH Public Access Author Manuscript; available in PMC Jul. 1, 2013 (28 pages).
Ricklin et al. (2010) "Complement—a key system for immune surveillance and homeostasis" *Nat. Immunol.* 11(9):785-797. NIH Public Access Author Manuscript; available in PMC Sep. 1, 2011 (30 pages).
Rigotti et al., "Regulation by Adrenocorticotropic Hormone of the in Vivo Expression of Scavenger Receptor Class B Type I (SR-BI), a High Density Lipoprotein Receptor, in Steroidogenic Cells of the Murine Adrenal Gland" *J. Biol. Chem.* 271:33545-33549 (1996).
Rimando et al., "Pterostilbene, a New Agonist for the Peroxisome Proliferator-Activated Receptor α-Isoform, Lowers Plasma Lipoproteins and Cholesterol in Hypocholesterolemic Hamsters" *Journal of Agricultural and Food Chemistry* 53(9):3403-3407 (2005).
Rincon and Irvin, "Role of IL-6 in Asthma and Other Inflammatory Pulmonary Diseases" *Int. J. Biol.*, 8:1281-1290 (2012).
Risitano, A. et al. (2016) "Therapeutic complement inhibition in complement-mediated hemolytic anemias: Past, present and future" *Seminars in Immunology*, 28:223-240.
Rodriguez et al., "Novel Effects of the Acyl-Coenzyme A: Cholesterol Acyltransferase Inhibitor 58-035 on Foam Cell Development in Primary Human Monocyte-Derived Macrophages" *Arterioscler. Thromb. Vasc. Biol.* 19:2199-2206 (1999).
Roemer, S. et al. (2007) "Pattern-specific loss of aquaporin-4 immunoreactivity distinguishes neuromyelitis optica from multiple sclerosis" *Brain*, 130:1194-1205.
Rohatgi et al., "HDL Cholesterol Efflux Capacity and Incident Cardiovascular Events" *N. Engl. J. Med.* 371:2383-2393 (2014).
Roodman et al., "Interleukin 6. A potential autocrine/paracrine factor in Paget's disease of bone" *J. Clin. Invest.*, 89:46-52 (1992).
Roos, A. et al. (2006) Glomerular Activation of the Lectin Pathway of Complement in IgA Nephropathy Is Associated with More Severe Renal Disease *Journal of the American Society of Nephrology*, 17:1724-1734.
Rose et al., "Oxygen Heterocycles. XIII. From 3-Arylisocoumarins to 3-Arylisoquinolines and 4-Aryl-5H-2,3-Benzodiazepines" *J. Chem. Soc. [Section ] C: Organic* 17:2205-2208 (1968).

(56) References Cited

OTHER PUBLICATIONS

Rose-John and Schooltink, "Cytokines Are a Therapeutic Target for the Prevention of Inflammation-Induced Cancers" *Recent Results in Cancer Research* 174:57-66 (2007).
Rose-John et al., "The IL-6/sIL-6R complex as a novel target for therapeutic approaches" *Expert Opin. Ther. Targets* 11(5):613-624 (2007).
Rosenblad, T. et al. (2014) "Eculizumab treatment for rescue of renal function in IgA nephropathy" *Pediatric Nephrology*, 29:2225-2228.
Rossi et al., "Optimizing the use of anti-interleukin-6 monoclonal antibody with dexamethasone and 140 mg/m2 of melphalan in multiple myeloma: results of a pilot study including biological aspects" *Bone Marrow Transplantation*, 36:771-779 (2005).
Röth et al. (2009) "Long-term efficacy of the complement inhibitor eculizumab in cold agglutinin disease" *Blood* 113(16):3885-3886.
Rowe, R.C. et al. (Eds.) *Handbook of Pharmaceutical Excipients*. 5th ed. Great Britain: Pharmaceutical Press and the American Pharmacists Association, 2006; 940 pages.
Ruan et al., "Apolipoprotein A-I possesses an anti-obesity effect associated with increase of energy expenditure and upregulation of UCP1 in brown fat" *J. Cell. Mol. Med.* (2010). "Postprint"; 10.1111/j.1582.4934.2010.01045.x.
Rubin et al., "Expression of Human Apolipoprotein A-I in Transgenic Mice Results in Reduced Plasma Levels of Murine Apolipoprotein A-I and the Appearance of Two New High Density Lipoprotein Size Subclasses" *Proc. Natl. Acad. Sci. USA* 88:434-438 (1991).
Rubin et al., "Inhibition of Early Atherogenesis in Transgenic Mice by Human Apolipoprotein AI" *Nature* 353:265-267 (1991).
Rubins et al., "Reduction in Stroke with Gemfibrozil in Men with Coronary Heart Disease and Low HDL Cholesterol. The Veterans Affairs HDL Intervention Trial (VA-HIT)" *Circulation* 103:2828-2833 (2001).
Rubins et al., for the Veterans Affairs High-Density Lipoprotein Cholesterol Intervention Trial Study Group, "Gemfibrozil for the secondary prevention of coronary heart disease in men with low levels of high-density lipoprotein cholesterol" *N. Engl. J. Med.*, 341:410-418 (1999).
Rufo, A. et al. (2011) "Mechanisms Inducing Low Bone Density in Duchenne Muscular Dystrophy in Mice and Humans" *J Bone Miner Res*, 26(8):1891-1903.
Sahashi, K. et al. (2016) "Ultrastructural Localization of the Terminal and Lytic Ninth Complement Component (C9) at the Motor End-plate in Myasthenia Gravis" [online]. Downloaded from http://jnen.oxfordjournals.org/, pp. 160-172.
Saito et al., "Topical Antigen Provocation Increases the Number of Immunoreactive IL-4-, IL-5 and IL-6-Positive Cells in the Nasal Mucosa of Patients with Perennial Allergic Rhinitis," *Int. Arch. Allergy Immunol.* 114:81-85 (1997).
Samarkos, M. et al. (2012) "The Role of Complement in the Antiphospholipid Syndrome: A Novel Mechanism for Pregnancy Morbidity" *Seminars in Arthritis and Rheumatism*, 42:66-69.
Sarkhel et al., "3-Arylisocoumarin: Synthesis of 3-(4-methoxyphenyl)-isocoumarin" *J. Indian Chem. Soc.* 53:915-916 (1976).
Sarma and Ward (2011) "The complement system" *Cell Tissue Res.* 343(1):227-235. NIH Public Access Author Manuscript; available in PMC Jan. 1, 2012 (13 pages).
Sassano et al., "Interleukine-6 (IL-6) may be a link between myasthenia gravis and myoepithelioma of the parotid gland," *Med. Hypoth.*, 68:314-317 (2007).
Scandinavian Simvastatin Survival Group, "Randomised Trial of Cholesterol Lowering in 4444 Patients with Coronary Heart Disease: The Scandinavian Simvastatin Survival Study (4S)" *Lancet* 344:1383-1389 (1994).
Scheller et al., "Interleukin-6 Trans-Signalling in Chronic Inflammation and Cancer" *Scand. J. Immunol.*, 63:321-329 (2006).
Scheller et al., "The pro- and anti-inflammatory properties of the cytokine interleukin-6" *Biochim. Biophys. Acta*, 1813:878-888 (2011).

Schiess et al., "Thermolytic Ring Opening of Acyloxybenzocyclobutenes: An Efficient Route to 3-Substituted Isoquinolines" *Tetrahedron Lett.* 26:3959-3962 (1985).
Schmutz et al., "Synthese von basisch substituierten Chromonen" *Helv. Chim. Acta* 36:620-626 (1953) (German). English abstract from *Chemical Abstracts*, vol. 48, Col. 11401 (1954).
Scholl, H. et al. (2008) "Systemic Complement Activation in Age-Related Macular Degeneration" *PLoS ONE*, 3(7):1-7.
Schork, N.J., "Genetics of Complex Disease. Approaches, Problems, and Solutions" *Am. J. Respir. Crit. Care Med.* 156(4):5103-109 (Oct. 1997).
Schultz et al., "Protein composition determines the anti-atherogenic properties of HDL in transgenic mice" *Nature*, 365:762-764 (1993).
Schultz et al., "Role of stilbenes in the natural durability of wood: fungicidal structure-activity relationships" *Phytochemistry* 29(5):1501-1507 (1990).
Scoble et al., "Lipid Profiles in Patients with Atherosclerotic Renal Artery Stenosis" *Nephron*, 83:117-121 (1999).
Seddon et al., "Progression of Age-Related Macular Degeneration. Prospective Assessment of C-Reactive Protein, Interleukin 6, and Other Cardiovascular Biomarkers" *Arch Ophthalmol.*, 123:774-782 (2005).
Sehgal, "Interleukin 6 in infection and cancer" *Exp. Biol. Med.*, 195:183-191 (1990).
Seifert et al., "The complement system in atherosclerosis" *Atherosclerosis*, 73:91-104 (1988).
Sethi, S. et al. (2012) "C3 Glomerulonephritis: Clinicopathologic findings, complement abnormalities, glomerular proteomic profile, treatment and follow-up" *Kidney International*, 82(4):465-473.
Shah et al., "Effects of Recombinant Apolipoprotein A-$I_{Milano}$ on Aortic Atherosclerosis in Apolipoprotein E-Deficient Mice" *Circulation* 97(8):780-785 (1998).
Shapiro et al., "Micro Assay for 3-Hydroxy-3-Methylglutaryl-CoA Reductase in Rat Liver and L-Cell Fibroblasts" *Biochim. Biophys. Acta* 370:369-377 (1974).
Sharma and Das "Role of Cytokines in myocardial ischemia and reperfusion" *Mediators of Inflammation*, 6:175-183 (1997).
Sharrett et al., "Associations of Lipoprotein Cholesterols, Apolipoproteins A-I and B, and Triglycerides with Carotid Atherosclerosis and Coronary Heart Disease. The Atherosclerosis Risk in Communities (ARIC) Study" *Arterioscler Thromb.* 14:1098-1104 (1994).
Shichishima et al. (1999) "Complement sensitivity of erythrocytes in a patient with inherited complete deficiency of CD59 or with the Inab phenotype" *Brit. J. Haematol.* 104:303-306.
Shimizu et al. "Effects of Rosuvastatin and Atorvastatin on Macrophage Reverse Cholesterol Transport in Vivo" AHA Scientific Sessions, 2011. Core 2. Epidemiology and Prevention of CV Disease: Physiology, Pharmacology and Lifestyle; Session Title: Lipids, Lipid Mediators and Lipoprotein Metabolism: Cellular and Animal I. *Circulation* 124(21 Suppl.):A11181 (2011).
Shoji et al., "Concentration of Soluble Interleukin-6 Receptors in Tears of Allergic Conjunctival Disease in Patients" *Jpn. J. Ophthalmol.* 51:332-337 (2007).
Sieber, R.H., "Reactions of chloroacetaldehyde with aromatic hydrocarbons, phenols, and phenol ethers" *Justus Liebigs Annalen der Chemie* 730:31-46 (1969) (German). English abstract on p. 31.
Singh-Manoux et al., "Low HDL cholesterol is a risk factor for deficit and decline in memory in midlife: the Whitehall II Study" *Atherosclerosis, Thrombosis and Vascular Biology*, 28(8):1556-1562 (2008).
Skerka et al. (2013) "Complement factor H related proteins (CFHRs)" *Mol. Immunol.* 56:170-180.
Sliwa et al., "Tautomerie entre structures α-aleoxy-enaminocetone et β-ceto iminoether presentee par les piperidines resultant de la semihydrogenation d'alcoxy-2-acyl-3 pyridines" *J. Heterocyclic Chem.* 16:939-944 (1979) (French). English summary on p. 944.
Slowing et al., "Anti-Inflammatory Activity of Leaf Extracts of *Eugenia jambos* in Rats" *J. Ethnopharmacol.* 43:9-11 (1994).
Smyth et al., "Non-amine based analogues of lavendustin A as protein-tyrosine kinase inhibitors" *J. Med. Chem.* 36(20):3010-3014 (1993).

(56) References Cited

OTHER PUBLICATIONS

Soltys, J. et al. (2009) "Novel Complement Inhibitor Limits Severity of Experimentally Myasthenia Gravis" *Annals of Neurology*, 65(1):67-75.
Soucek et al. (2008) "Modelling Myc inhibition as a cancer therapy" *Nature*, 455:679-683. HHS Public Access Author Manuscript; available in PMC Jun. 28, 2015 [online]. Retrieved from: https://www.ncbi.nlm.nih.gov/pmc/articles/PMC4485609/, on Feb. 27, 2018 (16 pages).
Sowers et al., "Calcific uremic arteriolopathy. Pathophysiology, reactive oxygen species and therapeutic approaches" *Oxid. Med. Cell. Long.*, 3(2):109-121 (2010).
Sta, M. et al. (2011) "Innate and adaptive immunity in amyotrophic lateral sclerosis: Evidence of complement activation" *Neurobiology of Disease*, 42:211-220.
Stahl, A. et al. (2011) "Complement activation on platelet-leukocyte complexes and microparticles in enterohemorrhagic *Escherichia coli*—induced hemolytic uremic syndrome" *Blood*, 117(20):5503-5513.
Stampfer, "Cardiovascular disease and Alzheimer's disease: common links" *J Intern Med*, 260(3):211-223 (2006).
Steiner et al., "Interleukin-6 Overexpression Induces Pulmonary Hypertension" *Circ. Res.*, 104:236-244, with Supplemental Material, 28 pages (2009).
Stelmasiak et al., "Interleukin-6 concentration in serum and cerebrospinal fluid in multiple sclerosis patients" *Med. Sci. Monit.* 6(6):1104-1108 (2000).
Strakhan, M. et al. (2014) "36-Year-Old Female with Catastrophic Antiphospholipid Syndrome Treated with Eculizumab: A Case Report and Review of Literature" Hindawi Publishing Corporation, Case Reports in Hematology, vol. 2014, Article ID 704371, 7 pages.
Sullivan, N.J. et al. (2009) "Interleukin-6 induces an epithelial—mesenchymal transition phenotype in human breast cancer cells" *Oncogene*, 28(33):2940-2947. HHS Public Access Author Manuscript; available in PMC Aug. 30, 2017 (16 pages).
Sun et al., "In Vitro Testing of Drug Absorption for Drug Developability' Assessment: Forming an Interface Between in Vitro Preclinical Data and Clinical Outcome" *Curr. Opin. Drug Discov. Devel.* 7:75-85 (2004).
Suryadevara et al., "Association of Abnormal Serum Lipids in Elderly Persons with Artherosclerotic Vascular Disease and Demetia, Artheroslerotic Vascular Disease Without Demetia, Demetia Without Artherosclerotic Vascular Disease, and No Dementia or Artherosclerotic Vascular Disease" *J. Gerontol. Med. Sci.* 58A(9):859-861 (2003).
Suzuki et al. (2014) "Development of animal models of human IgA nephropathy" *Drug Discov. Today Dis. Models* 11:5-11. NIH Public Access Author Manuscript; available in PMC Aug. 15, 2015 (12 pages).
Swiecicki, P. et al. (2013) "Cold agglutinin disease" *Blood*, 122(7):1114-1121.
Tacke et al., "Inflammatory Pathways in Liver Homeostasis and Liver Injury" *Clinic. Rev. Allerg. Immunol.*, 36:4-12 (2009).
Tackey et al., "Rationale for interleukin-6 blockade in systemic lupus" *Lupus* 13(5):339-343 (2004). Author manuscript, NIH Public Access, Oct. 11, 2007.
Taga et al., "Receptors for B cell stimulatory factor 2. Quantitation, specificity, distribution, and regulation of their expression" *J. Exp. Med.*, 166:967-981 (1987).
Tait et al., "Synthesis and Free Radical Scavenging Activity of 4-(2H-1,2,4-Benzothiadiazine-1,1-dioxide-3-yl)-2,6-bis(1,1-dimethylethyl)phenols" *Tetrahedron* 52(38):12587-12596 (1996).
Talbert, "Current Recommendations for the Treatment of Dyslipidemia" *Pharm. Ther.* 29:104 (2004).
Tall "Plasma High Density Lipoproteins" *J. Clin. Invest.* 86: 379-384 (1990).
Tanne et al., "High-Density Lipoprotein Cholesterol and Risk of Ischemic Stroke Mortality" *Stroke* 28:83-87 (1997).

Tardif et al. "Effects of reconstituted high-density lipoprotein infusions on coronary atherosclerosis: A randomized controlled trial" *JAMA* 297:1675-1682 (2007).
Tardif et al., "Probucol and Multivitamins in the Prevention of Restenosis After Coronary Angioplasty" *N. Engl. J. Med.* 337:365-367 (1997).
Tasaki et al., "Comparison of serum lipid values in variant angina pectoris and fixed coronary artery disease with normal subjects" *Am. J. Cardiol.* 63(20):1441-1445 (1989).
Tataru et al. "D-dimers in relation to the severity of arteriosclerosis in patients with stable angina pectoris after myocardial infarction" *Eur. Heart J.* 20:1493-1502 (1999).
Tchirkov, A. et al. (2007) "Interleukin-6 gene amplification and shortened survival in glioblastoma patients" *Br J Cancer*, 96:474-476.
Terinte et al., "Overview on native cellulose and microcrystalline cellulose I structure studied by x-ray diffraction (WAXD): Comparison between measurement techniques" *Lenzinger Berichte* 89:118-131 (2011).
Theriault et al., "Modulation of hepatic lipoprotein synthesis and secretion by taxifolin, a plant flavonoid," *J. Lipid Res.* 41:1969-1979 (2000).
Thoorens et al., "Microcrystalline cellulose, a direct compression binder in a quality by design environment a review" *Intl. J. Pharmaceut.* 473:64-72 (2014).
Toku-E Product Data Sheet, "Oxytetracycline dihydrate" [online]. Retrieved from the Internet: http://www.toku-e.com/product/oxytetracycline_dihydrate, on Feb. 5, 2015 (2 pages).
Toshitani et al., "Increased Interleukin 6 Production by T Cells Derived from Patients with Atopic Dermatitis" *J. Invest. Dermatol.* 100:299-304 (1993).
Toth et al., "Therapeutic Interventions Targeted at the Augmentation of Reserve Cholesterol Transport" *Curr. Opin. Cardiol.* 19:374-379 (2004).
Tovar et al., "Pyrylium Salts via Electrophilic Cyclization: Applications for Novel 3-Arylisoquinoline Syntheses" *J. Org. Chem.* 64:6499-6504 (1999).
Trikha et al., "Targeted anti-interleukin-6 monoclonal antibody therapy for cancer: a review of the rationale and clinical evidence" *Clin. Cancer Res.*, 9:4653-4665 (2003).
Tsujinaka, T. et al. (1998) "Muscle Wasting and IL-6" *Basic Appl Myol*, 8(5):361-370.
Tudan, "Selective Inhibition of Protein Kinase C, Mitogen-Activated Protein Kinase, and Neutrophil Activation in Response to Calcium Pyrophosphate Dihydrate Crystals, Formyl-Methionyl-Leucyl-Phenylalanine, and Phorbol Ester by O-(Chloroacetyl-carbamoyl) Fumagillol (AGM-01470; TNP-470)" *Biochem. Pharmacol.* 58:1869-1880 (1999).
Tulamo, R. et al. (2006) "Complement Activation Associates With Saccular Cerebral Artery Aneurysm wall Degeneration and Rupture" *Neurosurgery*, 59:1069-1077.
Tulamo, R. et al. (2010) "Lack of Complement Inhibitors in the Outer Intracranial Artery Aneurysm Wall Associates with Complement Terminal Pathway Activation" *American Journal of Pathology*, 177(6):3224-3232.
Turki, A. et al. (2012) "Functional muscle impairment in facioscapulohumeral muscular dystrophy is correlated with oxidative stress and mitochondrial dysfunction" *Free Radical Biology and Medicine*, 53:1068-1079.
Turner et al., "Interleukin-6 Levels in the Conjunctival Epithelium of Patients with Dry Eye Disease Treated with Cyclosporine Ophthalmic Emulsion" *Cornea* 19(4):492-496 (2000).
Tuttle, "Linking Metabolism and Immunology: Diabetic Nephropathy Is an Inflammatory Disease" *J. Am. Soc. Nephrol.* 16:1537-1538 (2005).
Tuzun, E. et al. (2013) "Complement associated pathogenic mechanisms in myasthenia gravis" *Autoimmunity Reviews*, 12:904-911.
Ulvestad, E. et al. (2001) "Acute Phase Haemolysis in Chronic Cold Agglutinin Disease" *Scandinavian Journal of Immunology*, 54:239-242.
Utermann, "The Mysteries of Lipoprotein(a)" *Science* 246:904-910 (1989).

(56) References Cited

OTHER PUBLICATIONS

Uzawa et al., "Cytokine and chemokine profiles in neuromyelitis optica: significance of interleukin-6" *Multiple Sclerosis*, 16(12):1443-1452 (2010).
Van De Waterbeemd et al. (1997) "Glossary of Terms Used in Computational Drug Design" *Pure & Appl. Chem.*, 69(5):1137-1152.
Van Der Goot et al., "The Growth-Inhibitory Action of Some 1-Aminoisoquinolines and Related Compounds on Mycoplasma Gallisepticum" *Eur. J. Med. Chem.—Chimica Thereapeutica* 10:603-606 (1975).
Van Lenten et al., "Anti-inflammatory apoA-I-mimetic peptides bind oxidized lipids with much higher affinity than human apoA-I" *J. Lipid Res.* 49:2302-2311 (2008).
Van Lenten et al., "Apolipoprotein A-I Mimetic Peptides" *Curr. Atheroscler Rep.* 11(1):52-57 (2009).
Van Lenten et al., "Multiple indications for anti-inflammatory peptides" *Curr. Opin. Investig. Drugs* 9(11):1157-1162 (2008).
Varin et al., "Enzymatic Assay for Flavonoid Sulfotransferase" *Anal. Biochem.* 161:176-180 (1987).
Varthalis et al., "The action of colloidal silicon dioxide as a glidant for lactose, paracetamol, oxytetracycline and their mixtures" *J. Pharm. Pharmac.* 29:37-40 (1997).
Vega-Ostertag et al., "Involvement of p38 MAPK in the Up-Regulation of Tissue Factor on Endothelial Cells by Antiphospholipid Antibodies" *Arthritis & Rheumatism*, 52(5):1545-1554 (2005).
Vernon, K.A. et al. (2011) "Recurrence of Complement Factor H-Related Protein 5 Nephropathy in a Renal Transplant" *American Journal of Transplantation*, 11:152-155.
Vippagunta et al., "Crystalline solids" *Adv. Drug Delivery Rev.* 48:3-26 (2001).
Vita and Henrickson (2006) "The Myc oncoprotein as a therapeutic target for human cancer" *Seminars in Cancer Biol*, 16:318-330.
Vivarelli, M. et al. (2012) "Eculizumab for the Treatment of Dense-Deposit Disease" *N Engl J Med*, 366(12):1163-1165.
Vlaicu et al., "The role of complement activation in atherogenesis: the first 40 years" *Immunol. Res.* 64:1-13 (2016).
Voorhees, P.M. et al. (2007) "Inhibition of Interleukin-6 Signaling with CNTO 328 Enhances the Activity of Bortezomib in Preclinical Models of Multiple Myeloma" *Clin Cancer Res*, 13(211):6469-6478.
Voorhees, P.M. et al. (2009) "Targeted Inhibition of Interleukin-6 with CNTO 328 Sensitizes Pre-clinical Models of Multiple Myeloma to Dexamethasonemediated Cell Death" *Br J Haematol*, 145(4):481-490. NIH Public Access Author Manuscript; available in PMC Jan. 11, 2011 (19 pages).
Vuilleumier et al., "Pro- or anti-inflammatory role of apolipoprotein A-1 in high-density lipoproteins?" *Swiss Medical Weekly, The European Journal of Medical Sciences* 143:w13781 1-12 (2013).
Wada et al., "Increased plasma level of interleukin-6 in disseminated intravascular coagulation" *Blood Coagulation and Fibrinolysis*, 4:583-590 (1993).
Waiser et al., "Interleukin-6 expression after renal transplantation" *Nephrol. Dial. Transplant.*, 12:753-759 (1997).
Walldius et al., "The apoB/apoA-I ratio: a strong, new risk factor for cardiovascular disease and a target for lipid-lowering therapy—a review of the evidence" *J. Internal Med.* 259:493-519 (2006).
Walle, "Absorption and Metabolism of Flavonoids" *Free Radical Biol. Med.* 36(7):829-837 (2004).
Walport (2001) "Complement First of two parts" *N. Engl. J. Med.* 344(14):1058-1066.
Walsh et al., "High Levels of Human Apolipoprotein A-I in Transgenic Mice Result in Increased Plasma Levels of Small High Density Lipoprotein (HDL) Particles Comparable to Human $HDL_3$" *J. Biol. Chem.* 264(11):6488-6494 (1989).
Walters et al. (2002) "Complement factor 3 mediates particulate matter-induced airway hyperresponsiveness" *Am. J. Respir. Cell Mol. Biol.* 27(4):413-418.
Wang et al. (2000) "A role for complement in antibody-mediated inflammation: C5-deficient DBA/1 mice are resistant to collagen-induced arthritis" *J. Immunol.* 164(8):4340-4347.
Wang et al. (2011) "Statins: Multiple neuroprotective mechanisms in neurodegenerative diseases" *Exp. Neurol.*, 230(1):27-34.
Wang et al. (2012) "Association analysis of cytokine polymorphisms and plasma level in Northern Chinese Han patients with paroxysmal nocturnal hemoglobinuria" *Chin. Med. J.*, 125(9):1576-1580.
Wang, H. et al. (2014) "Increased Soluble C5b-9 in CSF of Neuromyelitis Optica" *Scandinavian Journal of Immunology*, 79:127-130.
Wannamethee et al., "Circulating inflammatory and hemostatic biomarkers are associated with risk of myocardial infarction and coronary death, but not angina pectoris, in older men" *J. Thromb. Haemost.* 7:1605-1611 (2009).
Warden et al., "Atherosclerosis in Transgenic Mice Overexpressing Apolipoprotein A-II" *Science* 261:469-472 (1993).
Wasiak, S. et al. (2016) "Data on gene and protein expression changes induced by apabetalone (RVX-208) in ex vivo treated human whole blood and primary hepatocytes" *Data in Brief* 8:1280-1288.
Wei et al., "Total Cholesterol and High Density Lipoprotein Cholesterol as Important Predictors of Erectile Dysfunction" *Am. J. Epidemiol.* 140(10):930-937 (1994).
Weitz et al., "Eculizumab therapy results in rapid and sustained decreases in markers of thrombin generation and inflammation in patients with PNH independent of its effects on hemolysis and microparticle formation" *Thromb. Res.*, 130:361-368 (2012).
Wellington et al. "Alterations of plasma lipids in mice via adenoviral-mediated hepatic overexpression of human ABCA1" *Lipid Res.* 44:1470-1480 (2003).
Welsh et al., "Dyslipidemia in Diabetic Patients" *Prospectives in Cardiology*, Aug. 2002, pp. 40-48.
Westwood et al., "Complement and cytokine response in acute Thrombotic Thrombocytopenic Purpura" *Br. J. Haematol.*, 164:858-866 (2014).
Wijdenes et al., "Human recombinant dimeric IL-6 binds to its receptor as detected by anti-IL-6 monoclonal antibodies" *Mol. Immunol.*, 28:1183-1192 (1991).
Wikipedia, "Complement system" [online] Retrieved from: https://en.wikipedia.org/wiki/Complement_system, on Nov. 4, 2016 (9 pages).
Wolfrum et al., "Endothelium-Dependent Effects of Statins" *Arteriosder. Thromb. Vasc. Biol.*, 23:729-736 (2003).
Wölle et al., "Selective inhibition of tumor necrosis factor-induced vascular cell adhesion molecule-1 gene expression by a novel flavonoid. Lack of effect on transcription factor NF-kappa-B" *Arterioscler. Thromb. Vasc. Biol.* 16(12):1501-1508 (1996).
Wong, N.C. et al. (Apr. 5, 2011) "RVX-208 Decreases Progression of Atherosclerosis in ApoE Null Mice" *J Amer Coll Cardiol*, 57(15):E1437 (1 page).
Woodruff, T. et al. (2008) "The Complement Factor C5a Contributes to Pathology in a Rat Model of Amyotrophic Lateral Sclerosis" *Journal of Immunology*, 181:8727-8734.
World Health Organization (WHO), "Cardiovascular Disease and Heredity: Possibilities for Prevention and Management with Genetics" [online]. Retrieved from: http://www.who.int/genomics/about/CVD.pdf?ua=1, on Oct. 19, 2016 (12 pages).
Wright et al., "Statin Lipid-Lowering Therapy for Acute Myocardial Infarction and Unstable Angina: Efficacy and Mechanism of Benefit" *Mayo Clin. Proc.*, 77:1085-1092 (2002).
Wurm et al., "1,4-Naphthoquinones, XXVI: Phenyl-1,4-naphthoquinone derivatives with the hydroxylation patterns of bioflavonoids" *Pharmazie* 52(10):739-743 (1997) (German). English abstract on p. 739.
Wurm, "1,4-Naphthoquinones, XXI: 2-(3,5 Di-tert-butyl-4-hydroxyphenyl)-1,4-naphtoquinones as 5-lipozxygenase inhibitors" *Archiv. der Pharmazie* 324(8):491-495 (1991) (German). English abstract on p. 491.
Xia, Y. et al., "Antitumor Agents. Part 204: Synthesis and Biological Evaluation of Substituted 2-Aryl Quinazolinones" *Bioorg. Med. Chem. Lett.*, 11(9):1193-1196 (2001).

(56) References Cited

OTHER PUBLICATIONS

Xu, H. et al. (2016) "Targeting the complement system for the management of retinal inflammatory and degenerative diseases" *Eur J Pharmacol*, 787:94-104.

Yamakoshi et al., "Isoflavone aglycone-rich extract without soy protein attenuates atherosclerosis development in cholesterol-fed rabbits" *Journal of Nutrition* 130(8):1887-1893 (2000).

Yang et al., "Inhibition of insulitis and prevention of diabetes in nonobese diabetic mice by blocking L-selectin and very late antigen 4 adhesion receptors" *Proc. Natl. Acad. Sci. USA*, 90:10494-10498 (1993).

Yardley et al., "In vitro activity of diospyrin and derivatives against *Leishmania donovani, Trypanosoma cruzi* and *Trypanosome brucei brucei*" *Phytotherapy Research* 10(7):559-562 (1996).

Yellon and Hausenloy (2007) "Myocardial reperfusion injury" *N. Engl. J. Med.* 357(11):1121-1135.

Yoshikawa et al., "Cytokine secretion by peripheral blood mononuclear cells in myasthenia gravis" *J. Clin. Neurosci.*, 9(2):133-136 (2002).

Yoshioka et al., "Semiempirical Investigation of Stilbene-Linked Diradicals and Magnetic Study of Their Bis(N-tert-butylnitroxide) Variants" *J. Org. Chem.* 59(15):4272-4280 (1994).

Zacharowski et al., "Fibrin(ogen) and its fragments in the pathophysiology and treatment of myocardial infarction" *J. Mol. Med.* 84:469-477 (2006).

Zamani et al., "Inflammatory Biomarkers, Death, and Recurrent Nonfatal Coronary Events After an Acute Coronary Syndrome in the MIRACL Study" *J. Am. Heart Assoc.*, 1:e003103, doi:10.1161/JAHA.112.003103 (2012).

Zannis et al., "Intracellular and extracellular processing of human apolipoprotein A-I: Secreted apolipoprotein A-1 isoprotein 2 is a propeptide" *Proc. Natl. Acad. Sci. USA* 80:2574-2578 (1983).

Zhang and Köhl (2010) "A complex role for complement in allergic asthma" *Expert Rev. Clin. Immunol.* 6(2):269-277. NIH Public Access Author Manuscript; available in PMC Jan. 1, 2011 (17 pages).

Zhang et al. (2012) "Down-regulation of NF-κB Transcriptional Activity in HIV-associated Kidney Disease by BRD4 Inhibition" *J Biol Chem*, 287(34):28840-28851.

Zhang et al., "Inhibition of the Interleukin-6 Signaling Pathway: A Strategy to Induce Immune Tolerance" *Clinic. Rev. Allerg. Immunol.*, 47:163-173 (2014).

Zhu et al., "Regulation of apoAI processing by procollagen C-proteinase enhancer-2 and bone morphogenetic protein-1" *J. Lipid Res.* 50:1330-1339 (2009).

Narayana et al., "Synthesis of new 2-substituted pyrido[2,3-d]pyrimidin-4(1H)-ones and their antibacterial activity", European Journal of Medicinal Chemistry 44(2009):1369-1376.

\* cited by examiner

COMPOSITIONS AND THERAPEUTIC METHODS FOR THE TREATMENT OF COMPLEMENT-ASSOCIATED DISEASES

This application is a continuation of U.S. patent application Ser. No. 15/066,513, filed Mar. 10, 2016 (now U.S. Pat. No. 10,111,885), which claims priority from U.S. Provisional Patent Application No. 62/132,572, filed Mar. 13, 2015, and U.S. Provisional Patent Application No. 62/264,768, filed Dec. 8, 2015, which are hereby incorporated by reference in their entirety.

The present disclosure relates to methods of treating or preventing complement-associated diseases or disorders by administering to a subject in need thereof, a compound of Formula I or Formula II or a stereoisomer, tautomer, pharmaceutically acceptable salt, or hydrate thereof. Therapeutic strategies for modulating the complement system to treat or prevent diseases or disorders associated with aberrant complement system activity are disclosed.

Compounds of Formula I and methods of making those compounds have previously been described in U.S. Pat. No. 8,053,440, incorporated herein by reference. Compounds of Formula I include:

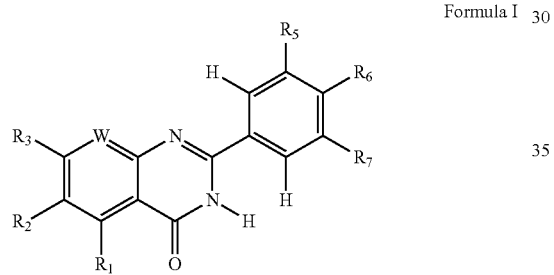

Formula I and stereoisomers, tautomers, pharmaceutically acceptable salts, or hydrates thereof, wherein:

$R_1$ and $R_3$ are each independently selected from alkoxy, alkyl, amino, halogen, and hydrogen;

$R_2$ is selected from alkoxy, alkyl, alkenyl, alkynyl, amide, amino, halogen, and hydrogen;

$R_5$ and $R_7$ are each independently selected from alkyl, alkoxy, amino, halogen, and hydrogen;

$R_6$ is selected from amino, amide, alkyl, hydrogen, hydroxyl, piperazinyl, and alkoxy; and W is CH or N.

In some embodiments, when $R_6$ is selected from alkoxy, it is optionally substituted with one or more groups chosen from amide, amine, aryl, benzyloxy, carbamate, carboxy, heterocyclyl, hydroxyl, methoxy, and sulfonamide.

Compounds of Formula II and methods of making those compounds have previously been described in U.S. Pat. No. 8,569,288 and PCT Publication No. WO2010/049466, incorporated herein by reference. Compounds of Formula II include:

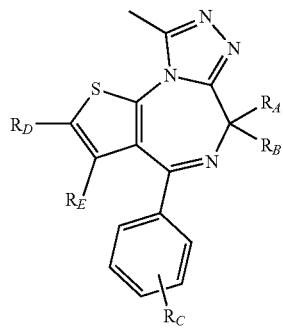

Formula II and stereoisomers, tautomers, pharmaceutically acceptable salts, or hydrates thereof, wherein:

$R_A$ and $R_B$ are independently selected from hydrogen, methyl, —$(CH_2)_n R_F$, —$(CH_2)_n OR_F$, and —$CH_2 C(O) OR_G$;

$R_C$ is selected from hydrogen, para-halogen, and —$OCH_2O$— or —$OCH_2CH_2O$— connected to the ortho and meta positions or connected to the meta and para positions of the phenyl ring;

$R_D$ and $R_E$ are independently selected from hydrogen and methyl;

$R_F$ is selected from methyl, ethyl, and —$CH_2CH_2OCH_3$;

$R_G$ is selected from methyl, ethyl, n-propyl, isopropyl, n-butyl, and tert-butyl; and n is selected from 1, 2, 3, and 4.

The main function of the human immune system is host defense. This system distinguishes locally-produced entities, including tissues, cells and molecules, from foreign entities, referred to as pathogens, and eliminates these potentially harmful molecules and cells from the body. Additionally, the immune system has the ability to recognize and remove abnormal cells that are derived from host tissues. Molecules that are recognized as foreign entities by the immune system are termed antigens. The immune system is composed of two responses, the innate response and the adaptive response. Several molecular components, such as, complement proteins, cytokines and acute phase proteins, act in both the innate and adaptive immune responses.

Adaptive immunity is known as the antigen-specific immune response. It functions through a sequence of recognition and processing events that result in either an antibody or cell-mediated response. Two main classes of lymphocytes (white blood cells), T cells and B cells, are involved in adaptive immunity. The recognition of foreign antigens by a vast array of antigen-specific receptors on these lymphocytes enables specific identification and elimination of pathogens. This process may take several days or weeks to develop, but the adaptive immune response employs immunological memory to incur a stronger, more rapid response upon subsequent exposure to the specific antigen.

In contrast, innate immunity refers to the non-specific immune response that is activated immediately following the introduction of an entity recognized as foreign into the body. The innate immune response is not adaptable and does not change over the course of an individual's lifetime. The components of the innate immune response, including monocytes, neutrophils, eosinophils, basophils and natural killer cells, circulate in the blood and are readily activated and localized at the site of an immune breach.

The complement system contains a network of tightly regulated proteins when taken together are a key part of the innate immune response. The complement system represents one of the major effector mechanisms of the innate immune response, and comprises more than 30 blood soluble or membrane-associated proteins. The concentration of these proteins in the plasma totals more than 3 g per liter. Walport (2001) "Complement First of two parts." *N Engl J Med* 344(14): 1058-1066.

Most complement proteins circulate as pro-proteins and the complement system remains inactive until triggered. The array of complement proteins are organized in a hierarchy of proteolytic cascades that are triggered by the recognition of antigen-antibody complex or simply an antigen on the surface of a pathogen. Antibodies are serum proteins that are produced by B cells in the adaptive immune response to enable more rapid recognition of known antigens. Therefore, if a like-antigen is reintroduced, the circulating antibodies are readily available to bind the antigen and create the antigen-antibody complex, which is subsequently recognized by T cells or the complement system.

The activation of the complement system involves zymogenic proteins (inactive enzymatic protein) that are subsequently cleaved and activated by a series of proteases. Complement activation is known to occur through three principal pathways: classical, alternative and lectin. Though various factors can initiate complement activation, the three main pathways converge at the cleavage of C3, the most abundant complement protein in the blood. Dunkelberger and Song (2010) "Complement and its role in innate and adaptive immune responses" *Cell Res* 20(1): 34-50.

The initiation of the classical pathway is triggered via the recognition of antigen-antibody (immune) complexes on the surface of foreign cells by complement protein C1q in complex with C1r and C1s (the C1 complex). Sarma and Ward (2011) "The complement system" *Cell Tissue Res* 343(1): 227-235. The interaction of the C1 complex with the immune complex results in the autocatalytic activation of the two C1-associated proteases, C1r and C1s. Other activation stimuli of the C1 complex include lipopolysaccharides, polyanions, RNA and DNA from foreign cells. Activated C1s cleaves C2 and C4 into larger (C4b and C2a) and smaller (C4a and C2b) fragments. Dunkelberger and Song (2010). The C4b and C2a fragments subsequently bind to the cell membrane of the foreign cell being attacked by the immune system. The resultant C4bC2a complex functions as a C3 convertase. Amplification of the proteolytic complement cascade occurs on the cell membrane through the sequential cleavage of complement proteins including C3, C5, and the recruitment of new factors, until a cell surface complex containing C5b, C6, C7, and C8 is formed. The additional accumulation of multiple C9 proteins to the C5b through C8 complex generates the membrane attack complex (MAC), which leads to the formation of a pore that spans the membrane of the foreign cell, resulting in cell lysis.

The lectin-induced complement pathway functions in analogous, yet immune complex-independent fashion, compared to the classical pathway. Dunkelberger and Song (2010). Its activation occurs via by the binding of mannose-binding lectin (MBL) or ficolin to carbohydrates on the surface of foreign cells. Sarma and Ward (2011). MBL is an acute phase serum protein and circulates in the serum in complex with the MBL-associated proteases (MASPs)-1, -2 and -3. Dunkelberger and Song (2010). The binding of MBL to the surface of the foreign cell, activates MASP1 and MASP2 which subsequently trigger the cleavage of C2 and C4 resulting in the creation of C4b and C2a fragments, and the formation of the C3 convertase, C4bC2a. MASP1 and MASP2 are structurally similar and act in a comparable manner to the C1 protease in the classical complement pathway. The lectin-induced pathway is then amplified in a similar manner as the classical pathway. The remaining complement proteins (C3 through C9) are recruited and activated, resulting in the assembly of the MAC that lyses the foreign cell.

The alternative pathway (AP) does not require an antigen-antibody complex to be triggered. In addition to the complement proteins (C3 through C9) that function readily in the classical and lectin-induced pathways, circulating serum proteins referred to as factors (factor B, factor D, factor H, factor I) also function in the activation and regulation of the AP.

The AP initiates with the low-level spontaneous conversion of C3 to an active protease, C3b. Sarma and Ward (2011). Circulating factor B is recruited and cleaved by circulating factor D to create the active protease C3 convertase. This enzyme cleaves C3 to form C3b, the AP specific C3 convertase, which is stabilized by the presence of plasma properdin, a protein released by activated neutrophils. The C3b functions in an analogous fashion to the classical and lectin-induced C3 convertase, C4bC2a. Dunkelberger and Song (2010). The alternative pathway is then amplified in a similar manner as the classical pathway, recruiting additional complement proteins (C6, C7, C8 and C9), resulting in the formation of the membrane attack complex and cell lysis. In the absence of an antibody targeted response, the constant low level of C3b formation ensures that C3b can bind to invading cells, triggering cell lysis. Factor H and factor I act as regulators of the alternative pathway via their ability to inactivate C3b. The recruitment of plasma properdin protects the C3b when it is membrane bound, and thus the alternative pathway is only active on the surface of foreign cells and not continuously active in plasma.

Additional proteases released by neutrophils and macrophages, including kallikrein, plasmin and Factor XIIa, produce complement activation products. For example, kallikrein can replace factor D in the AP and cleaves factor B. DiScipio (1982) "The activation of the alternative pathway C3 convertase by human plasma kallikrein" *Immunology* 45(3): 587-595. These pathways are referred to as C3-independent pathways.

The complement and coagulation systems are both proteolytic cascades. The elements of these cascades have multiple structurally common characteristics. Markiewski et al. (2007) "Complement and coagulation: strangers or partners in crime?" *Trends Immunol* 28(4): 184-192. Activation of the complement system is induced by the same stimuli as inflammation and in general, these responses are associated with an increase in blood clotting. Esmon (2004) "The impact of the inflammatory response on coagulation" *Thromb Res* 114(5-6): 321-327. Injuries to the vasculature result in the activation of blood coagulation and are associated with an increased risk of infection, and thus a subsequent inflammatory response is triggered. Keel and Trentz (2005) "Pathophysiology of polytrauma" *Injury* 36(6): 691-709. Therefore, the activation of the complement and coagulation cascades are triggered concurrently. Markiewski et al. (2007). Complement proteins including C5a and MASPs, are known to amplify the coagulation cascade and inhibit fibrinolysis (the breakdown of polymerized fibrin, the main protein component of a blood clot) through the induced expression of tissue factor and plasminogen-activator inhibitor 1, and the formation of thrombin (the active form of prothrombin that functions by facilitating the conversion of fibrinogen to fibrin) from prothrombin, respectively. Ricklin et al. (2010) "Complement: a key system for immune surveillance and homeostasis" *Not Immunol* 11(9): 785-797. Complement proteins C3 and C5 are large proteins that are proteolytically cleaved into a- and b-fragments. Ogata et al. (1989) "Sequence of the gene for murine complement component C4" *J Biol Chem* 264(28): 16565-16572. Several mechanisms exists which function to regulate complement activity. Plasma carboxypeptidases cleave both C3a and C5a to significantly reduce their biological activity, proteases factors I and H function in the cleavage of C3b and C4b, and C1 inhibitor inactivates the C1 receptor and MASP2. Sarma and Ward (2011).

The activity of complement in terms of initiating immune responses makes it a target for immune evasion and a contributor to many disease states. Ricklin and Lambris (2007) "Complement-targeted therapeutics" *Nat Biotechnol* 25(11): 1265-1275. Excessive complement activity is associated with several inflammatory, autoimmune, neurodegenerative and infectious diseases. Ricklin and Lambris (2007). The involvement of complement in the pathologies of such diseases may be a result of either the inappropriate initiation of the complement cascade or deficiencies in specific factors or regulators of the various pathways. Ricklin and Lambris (2007).

Age-related macular degeneration (AMD) has recently emerged as being strongly linked to the complement system as complement deposits were identified in sub-retinal lipoprotein deposits. Anderson et al. (2010) "The pivotal role of the complement system in aging and age-related macular degeneration: hypothesis re-visited" *Prog Retin Eye Res* 29(2): 95-112. Genome wide association studies (GWAS) showed that polymorphisms in the factor H gene were major risk factors of AMD. Klein et al. (2005) "Complement factor H polymorphism in age-related macular degeneration" *Science* 308(5720): 385-389. Genetically determined protein dysfunction of factor H can lead to uncontrolled activation and/or regulation of the alternative complement pathway. Gehrs et al. (2010) "Complement, age-related macular degeneration and a vision of the future" *Arch Ophthalmol* 128(3): 349-358. In addition, genetic variants of the C3 and Factor B genes, whose products play a role in the activation and regulation of the alternative complement pathway within the sub-retinal tissue have been identified. Gehrs et al. (2010). The exact pathogenesis of AMD is not yet fully understood, however, a cycle of tissue damage, accumulation of cellular debris, chronic activation of complement and inflammation appears to be the main contributor to the disease state. Anderson et al. (2010). Hereditary angioedema (HAE) is caused by a deficiency in functional C1 esterase inhibitor (C1INH), a complement protein that prevents spontaneous activation of the complement system. Deficiency in functional C1INH results in overproduction of bradykinin and unregulated C4 and C2 cleavage, which causes auto-activation of the complement system. Recombinant human C1INH has been shown to be effective in improving symptoms of repeat HAE attacks (Li et al. 2015).

Allergic asthma is a chronic inflammatory disease which is associated with the activation of complement. Zhang and Kohl (2010) "A complex role for complement in allergic asthma" *Expert Rev Clin Immunol* 6(2): 269-277. In animal models of the disease state, inhibition of complement activation via the Crry gene (a known mouse membrane complement inhibitor), targeting C3 and C5, decreased the allergic asthma phenotype. Walters et al. (2002) "Complement factor 3 mediates particulate matter-induced airway hyperresponsiveness" *Am J Respir Cell Mol Biol* 27(4): 413-418; Peng et al. (2005) "Role of C5 in the development of airway inflammation, airway hyperresponsiveness, and ongoing airway response" *J Clin Invest* 115(6): 1590-1600. Evidence suggests a strong association between complement activation and the pathogenesis of allergic asthma.

There is strong evidence that both the classical and the alternative pathways of complement are pathologically activated during rheumatoid arthritis (RA) as well as in animal models for RA. Okroj et al. (2007) "Rheumatoid arthritis and the complement system" *Ann Med* 39(7): 517-530. The genetic inactivation of C3, C5 or Factor B in the DBA/1J (Dilute Brown Non-Agouti) mouse (RA mouse model) showed that the mice developed resistance to collagen-induced arthritis. Wang et al. (2000) "A role for complement in antibody-mediated inflammation: C5-deficient DBA/1 mice are resistant to collagen-induced arthritis" *J Immunol* 164(8): 4340-4347. In addition, C3 knockout mice as well as Factor B knockout mice were highly resistant to the development of arthritis (collagen-induced arthritis in the mouse). Hietala et al. (2002) "Complement deficiency ameliorates collagen-induced arthritis in mice" *J Immunol* 169(1): 454-459. Evidence suggests a strong association between complement activation and the pathogenesis of RA.

Deficiencies and polymorphisms of components of the alternative pathway, including Factor H, C3, Factor B, and Factor I, may result in the induction of excessive complement activation leading to two severe kidney diseases. Noris and Remuzzi (2009) "Atypical hemolytic-uremic syndrome" *N Engl J Med* 361(17): 1676-1687. Both atypical hemolytic uremic syndrome (aHUS) and membranoproliferative glomerulonephritis result from the inability of the complement system to neutralize or stabilize the C3 convertase. Ricklin et al. (2010). These two diseases can lead to hemolytic anemia, thrombocytopenia and acute renal failure. Sarma and Ward (2011).

IgA nephropathy (IgAN) is characterized by the mesangial accumulation of polymeric IgA1 and C3 with variable IgG and/or IgM co-deposits. Previous studies have shown that complement proteins are important for initiation and progression of IgAN in animal models and human diseases. Suzuki et al. (2014) "Development of animal models of human IgA nephropathy" *Drug Discov Today Dis Models* 11: 5-11. Thus, modulating the complement cascade and its components may prevent or treat IgAN.

There is evidence that complement factor H related protein 5 (CFHR5) protects from complement dysregulation. CFHR5 nephropathy is a type of C3 glomerulopathy with autosomal dominant inheritance and is associated with a single genetic abnormality, causing an internal duplication in the CFHR5 gene. The mutant CFHR5 protein binds to membrane-associated C3b less effectively than the wild-type protein, causing dysregulation of the complement system. Skerka et al. (2013) "Complement factor H related proteins (CFHRs)" *Mol Immunol* 56: 170-180.

Complement factor H related protein 3 (CFHR3) also has complement regulatory activity as it inhibits C3-invertase. In a previous study, a hybrid CFHR3-1 gene was shown to cause familial C3 glomerulopathy. The authors suggested that this genetic mutation increased expression of both CFHR5 and CFHR3 and interfered with complement processing, leading to C3 accumulation. Malik et al. (2012) "A hybrid CFHR3-1 gene causes familial C3 glomerulopathy" *J Am Soc Nephrol* 23(7): 1155-1160.

C3 glomerulonephritis (C3GN) is a key example of a dysregulated alternative and terminal complement pathway.

C3GN, characterized by C3 deposition in the absence of local immunoglobin deposits, is caused by disease-causing mutations in alternative pathway inhibitors as well as autoantibodies leading to the blockage of activation of alternative pathway proteins. Heeringa and Cohen (2012) "Kidney diseases caused by complement dysregulation: acquired, inherited, and still more to come" *Clin Dev Immunol* 1-6.

CD59, the inhibitory membrane attack complex protein, and DAF, the complement decay-accelerating factor, are important in the inhibition of the MAC and function by dissociating C3 and C5 convertase, respectively. Sarma and Ward (2011). These regulators are membrane-bound via a glycophosphatidyinositol (GPI) anchor. A genetic mutation resulting in decreased expression of the GPI containing proteins leads to paraoxysmal nocturnal hemoglobunuria (PNH), which results in complement-mediated lysis of red blood cells. Liebman and Feinstein (2003) "Thrombosis in patients with paroxysmal noctural hemoglobinuria is associated with markedly elevated plasma levels of leukocyte-derived tissue factor" *Thromb Res* 111(4-5): 235-238. A direct link exists between the excessive complement activation, due to the inability to inhibit the MAC and the clinical manifestation of PNH.

Complement regulatory protein CD59 plays an important role in the complement cascade by preventing C9 from polymerizing and forming the complement membrane attack complex. Thus, CD59 deficiency can result in increased complement sensitivity and dysregulation of the complement system. A previous study using the complement lysis sensitivity (CLS) test found that the erythrocytes from a patient with inherited complete deficiency of CD59 were about 8 times more sensitive to complement than normal erythrocytes, demonstrating the link between CD59 deficiency and complement-mediated hemolysis. Shuchishima et al. (1999) "Complement sensitivity of erythrocytes in a patient with inherited complete deficiency of CD59 or with the Inab phenotype" *Brit J Haematol* 104: 303-306. Therefore, modulating the complement cascade and its components may ameliorate one or more symptoms suffered by subjects with CD59 deficiency.

Alzheimer's disease (AD) has been shown to be associated with persistent complement activation as both C1q and C3 recognize amyloid fibrils as foreign entities and induce continuous complement activation. Ricklin et al. (2010). The administration of a C5aR (the cell-surface receptor of C5a) antagonist to two mouse models of AD resulted in the reduction of amyloid deposits, an AD pathological hallmark, as well as improvements of memory performance. Fonseca et al. (2009) "Treatment with a C5aR antagonist decreases pathology and enhances behavioral performance in murine models of Alzheimer's disease" *J Immunol* 183(2): 1375-1383. Evidence suggests a strong association between complement activation and the pathogenesis of AD.

The restoration of blood flow to damaged tissue following an ischemic event can induce an inflammatory response known as ischemia-reperfusion injury. Yellon and Hausenloy (2007) "Myocardial reperfusion injury" *N Engl J Med* 357(11): 1121-1135. Evidence suggests that complement-mediated tissue damage can occur as a result of this inflammatory response. Diepenhorst et al. (2009) "Complement-mediated ischemia-reperfusion injury: lessons learned from animal and clinical studies" *Ann Surg* 249(6): 889-899. The inhibition of complement via the Crry gene, anti-C5 antibodies and Factor B antagonists in both rat and mouse models has been shown to be tissue protective. Diepenhorst et al. (2009). In addition, the genetic inactivation of C3 as well as C4 in mice has been shown to incur protective effects from local and remote injury in various ischemia reperfusion models of various organs. Diepenhorst et al. (2009). Evidence suggests a role of complement activation in ischemia reperfusion injury.

An association between serum C3 levels and the risk of myocardial infarction has been previously elucidated. During a 4-year follow-up study of individuals who had not previously suffered an ischemic event (including myocardial infarction, angina pectoris, stroke, transient ischemic attack or intermittent claudication), C3 levels were found to be independently associated with the occurrence of ischemic events. Muscari et al. (1995) "Association of serum C3 levels with the risk of myocardial infarction." *Am J Med* 98(4): 357-364. Therefore, complement C3 is a predictor of future ischemic events. In addition, complement C3 and C4 levels have been shown to be higher in patients with severe angiographically assessed atherosclerosis who had previously suffered ischemic events. Muscari et al. (1988) "Association of serum IgA and C4 with severe atherosclerosis" *Atherosclerosis* 74(1-2): 179-186. Atheroma development may be associated with the chronic activation of the complement system, since the occurrence of complement activation has been well documented in human atherosclerotic lesions. Seifert and Kazatchkine (1988) "The complement system in atherosclerosis" *Atherosclerosis* 73(2-3): 91-104. Therefore, complement system may play a role in coronary atherosclerosis and/or thrombosis.

Accordingly, there have been various attempts to inhibit or modulate the complement cascade and its components, which are believed to be associated with the pathogenic mechanisms of these various diseases and conditions. Various therapeutic formulations have been used for suppressing the complement system in the art, but such medicines increase the susceptibility to infections.

Anti-C5 antibodies have been shown to be effective in treating several diseases and disorders. For example, anti-C5 antibodies have been shown to reduce the clinical symptoms of PNH including blood transfusions, fatigue and abdominal pain. Ricklin and Lambris (2007). Anti-C5 antibodies have undergone preclinical and clinical testing for additional diseases including psoriasis, rheumatoid arthritis, SLE, and transplant rejection. Ricklin and Lambris (2007).

Cold agglutinin disease (CAD) involves immunoglobulin M (IgM)-mediated hemagglutination and robust complement activation. One study showed long-term efficacy in treating a patient with CAD with the complement inhibitor eculizumab, a humanized anti-C5 monoclonal antibody that blocks C5b-9 formation, the terminal event in the complement cascade. Roth et al. (2009) "Long-term efficacy of the complement inhibitor eculizumab in cold agglutinin disease" *Blood* 113(16): 3885-3886.

Compstatin, a small molecule inhibitor of the cleavage of C3 has been shown to be effective in preventing complement activation and associated inflammatory responses both in vivo and in vitro. Holland et al. (2004) "Synthetic small-molecule complement inhibitors" *Curr Opin Investig Drugs* 5(11): 1164-1173. For example, compstatin reduced hemolysis by 50% in an erythrocyte lysis animal model of the disease and prolonged graft survival in a porcine-to-human kidney perfusion animal model of the disease. Fiane et al. (1999) "Compstatin, a peptide inhibitor of C3, prolongs survival of ex vivo perfused pig xenografts" *Xenotransplantation* 6(1): 52-65.

Other potential targets for complement targeted therapeutics include protease inhibitors, small molecule complement regulators, therapeutic antibodies and complement protein inhibitors. Ricklin and Lambris (2013) "Progress and Trends in Complement Therapeutics" *Adv Exp Med Biol* 735: 1-22.

Given the strong involvement of complement in various inflammatory, immune and degenerative diseases, the potential vast array of targets for modulation, and the cascade organization allowing for multiple points of intervention, complement is an attractive target for therapeutic intervention. Ricklin and Lambris (2013). Current therapies are only approved for orphan indications including PNH, aHUS and hereditary angioedema, and therefore the potential for complement targeted therapies in more prevalent disease states exists. Ricklin and Lambris (2013).

The compounds disclosed in U.S. Pat. No. 8,053,440 have been shown to possess the ability to increase expression of apolipoprotein A-I (ApoA-I) and may be used as therapeutics for cardiovascular disease and cholesterol- or lipid-related disorders. Many of these same compounds have been described as possessing IL-6 and VCAM-1 inhibitory activity and may be used to treat or prevent inflammatory and autoimmune diseases and cancers. See WO2010/123975.

Surprisingly, the compounds of Formula I and Formula II also have the ability to modulate complement-associated diseases. Thus, one aspect of the invention provides methods of modulating the complement cascade in a mammal by administering one or more compounds of Formula I or Formula II or a stereoisomer, tautomer, pharmaceutically acceptable salt, or hydrate thereof. The invention also provides methods of treating or preventing complement-associated diseases by administering one or more compounds of Formula I or Formula II or a stereoisomer, tautomer, pharmaceutically acceptable salt, or hydrate thereof.

In some embodiments, the complement-associated disease is selected from atherosclerosis, membranous glomerulonephritis, asthma, organ transplantation rejection, thrombosis, deep vein thrombosis, disseminated venous thromboembolism, disseminated intravascular coagulation, and chronic obstructive pulmonary disease (COPD). In certain embodiments, the complement-associated disease is selected from paroxysmal nocturnal hemoglobinuria, atypical hemolytic uremic syndrome, amyotrophic lateral sclerosis, macular degeneration, lupus nephritis, myasthenia gravis, neuromyelitis optica, anti-phospholipid syndrome, catastrophic anti-phospholipid syndrome, dense deposit disease (type II membranoproliferative glomerulonephritis), Shiga-like toxin-producing *E. coli* hemolytic uremic syndrome, and abdominal and thoracic aortic aneurysms, and may be treated or prevented by administration of one or more compounds of Formula I or Formula II. In yet other embodiments, the complement-associated disease is selected from familial CD59 deficiency, cold agglutinin disease, familial C3 glomerulopathy, C3 glomerulonephritis, complement factor H related protein 5 nephropathy, IgA nephropathy, and hereditary angioedema (HAE).

DESCRIPTION OF EMBODIMENTS

Figure 1:
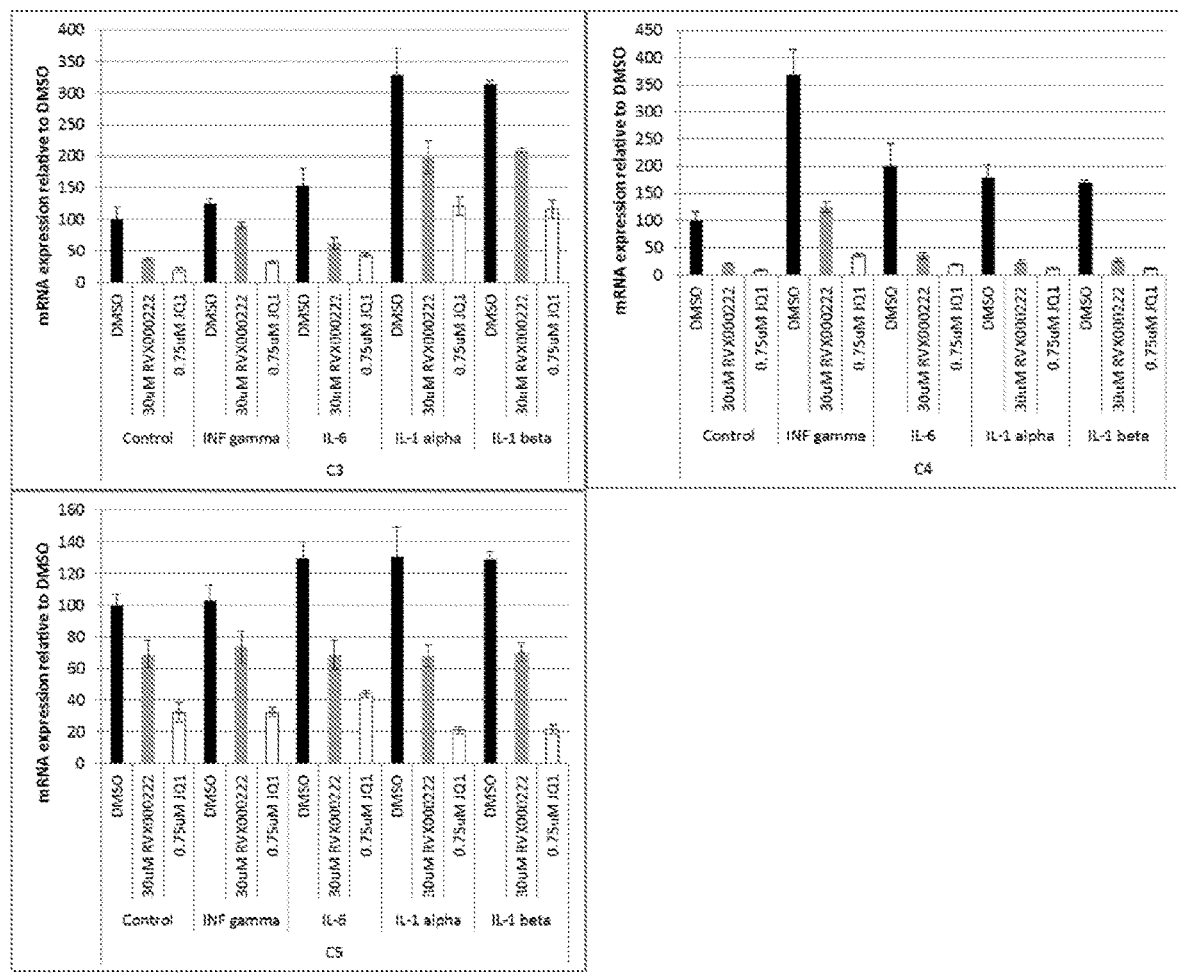
FIG. 1 demonstrates that RVX000222 reduces expression of complement component 3, 4 and 5 at the mRNA level in Huh-7 cells treated simultaneously with cytokines that induce complement expression during inflammation. mRNA level was determined by TaqMan real-time PCR and is normalized to the level of cyclophilin mRNA. Data is the mean of triplicate samples.
Figure 2:
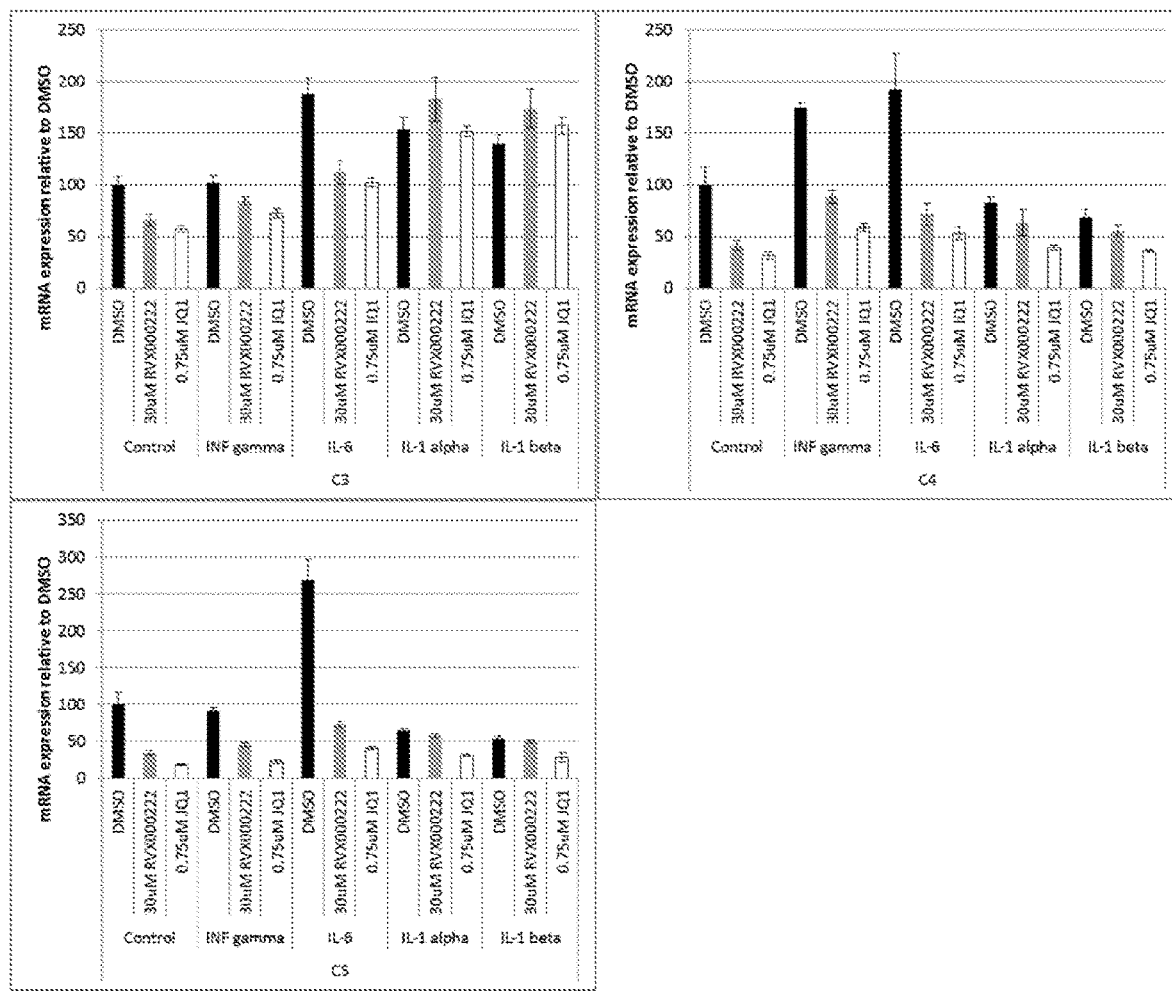
FIG. 2 demonstrates that RVX000222 reduces expression of complement component 3, 4 and 5 at the mRNA level in HepG2 cells treated simultaneously with cytokines that induce complement expression during inflammation. mRNA level was determined by TaqMan real-time PCR and is normalized to the level of cyclophilin mRNA. Data is the mean of triplicate samples.
Figure 3:
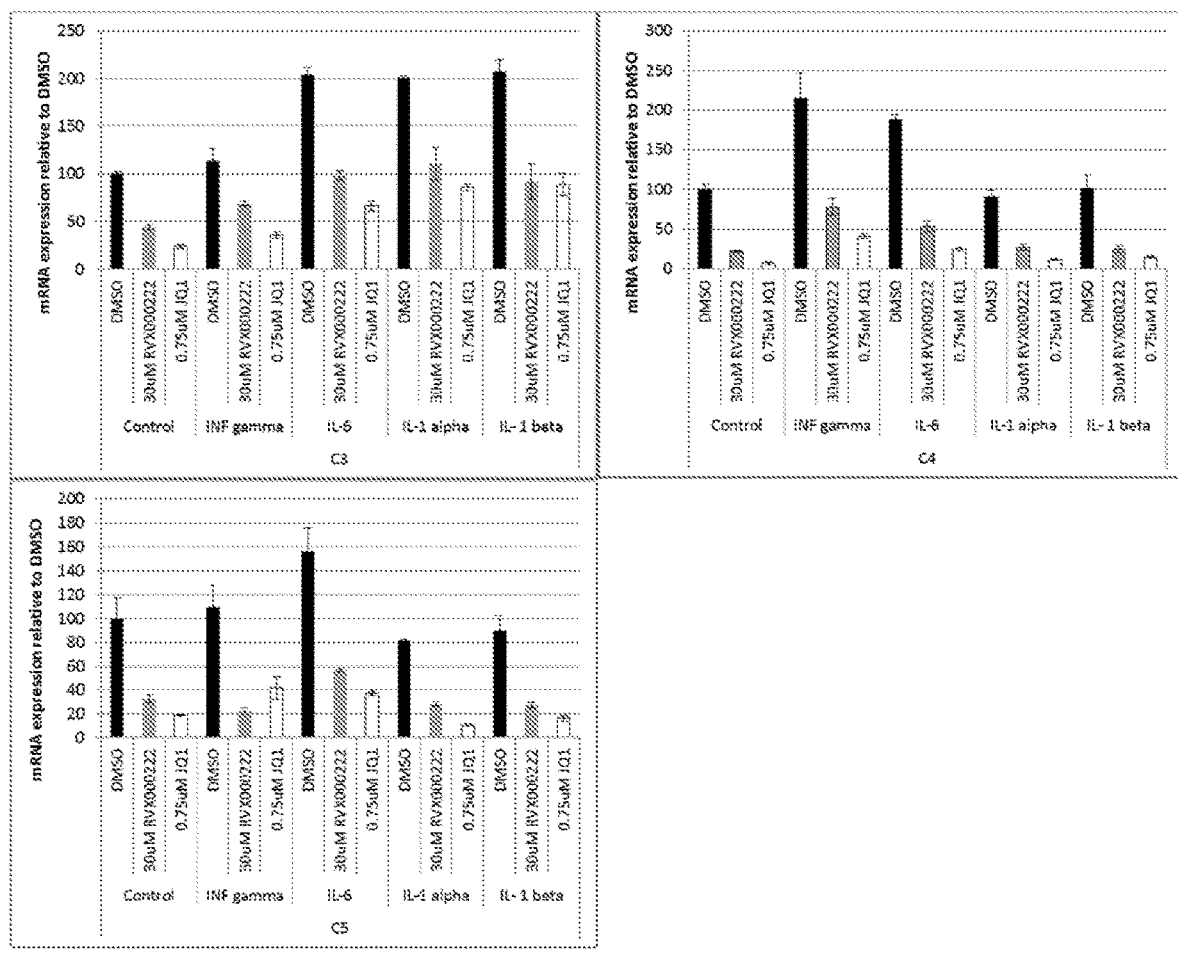
FIG. 3 RVX000222 reduces expression of complement component 3, 4 and 5 at the mRNA level in Huh-7 cells pre-treated with cytokines that induce complement expression during inflammation. mRNA level was determined by TaqMan real-time PCR and is normalized to the level of cyclophilin mRNA. Data is the mean of triplicate samples.
Figure 4:
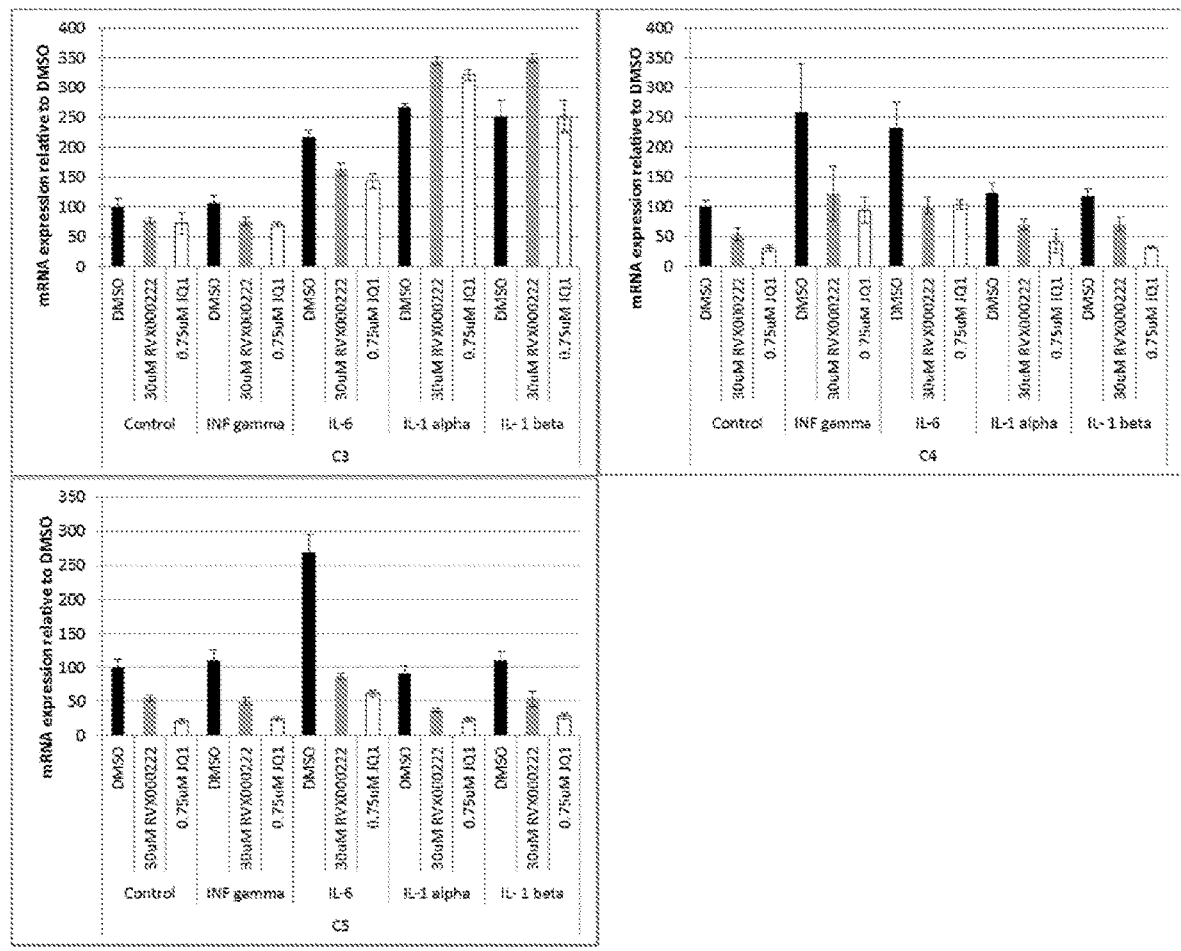
FIG. 4 RVX000222 reduces expression of complement component 3, 4 and 5 at the mRNA level in HepG2 cells pre-treated with cytokines that induce complement expression during inflammation. mRNA level was determined by TaqMan real-time PCR and is normalized to the level of cyclophilin mRNA. Data is the mean of triplicate samples.

In certain embodiments, the method for modulating the complement system in a subject in need thereof comprises administering a therapeutically effective amount of at least one compound of Formula I or Formula II as described herein or a stereoisomer, tautomer, pharmaceutically acceptable salt, or hydrate thereof.

In certain embodiments, the method for treating complement-associated diseases or disorders in a subject in need thereof comprises administering a therapeutically effective amount of at least one compound of Formula I or Formula II as described herein or a stereoisomer, tautomer, pharmaceutically acceptable salt, or hydrate thereof.

Definitions

As used in the present specification, the following words, phrases and symbols are generally intended to have the meanings as set forth below, except to the extent that the context in which they are used indicates otherwise. The following abbreviations and terms have the indicated meanings throughout:

The term "compound of Formula I" refers to compounds having the general structure:

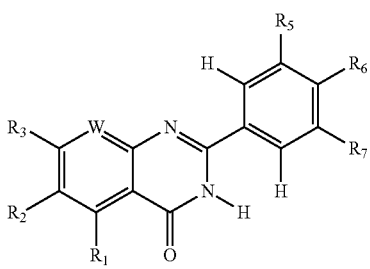

Formula I or a stereoisomer, tautomer, pharmaceutically acceptable salt, or hydrate thereof,
wherein:
$R_1$ and $R_3$ are each independently selected from alkoxy, alkyl, amino, halogen, and hydrogen;
$R_2$ is selected from alkoxy, alkyl, alkenyl, alkynyl, amide, amino, halogen, and hydrogen;
$R_5$ and $R_7$ are each independently selected from alkyl, alkoxy, amino, halogen, and hydrogen;
$R_6$ is selected from amino, amide, alkyl, hydrogen, hydroxyl, piperazinyl, and alkoxy, wherein the alkoxy is optionally substituted with one or more groups chosen from amide, amine, aryl, benzyloxy, carbamate, carboxy, heterocyclyl, hydroxyl, methoxy, and sulfonamide; and
W is CH or N.

In some embodiments, W is CH in the compound of Formula I or a stereoisomer, tautomer, pharmaceutically acceptable salt, or hydrate thereof, and $R_1$, $R_2$, $R_3$, $R_5$, $R_6$, and $R_7$, are as defined in the foregoing paragraph.

In some embodiments, $R_6$ in the compound of Formula I or a stereoisomer, tautomer, pharmaceutically acceptable salt, or hydrate thereof, is selected from alkoxy optionally substituted with one or more groups chosen from amide, amine, aryl, benzyloxy, carbamate, carboxy, heterocyclyl, hydroxyl, methoxy, and sulfonamide, and $R_1$, $R_2$, $R_3$, $R_5$, $R_7$, and W are as defined in any of the two foregoing paragraphs.

In some embodiments, $R_6$ in the compound of Formula I or a stereoisomer, tautomer, pharmaceutically acceptable salt, or hydrate thereof, is selected from hydrogen, methoxy,

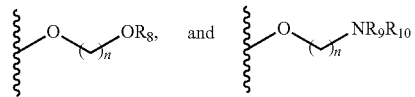

wherein
n is 1, 2, or 3;
$R_8$ is selected from hydrogen or $C_1$-$C_6$ alkyl substituted with one or more groups selected from methyl, phenyl, and pyridinyl;
$R_9$ and $R_{10}$ are independently selected from unsubstituted $C_1$-$C_6$ alkyl, wherein $R_9$ and $R_{10}$ may be joined together with N to form a 3- to 12-membered ring; and
$R_1$, $R_2$, $R_3$, $R_5$, $R_7$, and W are as defined above for the compound Formula I or a stereoisomer, tautomer, pharmaceutically acceptable salt, or hydrate thereof.

In some embodiments, $R_6$ in the compound of Formula I or a stereoisomer, tautomer, pharmaceutically acceptable salt, or hydrate thereof, is selected from 2-(hydroxy)ethoxy, 2-(pyrrolidin-1-yl)ethoxy, 4-isopropylpiperazin-1-yl, and 2-(isopropylamino)ethoxy, and $R_1$, $R_2$, $R_3$, $R_5$, $R_7$, and W are as defined above for the compound of Formula I or a stereoisomer, tautomer, pharmaceutically acceptable salt, or hydrate thereof.

In some embodiments, $R_6$ in the compound of Formula I or a stereoisomer, tautomer, pharmaceutically acceptable salt, or hydrate thereof, is 2-(hydroxy)ethoxy, and $R_1$, $R_2$, $R_3$, $R_5$, $R_7$, and W are as defined above for the compound of Formula I or a stereoisomer, tautomer, pharmaceutically acceptable salt, or hydrate thereof.

In some embodiments, $R_1$ and $R_3$ in the compound of Formula I or a stereoisomer, tautomer, pharmaceutically acceptable salt, or hydrate thereof, are both methoxy, $R_2$, $R_5$, $R_6$, $R_7$, $R_8$, $R_9$, $R_{10}$, and W are as defined above for the compound of Formula I or a stereoisomer, tautomer, pharmaceutically acceptable salt, or hydrate thereof.

In some embodiments, the compound of Formula I is selected from:
2-(4-(2-hydroxyethoxy)-3,5-dimethylphenyl)-5,7-dimethoxyquinazolin-4(3H)-one;
2-{3,5-dimethyl-4-[2-(pyrrolidin-1-yl)ethoxy]phenyl}-5,7-di methoxy-3,4-dihydroquinazolin-4-one;
2-(3,5-dimethyl-4-{2-[(propan-2-yl)amino]ethoxy}phenyl)-5,7-dimethoxy-3,4-dihydroquinazolin-4-one;
5,7-dimethoxy-2-{4-[4-(propan-2-yl)piperazin-1-yl]phenyl}-3,4-dihydroquinazolin-4-one;
5,7-dimethoxy-2-{3-methoxy-5-[2-(pyrrolidin-1-yl)ethoxy]phenyl}-3,4-dihydroquinazolin-4-one;
2-{3,5-dimethyl-4-[2-(pyrrolidin-1-yl)ethoxy]phenyl}-5,7-di methoxy-3H,4H-pyrido[2,3-d]pyrimidin-4-one;
2-{4-[2-(3,3-difluoropyrrolidin-1-yl)ethoxy]-3,5-dimethylphenyl}-5,7-dimethoxy-3,4-dihydroquinazolin-4-one;
N-{2-[4-(5,7-dimethoxy-4-oxo-3,4-dihydroquinazolin-2-yl)-2,6-dimethylphenoxy]ethyl}-2-methylpropanamide;
5,7-dimethoxy-2-[4-(piperazin-1-yl)phenyl]-3,4-dihydroquinazolin-4-one;
2-(4-hydroxy-3,5-dimethylphenyl)-5,7-dimethoxy-3,4-dihydroquinazolin-4-one;
N-{2-[4-(5,7-dimethoxy-4-oxo-3,4-dihydroquinazolin-2-yl)-2,6-dimethylphenoxy]ethyl}acetamide;
methyl N-{2-[4-(5,7-dimethoxy-4-oxo-3,4-dihydroquinazolin-2-yl)-2,6-dimethylphenoxy]ethyl}carbamate;
2-[4-(2,3-di hydroxypropoxy)-3,5-dimethylphenyl]-5,7-dimethoxy-3,4-dihydroquinazolin-4-one;
N-(2-(4-(5,7-Dimethoxy-4-oxo-3,4-dihydroquinazolin-2-yl)-2,6-dimethylphenoxy)ethyl)-4-methylbenzamide;
2-(4-(5,7-Dimethoxy-4-oxo-3,4-dihydroquinazolin-2-yl)-2,6-dimethyl-phenoxy)ethyl methylcarbamate;
2-(4-(5,7-Dimethoxy-4-oxo-3,4-dihydroquinazolin-2-yl)-2,6-dimethyl-phenoxy)ethyl propylcarbamate;
N-(2-(4-(5,7-dimethoxy-4-oxo-3,4-dihydroquinazolin-2-yl)-2,6-dimethylphenoxy)ethyl)methanesulfonamide (RVX002093);
4-chloro-N-(2-(4-(5,7-dimethoxy-4-oxo-3,4-dihydroquinazolin-2-yl)-2,6-dimethylphenoxy)ethyl)benzenesulfonamide;
N-(2-(4-(5,7-dimethoxy-4-oxo-3,4-dihydroquinazolin-2-yl)-2,6-dimethylphenoxy)ethyl)-4-methoxybenzenesulfonamide;
2-(4-(2-aminoethoxy)-3,5-dimethylphenyl)-5,7-dimethoxyquinazolin-4(3H)-one;
$N^1$-(2-(4-(5,7-dimethoxy-4-oxo-3,4-dihydroquinazolin-2-yl)-2,6-dimethylphenoxy)ethyl)-$N^2$-methylphthalamide;
2-(4-(2-hydroxyethoxy)-3-methylphenyl)-5,7-dimethoxyquinazolin-4(3H)-one;
2-(4-(benzyloxy)-3,5-dimethylphenyl)-5,7-dimethoxyquinazolin-4(3H)-one;

6-bromo-2-(4-(2-hydroxyethoxy)-3,5-dimethylphenyl)quinazolin-4(3H)-one;
6-bromo-2-(4-hydroxy-3,5-dimethylphenyl)quinazolin-4(3H)-one;
2-(4-(2-hydroxyethoxy)-3,5-dimethylphenyl)-6-methoxyquinazolin-4(3H)-one;
5,7-dichloro-2-(4-(2-hydroxyethoxy)-3,5-dimethylphenyl)quinazolin-4(3H)-one;
5,7-dimethoxy-2-(4-(2-methoxyethoxy)-3,5-dimethylphenyl)quinazolin-4(3H)-one;
N-(2-(4-(2-hydroxyethoxy)-3,5-dimethylphenyl)-4-oxo-3,4-dihydroquinazolin-6-yl)acetamide;
2-(4-(2-hydroxyethoxy)-3,5-dimethylphenyl)-5,7-dimethoxypyrido[2,3-d]pyrimidin-4(3H)-one;
5,7-dimethoxy-2-(4-methoxy-3-(morpholinomethyl)phenyl)quinazolin-4(3H)-one;
2-(4-((4-ethylpiperazin-1-yl)methyl)phenyl)-5,7-dimethoxyquinazolin-4(3H)-one;
5,7-dimethoxy-2-(4-(morpholinomethyl)phenyl)quinazolin-4(3H)-one;
N-(4-(5,7-dimethoxy-4-oxo-3,4-dihydroquinazolin-2-yl)phenyl)-2-hydroxyacetamide;
2-(4-(5,7-dimethoxy-4-oxo-3,4-dihydroquinazolin-2-yl)-2,6-dimethylphenoxy)acetic acid; N-(4-(5,7-di methoxy-4-oxo-3,4-dihydroquinazolin-2-yl)-2,6-dimethylphenyl)-2-hydroxyacetamide;
5,7-dimethoxy-2-(4-((4-methylpiperazin-1-yl)methyl)phenyl)quinazolin-4(3H)-one;
2-(4-(2-hydroxyethoxy)-3,5-dimethylphenyl)-6,7-dimethoxyquinazolin-4(3H)-one;
2-(4-(2-hydroxyethoxy)-3-methoxyphenyl)-5,7-dimethoxyquinazolin-4(3H)-one;
2-(3-chloro-4-(2-hydroxyethoxy)phenyl)-5,7-dimethoxyquinazolin-4(3H)-one;
2-(4-(6,7-dimethoxy-4-oxo-3,4-dihydroquinazolin-2-yl)-2,6-dimethylphenoxy)acetamide;
N-(2-(4-hydroxy-3,5-dimethylphenyl)-4-oxo-3,4-dihydroquinazolin-6-yl)acetamide;
2-(4-(bis(2-hydroxyethyl)amino)phenyl)-6,7-dimethoxyquinazolin-4(3H)-one;
2-(4-(bis(2-hydroxyethyl)amino)phenyl)-5,7-dimethoxyquinazolin-4(3H)-one;
5,7-dimethoxy-2-(4-(4-methylpiperazin-1-yl)phenyl)quinazolin-4(3H)-one (RVX000255);
2-(4-(2-hydroxyethoxy)-3,5-dimethylphenyl)quinazolin-4(3H)-one;
2-(3,5-dimethyl-4-(2-morpholinoethoxy)phenyl)quinazolin-4(3H)-one;
2-(3,5-dimethyl-4-(2-morpholinoethoxy)phenyl)-5,7-dimethoxyquinazolin-4(3H)-one; and
stereoisomers, tautomers, pharmaceutically acceptable salts, and hydrates thereof.

In some embodiments, the compound of Formula I is 2-(4-(2-hydroxyethoxy)-3,5-dimethylphenyl)-5,7-dimethoxyquinazolin-4(3H)-one (RVX000222) (also known as RVX-208)

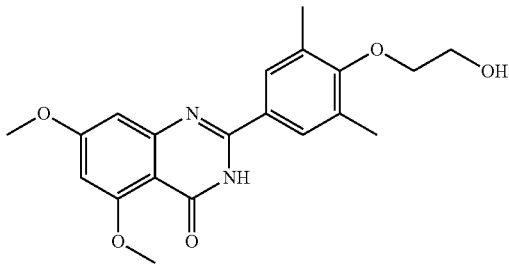 [SMILES: COc1cc(OC)c2c(=O)[nH]c(-c3cc(C)c(OCCO)c(C)c3)nc2c1]

or a stereoisomer, tautomer, pharmaceutically acceptable salt, or hydrate thereof.

In certain embodiments, the compound of Formula I is 2-{3,5-dimethyl-4-[2-(pyrrolidin-1-yl)ethoxy]phenyl}-5,7-dimethoxy-3,4-dihydroquinazolin-4-one

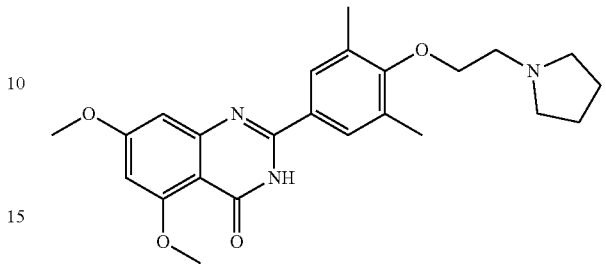

(RVX000297)

or a stereoisomer, tautomer, pharmaceutically acceptable salt, or hydrate thereof.

In other embodiments, the compound of Formula I is 2-(3,5-dimethyl-4-{2-[(propan-2-yl)amino]ethoxy}phenyl)-5,7-dimethoxy-3,4-dihydroquinazolin-4-one

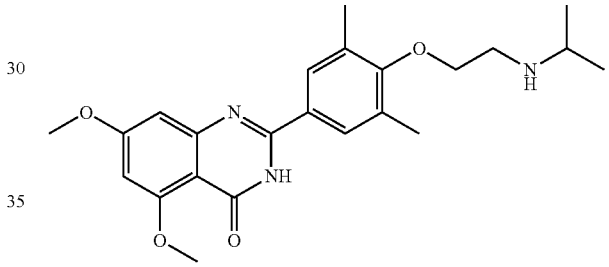

(RVX002135)

or a stereoisomer, tautomer, pharmaceutically acceptable salt, or hydrate thereof.

In yet other embodiments, the compound of Formula I is 5,7-dimethoxy-2-{4-[4-(propan-2-yl)piperazin-1-yl]phenyl}-3,4-dihydroquinazolin-4-one

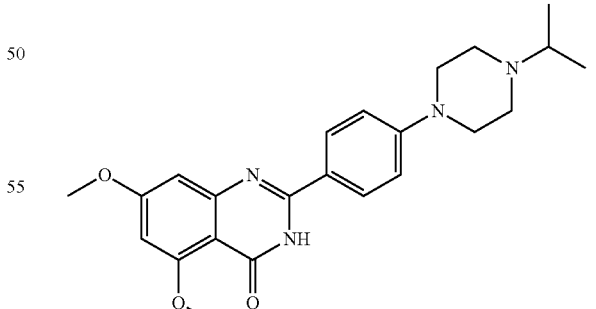

(RVX002109)

or a stereoisomer, tautomer, pharmaceutically acceptable salt, or hydrate thereof.

In some embodiments, the compound of Formula I is 5,7-dimethoxy-2-{3-methoxy-5-[2-(pyrrolidin-1-yl)ethoxy]phenyl}-3,4-dihydroquinazolin-4-one (RVX000641)

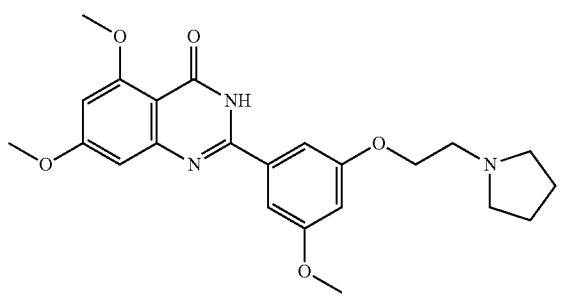

or a stereoisomer, tautomer, pharmaceutically acceptable salt, or hydrate thereof.

In some embodiments, the compound of Formula I is 2-{3,5-dimethyl-4-[2-(pyrrolidin-1-yl)ethoxy]phenyl}-5,7-dimethoxy-3H,4H-pyrido[2,3-d]pyrimidin-4-one (RVX000662)

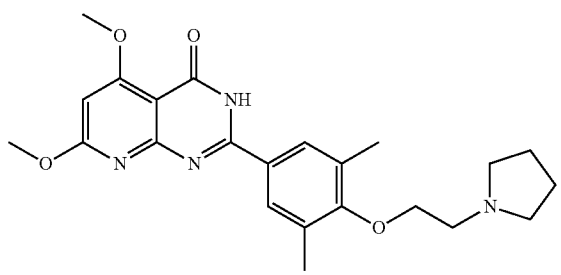

or a stereoisomer, tautomer, pharmaceutically acceptable salt, or hydrate thereof.

In some embodiments, the compound is 2-{2-[(dimethylamino)methyl]-1H-indol-5-yl}-5,7-dimethoxy-3,4-dihydroquinazolin-4-one (RVX000668)

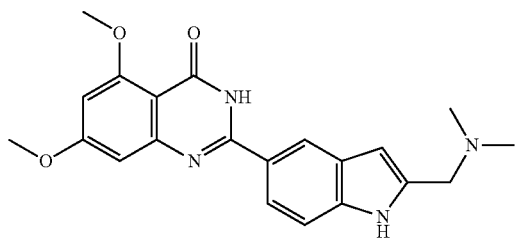

or a stereoisomer, tautomer, pharmaceutically acceptable salt, or hydrate thereof.

In some embodiments, the compound of Formula I is 2-{4-[2-(3,3-difluoropyrrolidin-1-yl)ethoxy]-3,5-dimethylphenyl}-5,7-dimethoxy-3,4-dihydroquinazolin-4-one (RVX000843)

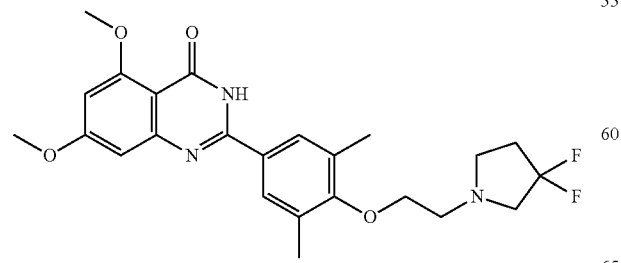

or a stereoisomer, tautomer, pharmaceutically acceptable salt, or hydrate thereof.

In some embodiments, the compound of Formula I is N-{2-[4-(5,7-dimethoxy-4-oxo-3,4-dihydroquinazolin-2-yl)-2,6-dimethylphenoxy]ethyl}-2-methylpropanamide (RVX002103)

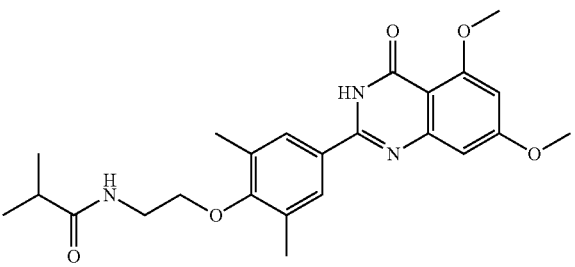

or a stereoisomer, tautomer, pharmaceutically acceptable salt, or hydrate thereof.

In some embodiments, the compound of Formula I is 5,7-dimethoxy-2-[4-(piperazin-1-yl)phenyl]-3,4-dihydroquinazolin-4-one (RVX002141)

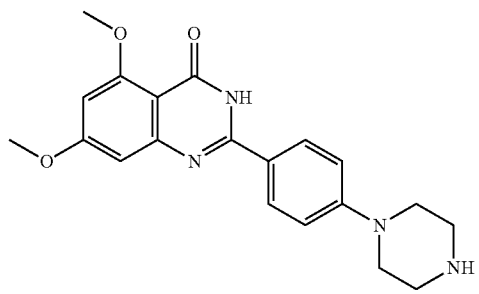

or a stereoisomer, tautomer, pharmaceutically acceptable salt, or hydrate thereof.

In some embodiments, the compound of Formula I is 2-(4-hydroxy-3,5-dimethylphenyl)-5,7-dimethoxy-3,4-dihydroquinazolin-4-one (RVX000206)

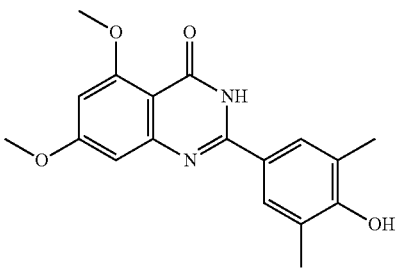

or a stereoisomer, tautomer, pharmaceutically acceptable salt, or hydrate thereof.

In some embodiments, the compound of Formula I is N-{2-[4-(5,7-dimethoxy-4-oxo-3,4-dihydroquinazolin-2-yl)-2,6-dimethylphenoxy]ethyl}acetamide (RVX002101)

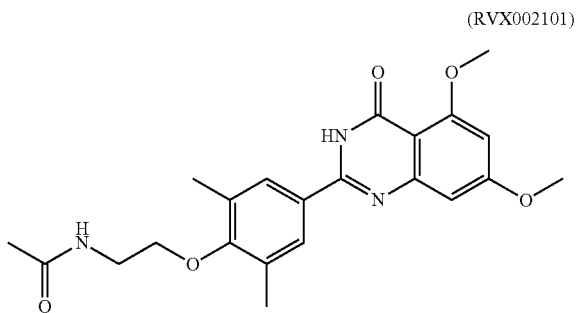 [SMILES: COc1cc(OC)c2c(=O)[nH]c(-c3cc(C)c(OCCNC(C)=O)c(C)c3)nc2c1]

or a stereoisomer, tautomer, pharmaceutically acceptable salt, or hydrate thereof.

In some embodiments, the compound of Formula I is methyl N-{2-[4-(5,7-dimethoxy-4-oxo-3,4-dihydroquinazolin-2-yl)-2,6-dimethylphenoxy]ethyl}carbamate (RVX002113)

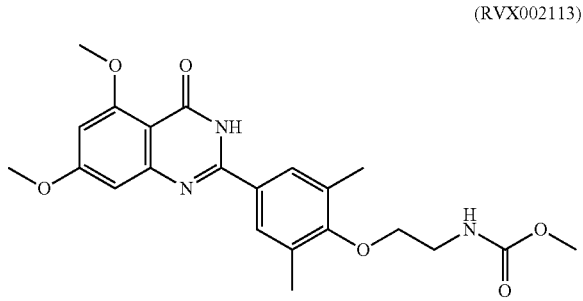

or a stereoisomer, tautomer, pharmaceutically acceptable salt, or hydrate thereof.

In some embodiments, the compound of Formula I is 2-[4-(2,3-dihydroxypropoxy)-3,5-dimethylphenyl]-5,7-dimethoxy-3,4-dihydroquinazolin-4-one (RVX000344)

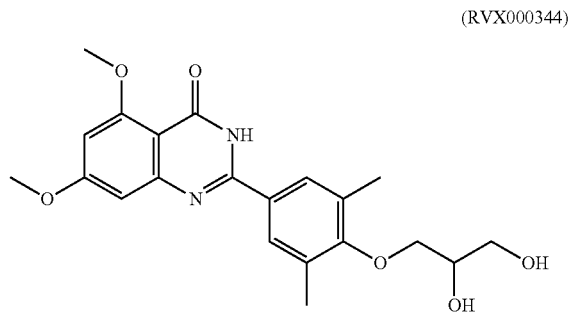 [SMILES: COc1cc(OC)c2c(=O)[nH]c(-c3cc(C)c(OCC(O)CO)c(C)c3)nc2c1]

or a stereoisomer, tautomer, pharmaceutically acceptable salt, or hydrate thereof.

The term "compound of Formula II" refers to compounds having the general structure:

Formula II

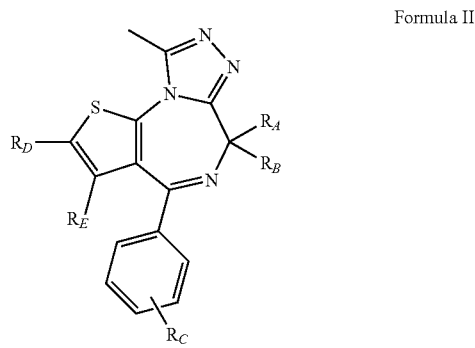

or a stereoisomer, tautomer, pharmaceutically acceptable salt, or hydrate thereof, wherein:

$R_A$ and $R_B$ are independently selected from hydrogen, methyl, —$(CH_2)_nR_F$, —$(CH_2)_nOR_F$, and —$CH_2C(O)OR_G$;

$R_C$ is selected from hydrogen, para-halogen, and —$OCH_2O$— or —$OCH_2CH_2O$— connected to the ortho and meta positions or connected to the meta and para positions of the phenyl ring;

$R_D$ and $R_E$ are independently selected from hydrogen and methyl;

$R_F$ is selected from methyl, ethyl, and —$CH_2CH_2OCH_3$;

$R_G$ is selected from methyl, Ethyl, n-propyl, isopropyl, n-butyl, and tert-butyl; and n is selected from 1, 2, 3, and 4.

In some embodiments, $R_C$ is para-Cl.

In some embodiments, the compound of Formula II is selected from:

6,6-dimethyl-4-phenyl-9-methyl-6H-thieno[3,2-f]-s-triazolo[4,3-a][1,4]diazepine;

4-(3',4'-mehylenedioxyphenyl)-9-methyl-6H-thieno[3,2-f]-s-triazolo[4,3-a][1,4]diazepine;

9-methyl-4-phenyl-6H-thieno[3,2-f]-s-triazolo[4,3-a][1,4]diazepine;

(S)-tert-butyl 2-(4-(4-chlorophenyl)-2,3,9-trimethyl-6H-thieno[3,2-f][1,2,4]triazolo[4,3-a][1,4]diazepin-6-yl)acetate (JQ1);

and stereoisomers, tautomers, pharmaceutically acceptable salts, and hydrates thereof.

In some embodiments, the compound of Formula I or Formula II is in the form of a solvate. In some embodiments, the compound of Formula I or Formula II is in the form of a hydrate. In some embodiments, the compound of Formula I or Formula II is in the form of a chelate. In some embodiments, the compound of Formula I or Formula II is in the form of a pharmaceutically acceptable salt. In some embodiments, the compound of Formula I or Formula II is in crystalline form. In some embodiments, the compound of Formula I or Formula II is a polymorph or a pseudopolymorph. In some embodiments, the compound of Formula I or Formula II is in the form of an unsolvated polymorph, such as, e.g., an anhydrate. In some embodiments, the compound of Formula I or Formula II is in the form of a conformational polymorph. In some embodiments, the compound of Formula I or Formula II is amorphous. In some embodiments, the compound of Formula I or Formula II is in the form of a non-covalent complex. In some embodiments, the compound of Formula I or Formula II is in the form of a solvate of a salt. In some embodiments, the compound of Formula I or Formula II is in the form of a chelate of a salt. In some embodiments, the compound of Formula I or Formula II is in the form of a hemi-hydrate. In some embodiments, the compound of Formula I or Formula II is in the form of a monohydrate.

In some embodiments, a "prodrug" is administered to a patient to become a compound of Formula I or Formula II or a stereoisomer, tautomer, pharmaceutically acceptable salt, or hydrate thereof, e.g., upon metabolic processing of the prodrug. Examples of prodrugs include derivatives of functional groups, such as a carboxylic acid group, in the compounds of Formula I or Formula II. Exemplary prodrugs of a carboxylic acid group include, but are not limited to, carboxylic acid esters such as alkyl esters, hydroxyalkyl esters, arylalkyl esters, and aryloxyalkyl esters.

A "solvate" is formed by the interaction of a solvent and a compound, and the compounds of Formula I or Formula II may be in the form of a solvate. Similarly, a "salt" of the compounds of Formula I or Formula II may be in the form of a solvate of salt. Suitable solvates are pharmaceutically acceptable solvates, such as hydrates, including monohydrates and hemi-hydrates.

A "chelate" is formed by the coordination of a compound to a metal ion at two (or more) points. The compound of Formula I or Formula II may be in the form of a chelate. Similarly, a salt of a compound of Formula I or Formula II may be in the form of a chelate.

A "non-covalent complex" may be formed by the interaction of a compound of Formula I or Formula II and another molecule wherein a covalent bond is not formed between the compound and the molecule. For example, complexation can occur through van der Waals interactions, hydrogen bonding, and electrostatic interactions (also called ionic bonding).

A dash ("-") that is not between two letters or symbols is used to indicate a point of attachment for a substituent. For example, —$CONH_2$ is attached through the carbon atom.

By "optional" or "optionally" is meant that the subsequently described event or circumstance may or may not occur, and that the description includes instances where the event or circumstance occurs and instances in which is does not. For example, "optionally substituted aryl" encompasses both "aryl" and "substituted aryl" as defined below. It will be understood by those skilled in the art, with respect to any group containing one or more substituents, that such groups are not intended to introduce any substitution or substitution patterns that are sterically impractical, synthetically nonfeasible and/or inherently unstable.

The term "acyl" term as used herein refers to a carbonyl radical attached to an alkyl, alkenyl, alkynyl, cycloalkyl, heterocycyl, aryl, or heteroaryl. Exemplary acyl groups include, but are not limited to, acetyl, formyl, propionyl, benzoyl, and the like.

The term "aldehyde" or "formyl" as used herein refers to —CHO.

The term "alkenyl" as used herein refers to an unsaturated straight or branched hydrocarbon having at least one carbon-carbon double bond, such as a straight or branched group of 2-22, 2-8, or 2-6 carbon atoms, referred to herein as ($C_2$-$C_{22}$)alkenyl, ($C_2$-$C_8$)alkenyl, and ($C_2$-$C_6$)alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, and 4-(2-methyl-3-butene)-pentenyl.

The term "alkoxy" as used herein refers to an alkyl group attached to an oxygen (—O-alkyl-). "Alkoxy" groups also include an alkenyl group attached to an oxygen ("alkenyloxy") or an alkynyl group attached to an oxygen ("alkynyloxy") groups. Exemplary alkoxy groups include, but are not limited to, groups with an alkyl, alkenyl or alkynyl group of 1-22, 1-8, or 1-6 carbon atoms, referred to herein as ($C_1$-$C_{22}$)alkoxy, ($C_1$-$C_8$)alkoxy, and ($C_1$-$C_6$)alkoxy, respectively. Exemplary alkoxy groups include, but are not limited to methoxy and ethoxy.

The term "alkyl" as used herein refers to a saturated straight or branched hydrocarbon, such as a straight or branched group of 1-22, 1-8, or 1-6 carbon atoms, referred to herein as ($C_1$-$C_2$)alkyl, ($C_1$-$C_8$)alkyl, and ($C_1$-$C_6$)alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl.

The term "alkynyl" as used herein refers to an unsaturated straight or branched hydrocarbon having at least one carbon-carbon triple bond, such as a straight or branched group of 2-22, 2-8, or 2-6 carbon atoms, referred to herein as ($C_2$-$C_{22}$)alkynyl, ($C_2$-$C_8$)alkynyl, and ($C_2$-$C_6$)alkynyl, respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl.

The term "amide" as used herein refers to the structure —$NR_aC(O)(R_b)$— or —$C(O)NR_bR_c$, wherein $R_a$, $R_b$ and $R_c$ are each independently selected from alkyl, alkenyl, alkynyl, aryl, arylalkyl, cycloalkyl, haloalkyl, heteroaryl, heterocyclyl, and hydrogen. The amide can be attached to another group through the carbon, the nitrogen, $R_b$, or $R_c$. The amide also may be cyclic, for example $R_b$ and $R_c$, may be joined to form a 3- to 12-membered ring, such as a 3- to 10-membered ring or a 5- or 6-membered ring. The term "amide" encompasses groups such as sulfonamide, urea, ureido, carbamate, carbamic acid, and cyclic versions thereof. The term "amide" also encompasses an amide group attached to a carboxy group, e.g., -amide-COOH or salts such as -amide-COONa, an amino group attached to a carboxy group (e.g., -amino-COOH or salts such as -amino-COONa).

The term "amine" or "amino" as used herein refers to the structure —$NR_dR_e$ or —$N(R_d)R_e$—, where $R_d$ and $R_e$ are independently selected from alkyl, alkenyl, alkynyl, aryl, arylalkyl, carbamate, cycloalkyl, haloalkyl, heteroaryl, heterocyclyl, and hydrogen. The amino can be attached to the parent molecular group through the nitrogen. The amino also may be cyclic, for example any two of $R_d$ and $R_e$ may be joined together or with the N to form a 3- to 12-membered ring (e.g., morpholino or piperidinyl). The term amino also includes the corresponding quaternary ammonium salt of any amino group. Exemplary amino groups include alkylamino groups, wherein at least one of $R_d$ or $R_e$ is an alkyl group.

The term "aryl" as used herein refers to a mono-, bi-, or other multi-carbocyclic, aromatic ring system. The aryl group can optionally be fused to one or more rings selected from aryls, cycloalkyls, and heterocyclyls. The aryl groups of this invention can be substituted with groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "($C_6$)aryl."

The term "arylalkyl" as used herein refers to an alkyl group having at least one aryl substituent (e.g., -aryl-alkyl-). Exemplary arylalkyl groups include, but are not limited to, arylalkyls having a monocyclic aromatic ring system, wherein the ring comprises 6 carbon atoms, referred to herein as "($C_6$)arylalkyl."

The term "aryloxy" as used herein refers to an aryl group attached to an oxygen atom. Exemplary aryloxy groups include, but are not limited to, aryloxys having a monocyclic aromatic ring system, wherein the ring comprises 6 carbon atoms, referred to herein as "($C_6$)aryloxy."

The term "arylthio" as used herein refers to an aryl group attached to an sulfur atom. Exemplary arylthio groups include, but are not limited to, arylthios having a monocyclic aromatic ring system, wherein the ring comprises 6 carbon atoms, referred to herein as "($C_6$)arylthio."

The term "arylsulfonyl" as used herein refers to an aryl group attached to a sulfonyl group, e.g., —S(O)$_2$-aryl-. Exemplary arylsulfonyl groups include, but are not limited to, arylsulfonyls having a monocyclic aromatic ring system, wherein the ring comprises 6 carbon atoms, referred to herein as "($C_6$)arylsulfonyl."

The term "benzyl" as used herein refers to the group —CH$_2$-phenyl.

The term "bicyclic aryl" as used herein refers to an aryl group fused to another aromatic or non-aromatic carbocyclic or heterocyclic ring. Exemplary bicyclic aryl groups include, but are not limited to, naphthyl or partly reduced forms thereof, such as di-, tetra-, or hexahydronaphthyl.

The term "bicyclic heteroaryl" as used herein refers to a heteroaryl group fused to another aromatic or non-aromatic carbocyclic or heterocyclic ring. Exemplary bicyclic heteroaryls include, but are not limited to 5,6- or 6,6-fused systems, wherein one or both rings contain heteroatoms. The term "bicyclic heteroaryl" also encompasses reduced or partly reduced forms of fused aromatic system wherein one or both rings contain ring heteroatoms. The ring system may contain up to three heteroatoms, independently selected from oxygen, nitrogen, and sulfur. The bicyclic system may be optionally substituted with one or more groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Exemplary bicyclic heteroaryl's include, but are not limited to, quinazolinyl, benzothiophenyl, benzoxazolyl, benzimidazolyl, benzothiazolyl, benzofuranyl, indolyl, quinolinyl, isoquinolinyl, phthalazinyl, benzotriazolyl, benzopyridinyl, and benzofuranyl.

The term "carbamate" as used herein refers to the form —R$_g$OC(O)N(R$_h$)—, —R$_g$OC(O)N(R$_h$)R$_i$—, or —OC(O)NR$_h$R$_i$, wherein R&, R$_h$ and R$_i$ are each independently selected from alkyl, alkenyl, alkynyl, aryl, arylalkyl, cycloalkyl, haloalkyl, heteroaryl, heterocyclyl, and hydrogen. Exemplary carbamates include, but are not limited to, arylcarbamates or heteroaryl carbamates (e.g., wherein at least one of R$_g$, R$_h$ and R$_i$ are independently selected from aryl or heteroaryl, such as pyridine, pyridazine, pyrimidine, and pyrazine).

The term "carbonyl" as used herein refers to —C(O)—.

The term "carboxy" as used herein refers to —COOH or its corresponding carboxylate salts (e.g., —COONa). The term carboxy also includes "carboxycarbonyl," e.g. a carboxy group attached to a carbonyl group, e.g., —C(O)—COOH or salts, such as —C(O)—COONa.

The term "cyano" as used herein refers to —CN.

The term "cycloalkoxy" as used herein refers to a cycloalkyl group attached to an oxygen.

The term "cycloalkyl" as used herein refers to a saturated or unsaturated cyclic, bicyclic, or bridged bicyclic hydrocarbon group of 3-12 carbons, or 3-8 carbons, referred to herein as "($C_3$-$C_8$)cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Cycloalkyl groups can be fused to other cycloalkyl saturated or unsaturated, aryl, or heterocyclyl groups.

The term "dicarboxylic acid" as used herein refers to a group containing at least two carboxylic acid groups such as saturated and unsaturated hydrocarbon dicarboxylic acids and salts thereof. Exemplary dicarboxylic acids include alkyl dicarboxylic acids. Dicarboxylic acids may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone. Dicarboxylic acids include, but are not limited to succinic acid, glutaric acid, adipic acid, suberic acid, sebacic acid, azelaic acid, maleic acid, phthalic acid, aspartic acid, glutamic acid, malonic acid, fumaric acid, (+)/(−)-malic acid, (+)/(−) tartaric acid, isophthalic acid, and terephthalic acid. Dicarboxylic acids further include carboxylic acid derivatives thereof, such as anhydrides, imides, hydrazides (for example, succinic anhydride and succinimide).

The term "ester" refers to the structure —C(O)O—, —C(O)O—R$_j$-, —R$_k$C(O)O—R$_j$—, or —R$_k$C(O)O—, where 0 is not bound to hydrogen, and R$_j$ and R$_k$ can independently be selected from alkoxy, aryloxy, alkyl, alkenyl, alkynyl, amide, amino, aryl, arylalkyl, cycloalkyl, ether, haloalkyl, heteroaryl, and heterocyclyl. R$_k$ can be a hydrogen, but R$_j$ cannot be hydrogen. The ester may be cyclic, for example the carbon atom and R$_j$, the oxygen atom and R$_k$, or R$_j$ and R$_k$ may be joined to form a 3- to 12-membered ring. Exemplary esters include, but are not limited to, alkyl esters wherein at least one of R$_j$ or R$_k$ is alkyl, such as —O—C(O)-alkyl, —C(O)—O-alkyl-, and -alkyl-C(O)—O-alkyl-. Exemplary esters also include aryl or heteroaryl esters, e.g. wherein at least one of R$_j$ or R$_k$ is a heteroaryl group such as pyridine, pyridazine, pyrmidine and pyrazine, such as a nicotinate ester. Exemplary esters also include reverse esters having the structure —R$_k$C(O)O—, where the oxygen is bound to the parent molecule. Exemplary reverse esters include succinate, D-argininate, L-argininate, L-lysinate and D-lysinate. Esters also include carboxylic acid anhydrides and acid halides.

The term "ether" refers to the structure —R$_l$—O—R$_m$—, where R$_l$ and R$_m$ can independently be alkyl, alkenyl, alkynyl, aryl, cycloalkyl, heterocyclyl, and ether. The ether can be attached to the parent molecular group through R$_l$ or R$_m$. Exemplary ethers include, but are not limited to, alkoxyalkyl and alkoxyaryl groups. Ethers also includes polyethers, e.g., where one or both of R$_l$ and R$_m$ are ethers.

The terms "halo" or "halogen" or "Hal" as used herein refer to F, Cl, Br, or I.

The term "haloalkyl" as used herein refers to an alkyl group substituted with one or more halogen atoms. "Haloalkyls" also encompass alkenyl or alkynyl groups substituted with one or more halogen atoms.

The term "heteroaryl" as used herein refers to a mono-, bi-, or multi-cyclic, aromatic ring system containing one or more heteroatoms, for example 1-3 heteroatoms, such as nitrogen, oxygen, and sulfur. Heteroaryls can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heteroaryls can also be fused to non-aromatic rings. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidilyl, tetrazolyl, furyl, thienyl, isoxazolyl, thiazolyl, furyl, phenyl, isoxazolyl, and oxazolyl. Exemplary heteroaryl groups include, but are not limited to, a monocyclic aromatic ring, wherein the ring comprises 2-5 carbon atoms and 1-3 heteroatoms, referred to herein as "($C_2$-$C_5$)heteroaryl."

The terms "heterocycle," "heterocyclyl," or "heterocyclic" as used herein refer to a saturated or unsaturated 3-, 4-, 5-, 6- or 7-membered ring containing one, two, or three heteroatoms independently selected from nitrogen, oxygen, and sulfur. Heterocycles can be aromatic (heteroaryls) or non-aromatic. Heterocycles can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heterocycles also include bicyclic, tricyclic, and tetracyclic groups in which any of the above heterocyclic rings is fused to one or two rings independently selected from aryls, cycloalkyls, and heterocycles. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetra hydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl.

The terms "hydroxy" and "hydroxyl" as used herein refers to —OH.

The term "hydroxyalkyl" as used herein refers to a hydroxy attached to an alkyl group.

The term "hydroxyaryl" as used herein refers to a hydroxy attached to an aryl group.

The term "ketone" as used herein refers to the structure —C(O)—Rn (such as acetyl, —C(O)$CH_3$ or —$R_n$_C(O)—$R_o$—. The ketone can be attached to another group through $R_n$ or $R_o$. $R_n$ or $R_o$ can be alkyl, alkenyl, alkynyl, cycloalkyl, heterocyclyl or aryl, or $R_n$ or $R_o$ can be joined to form a 3- to 12-membered ring.

The term "monoester" as used herein refers to an analogue of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic and maleic acid.

The term "nitro" as used herein refers to —$NO_2$.

The term "perfluoroalkoxy" as used herein refers to an alkoxy group in which all of the hydrogen atoms have been replaced by fluorine atoms.

The term "perfluoroalkyl" as used herein refers to an alkyl group in which all of the hydrogen atoms have been replaced by fluorine atoms. Exemplary perfluroalkyl groups include, but are not limited to, $C_1$-$C_5$ perfluoroalkyl, such as trifluoromethyl.

The term "perfluorocycloalkyl" as used herein refers to a cycloalkyl group in which all of the hydrogen atoms have been replaced by fluorine atoms.

The term "phenyl" as used herein refers to a 6-membered carbocyclic aromatic ring. The phenyl group can also be fused to a cyclohexane or cyclopentane ring. Phenyl can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone.

The term "phosphate" as used herein refers to the structure —OP(O)$O_2$—, —$R_x$OP(O)$O_2$—, —OP(O)$O_2R_y$—, or —$R_x$OP(O)$O_2R_y$—, wherein $R_x$ and $R_y$ can be alkyl, alkenyl, alkynyl, aryl, cycloalkyl, heterocyclyl, and hydrogen.

The term "sulfide" as used herein refers to the structure —$R_z$S—, where $R_z$ can be alkyl, alkenyl, alkynyl, aryl, arylalkyl, cycloalkyl, haloalkyl, heteroaryl, heterocyclyl. The sulfide may be cyclic, forming a 3 to 12-membered ring. The term "alkylsulfide" as used herein refers to an alkyl group attached to a sulfur atom.

The term "sulfinyl" as used herein refers to the structure —S(O)O—, —$R_p$S(O)O—, —$R_p$S(O)O$R_q$—, or —S(O)O$R_q$—, wherein $R_p$ and $R_q$ can be alkyl, alkenyl, aryl, arylalkyl, cycloalkyl, haloalkyl, heteroaryl, heterocyclyl, hydroxyl. Exemplary sulfinyl groups include, but are not limited to, alkylsulfinyls wherein at least one of $R_p$ or $R_q$ is alkyl, alkenyl, or alkynyl.

The term "sulfonamide" as used herein refers to the structure —($R_r$)—N—S(O)$_2$—$R_s$— or —$R_t$($R_r$)—N—S(O)$_2$—$R_s$, where $R_t$, $R_r$, and $R_s$ can be, for example, hydrogen, alkyl, alkenyl, alkynyl, aryl, cycloalkyl, and heterocyclyl. Exemplary sulfonamides include alkylsulfonamides (e.g., where $R_s$ is alkyl), arylsulfonamides (e.g., where $R_s$ is aryl), cycloalkyl sulfonamides (e.g., where $R_s$ is cycloalkyl), and heterocyclyl sulfonamides (e.g., where $R_s$ is heterocyclyl).

The term "sulfonate" as used herein refers to —$OSO_3$—. Sulfonate includes salts such as —$OSO_3$Na, —$OSO_3$K and the acid —$OSO_3$H.

The term "sulfonic acid" refers to —$SO_3$H— and its corresponding salts (e.g., —$SO_3$K— and —$SO_3$Na—).

The term "sulfonyl" as used herein refers to the structure $R_u$$SO_2$—, where $R_u$ can be alkyl, alkenyl, alkynyl, aryl, cycloalkyl, and heterocyclyl (e.g., alkylsulfonyl). The term "alkylsulfonyl" as used herein refers to an alkyl group attached to a sulfonyl group. "Alkylsulfonyl" groups can optionally contain alkenyl or alkynyl groups.

The term "thioketone" refers to the structure —$R_v$—C(S)—$R_w$—. The ketone can be attached to another group through $R_v$ or $R_w$. $R_v$ or $R_w$ can be alkyl, alkenyl, alkynyl, cycloalkyl, heterocyclyl or aryl, or $R_v$ or $R_w$ can be joined to form a 3- to 12-membered ring.

"Alkyl" groups can be substituted with or interrupted by or branched with at least one group selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, ketone, heteroaryl, heterocyclyl, hydroxyl, nitro, phosphate, sulfide, sulfinyl, sulfonyl, sulfonic acid, sulfonamide, thioketone, ureido and N. The substituents may be branched to form a substituted or unsubstituted heterocycle or cycloalkyl.

"Alkenyl," "alkynyl", "alkoxy", "amino" and "amide" groups can be substituted with or interrupted by or branched with at least one group selected from alkoxy, aryloxy, alkyl, alkenyl, alkynyl, amide, amino, aryl, arylalkyl, carbamate, carbonyl, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, thioketone, ureido and N. The substituents may be branched to form a substituted or unsubstituted heterocycle or cycloalkyl.

As used herein, a "suitable substituent" refers to a group that does not nullify the synthetic or pharmaceutical utility of the compounds of Formula I or Formula II. Examples of suitable substituents include, but are not limited to: $C_{1-22}$, $C_{1-8}$, and $C_{1-6}$ alkyl, alkenyl or alkynyl; $C_{1-6}$ aryl, $C_{2-5}$ heteroaryl; $C_{3-7}$ cycloalkyl; $C_{1-22}$, $C_{1-8}$, and $C_{1-6}$ alkoxy; $C_6$ aryloxy; —CN; —OH; oxo; halo, carboxy; amino, such as —NH($C_{1-22}$, $C_{1-8}$, or $C_{1-6}$ alkyl), —N($C_{1-22}$, $C_{1-8}$, and $C_{1-6}$ alkyl)$_2$, —NH(($C_6$)aryl), or —N(($C_6$)aryl)$_2$; formyl; ketones, such as —CO($C_{1-22}$, $C_{1-8}$, and $C_{1-6}$ alkyl), —CO (($C_6$ aryl) esters, such as —CO$_2$($C_{1-22}$, $C_{1-8}$, and $C_{1-6}$ alkyl) and —CO$_2$ ($C_6$ aryl). One of skill in art can readily choose a suitable substituent based on the stability and pharmacological and synthetic activity of the compound of the invention.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutically acceptable composition" as used herein refers to a composition comprising at least one compound as disclosed herein formulated together with one or more pharmaceutically acceptable carriers.

The term "pharmaceutically acceptable prodrugs" as used herein represents those prodrugs of the compounds of the present invention that are, within the scope of sound medical judgment, suitable for use in contact with the tissues of humans and lower animals without undue toxicity, irritation, allergic response, commensurate with a reasonable benefit/risk ratio, and effective for their intended use, as well as the zwitterionic forms, where possible, of the compounds of Formula I or Formula II. A discussion is provided in Higuchi et al., "Prodrugs as Novel Delivery Systems," *ACS Symposium Series*, Vol. 14, and in Roche, E. B., ed. *Bioreversible Carriers in Drug Design*, American Pharmaceutical Association and Pergamon Press, 1987, both of which are incorporated herein by reference.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

The compounds of Formula I and Formula II may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

Individual stereoisomers of compounds for use in the methods of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well-known asymmetric synthetic methods.

Geometric isomers can also exist in the compounds of Formula I and Formula II. The present invention encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the E and Z isomers.

Substituents around a carbon-carbon double bond alternatively can be referred to as "cis" or "trans," where "cis" represents substituents on the same side of the double bond and "trans" represents substituents on opposite sides of the double bond. The arrangements of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds of Formula I and Formula II disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

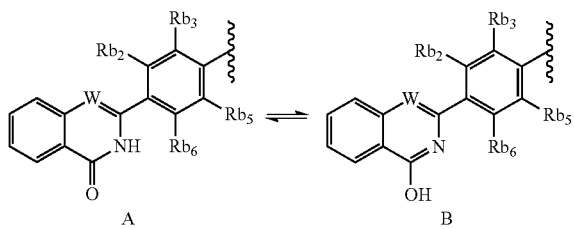

As used herein, "complement-associated disease", "complement-associated disorder" and "complement-associated condition" refers to diseases, disorders and conditions mediated by aberrant activity of one or more of the components of the complement cascade and its associated systems. Exemplary complement-associated diseases include, but are not limited to, atherosclerosis, membranous glomerulonephritis, asthma, organ transplantation rejection, thrombosis, deep vein thrombosis, disseminated venous thromboembolism, disseminated intravascular coagulation, and chronic obstructive pulmonary disease (COPD). Additional exemplary complement-associated diseases include, but are not limited to, paroxysmal nocturnal hemoglobinuria, atypical hemolytic uremic syndrome, amyotrophic lateral sclerosis, macular degeneration, lupus nephritis, myasthenia gravis, neuromyelitis optica, anti-phospholipid syndrome, catastrophic anti-phospholipid syndrome, dense deposit disease (type II membranoproliferative glomerulonephritis), Shiga-like toxin-producing E. coli hemolytic uremic syndrome, and abdominal and thoracic aortic aneurysms. Further exemplary complement-associated diseases include, but are not limited to, familial CD59 deficiency, cold agglutinin disease, familial C3 glomerulopathy, C3 glomerulonephritis, complement factor H related protein 5 nephropathy, IgA nephropathy, and hereditary angioedema (HAE).

"Subject" refers to an animal, such as a mammal, that has been or will be the object of treatment, observation, or experiment. The methods described herein may be useful for both human therapy and veterinary applications. In one embodiment, the subject is a human.

As used herein, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to reducing the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder. For example, treating a cholesterol disorder may comprise decreasing blood cholesterol levels.

As used herein, "prevention" or "preventing" refers to a reduction of the risk of acquiring a given disease or disorder or a symptom of a given disease or disorder.

As used herein, "modulate", "modulation" or "modulating" refers to a downregulation of expression of components of the complement cascade resulting in reduced activity of the complement pathway.

Pharmaceutical Compositions

In certain embodiments, the compound of Formula I or Formula II (or a tautomer, stereoisomer, pharmaceutically acceptable salt, or hydrate thereof) is formulated for oral administration. Formulations suitable for oral administration may be presented in discrete units, such as capsules, cachets, lozenges, tablets, or patches, each containing a predetermined amount of a compound of the present disclosure as powder or granules; as a solution or a suspension in an aqueous or non-aqueous liquid; or as an oil-in-water or water-in-oil emulsion. Such formulations may be prepared by any suitable method of pharmacy which includes the step of bringing into association at least one compound of the present disclosure as the active compound and a carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with at least one compound described herein as the active compound in a unit-dose formulation, for example, a tablet, which may contain from about 0.05% to about 95% by weight of the at least one active compound. Other pharmacologically active substances may also be present including other compounds. The formulations of the present disclosure may be prepared by any of the well-known techniques of pharmacy consisting essentially of admixing the components.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by, for example, dissolving or dispersing, at least one active compound of the present disclosure as described herein and optional pharmaceutical adjuvants in an excipient, such as, for example, water, saline, aqueous dextrose, glycerol, ethanol, and the like, to thereby form a solution, ointment, or suspension. In general, suitable formulations may be prepared by uniformly and intimately admixing at least one active compound of the present disclosure with a liquid or finely divided solid carrier, or both, and then, if necessary, shaping the product. For example, a tablet may be prepared by compressing or molding a powder or granules of at least one compound of the present disclosure, which may be optionally combined with one or more accessory ingredients.

Compressed tablets may be prepared by compressing, in a suitable machine, at least one compound of the present disclosure in a free-flowing form, such as a powder or granules, which may be optionally mixed with a binder, lubricant, inert diluent and/or surface active/dispersing agent(s). Molded tablets may be made by molding, in a suitable machine, where the powdered form of at least one compound of the present disclosure is moistened with an inert liquid diluent.

Formulations suitable for buccal (sub-lingual) administration include lozenges comprising at least one compound of the present disclosure in a flavored base, usually sucrose and acacia or tragacanth, and pastilles comprising the at least one compound in an inert base such as gelatin and glycerin or sucrose and acacia.

The amount of active compound administered may be dependent on the subject being treated, the subject's weight, the manner of administration and the judgment of the prescribing physician. For example, a dosing schedule may involve the daily or twice-daily administration of the encapsulated compound or compounds at a dosage of about 1-100 mg or 100-300 mg of a compound of Formula I or Formula II (or a stereoisomer, tautomer, pharmaceutically acceptable salt, or hydrate thereof).

In another embodiment, intermittent administration, such as on a monthly or yearly basis, of a dose of the encapsulated compound may be employed. Encapsulation facilitates access to the site of action and allows the administration of the active ingredients simultaneously, in theory producing a synergistic effect. In accordance with standard dosing regimens, physicians will readily determine optimum dosages and will be able to readily modify administration to achieve such dosages.

A therapeutically effective amount of a compound or composition disclosed herein can be measured by the therapeutic effectiveness of the compound. The dosages, however, may be varied depending upon the requirements of the patient, the severity of the condition being treated, and the compound being used. In one embodiment, the therapeutically effective amount of a disclosed compound is sufficient to establish a maximal plasma concentration. Preliminary doses as, for example, determined according to animal tests, and the scaling of dosages for human administration is performed according to art-accepted practices.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferable.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., *Cancer Chemother. Reports* 50(4):219-244 (1966) and Table 1 for Equivalent Surface Area Dosage Factors).

TABLE 1

Equivalent Surface Area Dosage Factors

| From: | To: | | | | |
|---|---|---|---|---|---|
| | Mouse (20 g) | Rat (150 g) | Monkey (3.5 kg) | Dog (8 kg) | Human (60 kg) |
| Mouse | 1 | 1/2 | 1/4 | 1/6 | 1/12 |
| Rat | 2 | 1 | 1/2 | 1/4 | 1/7 |
| Monkey | 4 | 2 | 1 | 3/5 | 1/3 |
| Dog | 6 | 4 | 3/5 | 1 | 1/2 |
| Human | 12 | 7 | 3 | 2 | 1 |

The dosage of such compounds lies preferably within a range of circulating concentrations that include the $ED_{50}$ with little or no toxicity. The dosage may vary within this range depending upon the dosage form employed and the route of administration utilized. Generally, a therapeutically effective amount may vary with the subject's age, condition, and gender, as well as the severity of the medical condition in the subject. The dosage may be determined by a physician and adjusted, as necessary, to suit observed effects of the treatment.

Methods of Treatment

The invention provides methods for modulating the complement system in a patient in need thereof. In some embodiments, the methods comprise treating or preventing complement-associated diseases or disorders by administering to a subject (e.g., a mammal, such as e.g., a human) a therapeutically effective amount of at least one compound of the invention, i.e., a compound of Formula I or Formula II, or a tautomer, stereoisomer, pharmaceutically acceptable salt, or hydrate thereof. In certain embodiments, the methods of the invention comprise administering a pharmaceutically acceptable composition, comprising one or more compounds of Formula I or Formula II and a pharmaceutically acceptable carrier.

The invention further provides a method for treating or preventing a complement-associated disease or disorder involving the modulation of one or more genes selected from, for example, Mannose-Binding Lectin (protein C) 2, complement component 9, complement component 6, complement component 8, alpha polypeptide, complement component 4B, complement component 4A, coagulation factor IX, Coagulation factor VII, complement component 4 binding protein-beta, complement component 5, Protein C, coagulation factor XI, kallikrein B, plasma, tissue factor pathway inhibitor, complement component 8, gamma polypeptide, complement component 1-s subcomponent, complement component 8-beta polypeptide, coagulation factor XII, coagulation factor II, coagulation factor XIII B polypeptide, serpin peptidase inhibitor clade E, complement component 2, alpha-2-macroglobulin, complement factor H, complement factor I, complement factor B, complement component 1 R subcomponent, mannan-binding lectin serine peptidase 1, protein S, coagulation factor V, complement component 5a receptor 1, complement component 4 binding protein alpha, serpin peptidase inhibitor clade C member 1, complement component 3, mannan-binding lectin serine peptidase 2, coagulation factor X, coagulation factor VIII, serpin peptidase inhibitor clade D member 1, serpin peptidase inhibitor clade F member 2, plasminogen, bradykinin receptor B2, bradykinin receptor B1, serpin peptidase inhibitor clade A member 5, coagulation factor III, serpin peptidase inhibitor, clade G (C1 inhibitor) member 1, carboxypeptidase B2 (Plasma), fibrinogen beta chain, kininogen 1, complement component (3b/4b) receptor 1, plasminogen activator tissue, complement component (3d/epstein barr virus) receptor 2, thrombomodulin, CD55 molecule, decay accelerating factor for complement, complement component 1 Q subcomponent A chain, or complement component 7, plasminogen activator urokinase, complement factor D, complement component 1 Q subcomponent C chain, CD46 molecule complement regulatory protein, fibrinogen gamma chain, von willebrand factor, CD59 molecule complement regulatory, plasminogen activator urokinase receptor, serpin peptidase inhibitor clade A member 1, coagulation factor XIII A1 polypeptide, complement component 3a receptor 1, fibrinogen alpha chain, complement component 1 Q subcomponent, B chain, and/or coagulation factor II (thrombin)

receptor, by administering a therapeutically effective amount of at least one compound of Formula I or Formula II or a stereoisomer, tautomer, pharmaceutically acceptable salt, or hydrate thereof.

Another embodiment comprises a method for treating or preventing a complement-associated disease or disorder involving the modulation of one or more genes selected from, Mannose-Binding Lectin (protein C) 2, complement component 3, complement component 5, complement factor D, complement factor H, and/or complement component 9.

In one embodiment, the method comprises administering at least one compound of Formula I or Formula II or a stereoisomer, tautomer, pharmaceutically acceptable salt, or hydrate thereof, to a subject, such as a human, as a preventative against complement-associated diseases and disorders, such as, for example, atherosclerosis, membranous glomerulonephritis, asthma, organ transplantation rejection, thrombosis, deep vein thrombosis, disseminated venous thromboembolism, disseminated intravascular coagulation, and chronic obstructive pulmonary disease (COPD).

In another embodiment, the method comprises administering at least one compound of Formula I or Formula II or a stereoisomer, tautomer, pharmaceutically acceptable salt, or hydrate thereof, to a subject, such as a human, as a preventative against complement-associated diseases and disorders, such as, for example, paroxysmal nocturnal hemoglobinuria, atypical hemolytic uremic syndrome, amyotrophic lateral sclerosis, macular degeneration, lupus nephritis, myasthenia gravis, neuromyelitis optica, anti-phospholipid syndrome, catastrophic anti-phospholipid syndrome, dense deposit disease (type II membranoproliferative glomerulonephritis), Shiga-like toxin-producing E. coli hemolytic uremic syndrome, and abdominal and thoracic aortic aneurysms.

In another embodiment, the method comprises administering at least one compound of Formula I or Formula II or a stereoisomer, tautomer, pharmaceutically acceptable salt, or hydrate thereof, to a subject, such as a human, as a preventative against complement-associated diseases and disorders, such as, for example, familial CD59 deficiency, cold agglutinin disease, familial C3 glomerulopathy, C3 glomerulonephritis, complement factor H related protein 5 nephropathy, IgA nephropathy, and hereditary angioedema (HAE).

In one embodiment, at least one compound of Formula I or Formula II or a stereoisomer, tautomer, pharmaceutically acceptable salt, or hydrate thereof, is administered as a preventative to a subject, such as a human, having a genetic predisposition to complement-associated diseases and disorders, such as, for example, atherosclerosis, membranous glomerulonephritis, asthma, organ transplantation rejection, thrombosis, deep vein thrombosis, disseminated venous thromboembolism, disseminated intravascular coagulation, and chronic obstructive pulmonary disease (COPD).

In another embodiment, at least one compound of Formula I or Formula II or a stereoisomer, tautomer, pharmaceutically acceptable salt, or hydrate thereof, is administered as a preventative measure to a subject, such as a human, having a genetic predisposition to complement-associated diseases and disorders, such as, for example, paroxysmal nocturnal hemoglobinuria, atypical hemolytic uremic syndrome, amyotrophic lateral sclerosis, macular degeneration, lupus nephritis, myasthenia gravis, neuromyelitis optica, anti-phospholipid syndrome, catastrophic anti-phospholipid syndrome, dense deposit disease (type II membranoproliferative glomerulonephritis), Shiga-like toxin-producing E. coli hemolytic uremic syndrome, and abdominal and thoracic aortic aneurysms.

In another embodiment, at least one compound of Formula I or Formula II or a stereoisomer, tautomer, pharmaceutically acceptable salt, or hydrate thereof, is administered as a preventative measure to a subject, such as a human, having a genetic predisposition to complement-associated diseases and disorders, such as, for example, familial CD59 deficiency, cold agglutinin disease, familial C3 glomerulopathy, C3 glomerulonephritis, complement factor H related protein 5 nephropathy, IgA nephropathy, and hereditary angioedema (HAE)

In another embodiment, the compounds of Formula I or Formula II may be used for the prevention of one complement-associated disease or disorder while concurrently treating another.

EXAMPLES

Example 1: Gene Expression Changes

In this example, mRNA levels from cultured cells were quantitated. The assay can be used to determine the effect of compound(s) on regulating mRNA levels, including those compounds in the present invention. Complement genes are expressed at high endogenous levels, but their expression can also be stimulated with various cytokines in inflammatory conditions. Experiments in this example target both basal and inflammatory complement gene expression. Compound mediated changes in gene expression and resulting mRNA levels are presented in Tables 2, 3 and 4 as well as FIGS. 1, 2, 3 and 4 below.

Huh-7 and HepG2 cells are liver-derived cell lines and are models for what can occur in the liver. Huh-7 cells (JCRB Cell Bank) were introduced to 96-well plates (~2.5×10$^5$ per well) in 100 μL DMEM containing 10% (v/v) FBS, 100 U/mL penicillin, 100 ug/mL streptomycin and 5 ug/mL plasmocin (all reagents from Gibco, except for the former, which was obtained from Invivogen). After 24 h, Huh-7 cells were treated with compounds in the same media formulation used for plating, and supplemented with 0.1% DMSO for the amount of time indicated in tables 2, 3, and 4. For select experiments, 24 h post-plating, cells were treated with cytokines and the compound of interest simultaneously, for a total treatment time of 48 h. Alternatively, 24 h after plating, cells were pre-treated with cytokines for 24 h before adding the compound of interest for 48 h. HepG2 cells (ATCC) were cultured in 96-well plates (~2.5×10$^5$ per well) in MEM containing 10% FBS, 1× non-essential amino acids, 1 mM sodium pyruvate, 2 mM L-glutamine, 100 U/mL penicillin, 100 ug/mL streptomycin and 5 ug/mL plasmocin. Serum amount was reduced to 0.5% for treatments with compound or cytokines. Timing of treatment of HepG2 cells with compounds and cytokines was as described for Huh-7 cells. Primary human hepatocytes (CellzDirect/Life Technologies) were plated in collagen coated 96-well plates at 70 000 cells/well, then overlaid with Matrigel™ as recommended by the supplier. Cells were treated with compounds of interest and/or cytokines for the indicated time points in the recommended media supplemented with 0.1% DMSO and 10% FBS (v/v). Cells were harvested by mRNA Catcher PLUS Kit (Life Technologies) followed by real-time PCR using the RNA UltraSense One-Step qRT-PCR System. The level of the mRNA of interest was measured by TaqMan real-time PCR relative to the endogenous control cyclophilin A in the same sample. Data were acquired using the ViiA-7 Real Time PCR System (Applied Biosystems).

Downregulation of expression of components of the complement cascade will result in reduced activity of the pathway and thus will constitute a positive result. Tables 2 and 3 list the concentration of compounds at which the level of the indicated mRNA is reduced by 50%, as well as the duration of treatment with compound. Table 4 lists the maximum reduction in the indicated mRNA measured in primary human hepatocytes treated with compounds for up to 72 hours. FIGS. 1, 2, 3 and 4 show effects of compounds on cytokine-induced (i.e. inflammatory) expression of complement genes in Huh-7 cells and HepG2 cells.

In addition to genes shown in Tables 2 and 4, other members of the complement and coagulation cascades are assayed via real-time PCR in cultured cells such as, but not limited to, Huh-7, HepG2 and/or primary human hepatocytes.

TABLE 2

Suppression of complement gene expression in human hepatoma cells. Data are presented as half maximal inhibitory concentrations (IC50) of compounds in micromolar (uM).

|  | RVX000222 | | JQ1 | | RVX000297 | RVX002109 | RVX002135 |
|---|---|---|---|---|---|---|---|
| Complement gene | Huh-7 | HepG2 | Huh-7 | HepG2 | | Huh-7 | |
| C3 (48 h) | 1.90 | — | 0.20 | 0.20 | 4.70 | 34.8 | 2.20 |
| C4a/C4b (48 h) | 6.30 | — | — | — | 4.50 | 62.2 | 4.30 |
| C5 (48 h) | >30 | — | — | — | >10 | >50 | 37.9 |
| C3 (72 h) | — | 25.0 | — | 0.49 | — | — | — |
| MBL2 (48 h) | 16.3 | 3.88 | 0.16 | 0.03 | — | — | — |
| C1S (48 h) | 18.9 | 9.56 | 0.3 | 0.12 | — | — | — |
| C4a/C4b (72 h) | 5.40 | 10.0 | 0.07 | 0.25 | — | — | — |
| C5 (72 h) | 21.8 | 20.0 | 0.27 | 0.46 | — | — | — |

TABLE 3

Suppression of C3 and C4 expression in Huh-7 cells after a 48 h treatment with listed compounds. Data are presented as half maximal inhibitory concentrations (IC50) of compounds in micromolar (uM).

| | mRNA expression in Huh-7 cells: $IC_{50}$ (uM) | |
|---|---|---|
| Compound | C3 | C4 |
| RVX000206 | 3.6 | 9.3 |
| RVX000255 | 20.4 | 17.4 |
| RVX000344 | 11.6 | 15.6 |
| RVX000641 | 12.6 | 9.3 |
| RVX000662 | 29.2 | 21.1 |
| RVX000668 | 9.5 | 15.6 |
| RVX000843 | 11.1 | >50 uM |
| RVX002093 | 18.5 | 17.2 |
| RVX002101 | 11.3 | 22.0 |
| RVX002103 | 13.9 | 13.8 |
| RVX002113 | 5.8 | 7.8 |
| RVX002141 | 15.4 | 17.8 |
| JQ1 | 0.18 | 0.065 |

TABLE 4

Downregulation of expression of complement components in primary human hepatocytes from a single donor. mRNA levels were determined at 6, 24, 48, and 72 hours of compound treatment. Values show the percent maximal reduction in gene expression and the associated treatment period (hours). Over this time course, maximum reduction in complement C3, complement C5, and MBL2 mRNA abundance was observed at 24 hours of treatment, and at 72 hours of treatment for complement C1S and complement C2 mRNA levels. Maximum reduction in complement C4 mRNA was observed at 24 hours of treatment with JQ1, versus 72 hours of RVX000222 treatment. Maximum reduction in complement C9 mRNA was found with 48 hours of treatment with JQ1 and 72 hours with RVX000222. Differences in treatment period required for maximum reduction in mRNA levels may be related to mRNA half-life or sensitivity of a particular gene to BET inhibition.

| Treatment | C3 | C4 | C5 | C9 | MBL2 | C1S | C2 |
|---|---|---|---|---|---|---|---|
| 30 uM RVX000222 | 13% (24 h) | 44% (72 h) | 38% (24 h) | 86% (72 h) | 92% (24 h) | 27% (72 h) | 35% (72 h) |
| 0.3 uM JQ1 | 54% (24 h) | 31% (24 h) | 67% (24 h) | 72% (48 h) | 93% (24 h) | 22% (72 h) | 29% (72 h) |

Example 2: In Vivo Studies Using Mouse Models

In this example, chimeric mice with humanized livers were generated by transplanting human hepatocytes into urokinase-type plasminogen activator$^{+/+}$/severe combined immunodeficient transgenic mice. Replacement with human hepatocytes can reach 80-90%. This mouse model can be used to determine the effect of compounds, including those compounds in the present invention, on regulating mRNA levels in human hepatocytes in vivo. Mice were treated with 150 mg/kg b.i.d. with RVX000222 or vehicle by oral gavage for 3 days. Livers were harvested and RNA levels determined by real-time PCR using human specific TaqMan primer probes and cyclophilin A as an endogenous control. Table 5 lists the reduction in the levels of the indicated mRNAs. *$p<0.05$, **$p<0.01$ versus vehicle treated animals using 2-tailed student's t-tests.

TABLE 5

RVX000222 reduces mRNA expression levels of complement components 3 (C3), 4 (C4) and 5 (C5) and mannose-binding lectin 2 (MBL2) in humanized livers of chimeric mice treated with 150 mg/kg b.i.d. for 3 days. Numbers represent average % reduction in expression relative to vehicle treated mice (3 mice per group).

| Compound | C3 | C4 | C5 | C9 | MBL2 |
|---|---|---|---|---|---|
| RVX000222 | 20% | 36%* | 17% | 45%** | 61%** |

Asterisk indicates $p < 0.05$; two asterisks indicate $p < 0.01$.

Example 3: Microarray Analysis in Whole Blood

In this example, RNA from human whole blood treated ex vivo was analyzed by microarray. The method can be used to determine the effect of compounds, including those in the present invention, on RNA levels (Table 6).

After obtaining informed consent, whole blood was collected from three healthy volunteers into BD Vacutainer Sodium Heparin tubes and samples were inverted 10 times. Blood samples (1 mL) were combined with 1 mL of RPMI containing 2 mM glutamine, 100 U/mL penicillin, 100 ug/mL streptomycin, 20% FBS and the compound of interest or vehicle (0.1% DMSO), followed by a 24 h incubation at 37° C. Treated samples were transferred to a PAXgene RNA tube (PreAnalytix/Qiagen), inverted 5 times and frozen. RNA was isolated with the PAXgene RNA kit according to manufacturer's instructions. Microarray analysis was performed by Asuragen (Austin, Tex.) using the Affymetrix Human U133 Plus 2.4 Array. Shown in Table 6 is the mean of 3 independent samples ($p<0.01$). Downregulation of expression of components of the complement cascade will result in reduced activity of the pathway and thus will constitute a positive result. Upregulation of negative regulators or downregulation of positive regulators of the pathway will also result in reduced activity of the pathway and thus will constitute a positive result.

TABLE 6

20 uM RVX000222 alters complement component 3, CD55 and CD59 mRNA levels in ex-vivo treated human blood.

| Gene | % change in expression |
|---|---|
| Complement component 3 (C3) | −59% |
| CD55 | 58% |
| CD59 | 88% |

Example 4: Measure of Secreted Complement Proteins

In this example, protein secretion from cells grown in culture in the presence of compound of interest was analyzed by enzyme linked immunosorbent assay (ELISA). In some cases, cultured cells were treated with cytokines and the compound of interest to mimic an inflammatory state. The method can be used to determine the effect of compounds, including those in the present invention, on the secretion of specific proteins from cells grown in culture under basal and cytokine stimulated (i.e. inflammatory) conditions (Table 7, FIGS. 5 and 6).

Huh-7 cells (JCRB Cell Bank) were introduced to 24-well plates in 500 μL DMEM supplemented with 10% (v/v) FBS, 100 U/mL penicillin, 100 ug/mL streptomycin and 5 ug/mL plasmocin (all reagents from Gibco, except for the former, which comes from Invivogen) at 200 000 cells/well. After 24 h, cells were treated with the compound of interest and/or cytokines in DMEM with 10% FBS containing 0.1% DMSO for a total treatment time of 72 h. Fresh media containing compounds and/or cytokines was introduced in the final 24 h of the experiment. At harvest, media were collected, debris was removed by brief centrifugation, and ELISA assays for the indicated proteins were performed as per the manufacturer's protocol. To correct for differences in cell numbers, values obtained for complement proteins were normalized to values for transferrin. HepG2 cells (ATCC) were cultured in MEM containing 10% FBS, 1× non-essential amino acids, 1 mM sodium pyruvate, 2 mM L-glutamine, 100 U/mL penicillin, 100 ug/mL streptomycin and 5 ug/mL plasmocin. Serum amount was reduced to 0.5% when compounds were present. Treatment combinations and timing were as described above for Huh-7 cells. Primary human hepatocytes (CellzDirect/Life Technologies) were plated in collagen coated 96-well plates at 70 000 cells/well, then overlaid with Matrigel™ as recommended by the supplier. Cells were treated with compounds of interest with or without the indicated cytokines for a total of 72 h in the recommended media supplemented with 10% FBS and 0.1% DMSO (v/v). Media were collected for measurements of secreted proteins.

Figure 5:
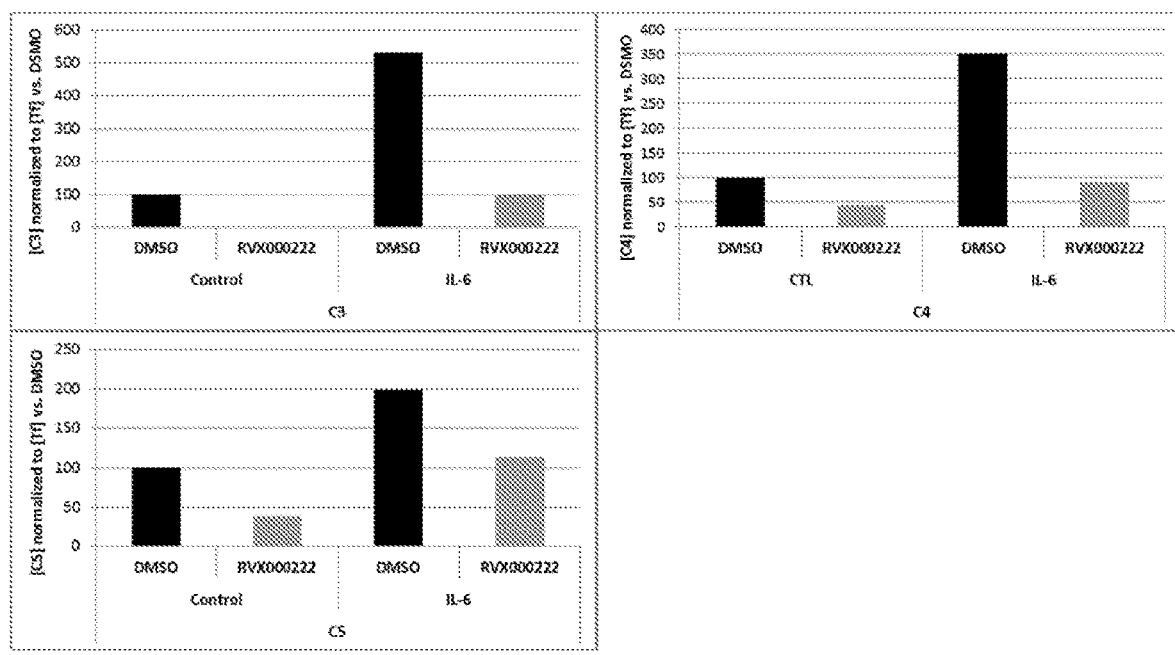
FIG. 5 demonstrates that 30 uM RVX000222 reduces secretion of C3, C4, and C5 proteins by Huh-7 cells treated simultaneously with interleukin 6 (IL-6). IL-6 induces complement expression during inflammation. Protein levels were quantitated by ELISA. Data is the mean of duplicate samples.
Figure 6:
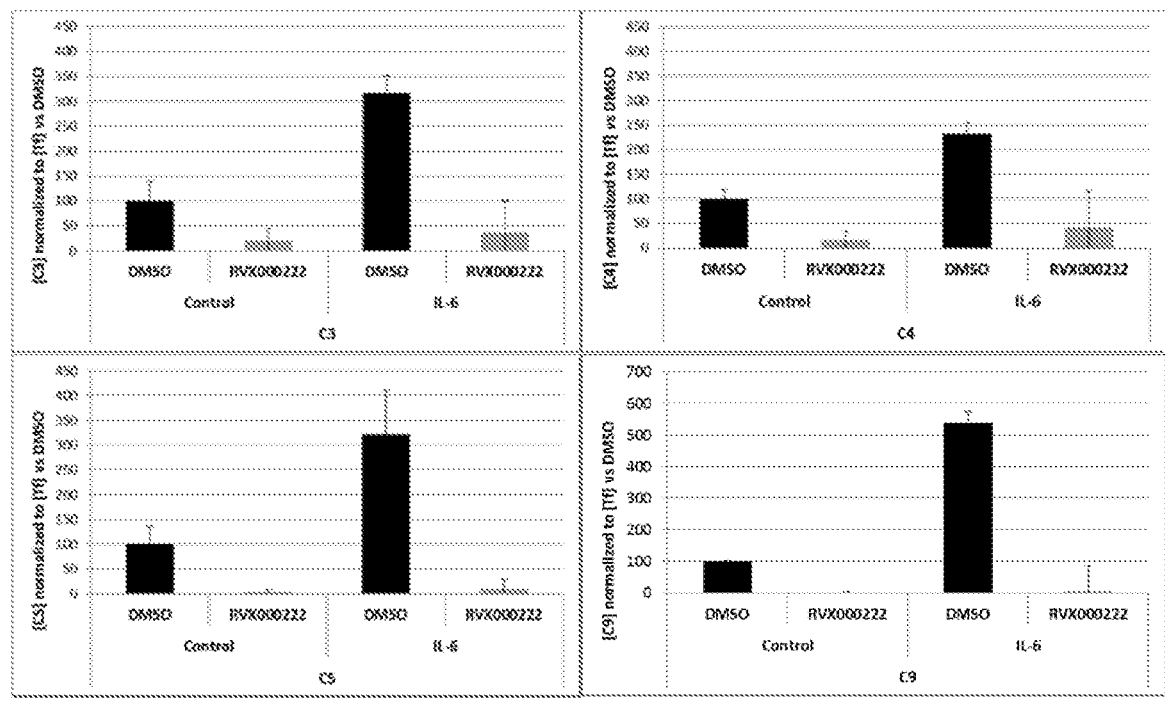
FIG. 6: demonstrated that 30 uM RVX000222 reduces secretion of C3, C4, C5 and C9 proteins by primary human hepatocytes treated simultaneously with interleukin 6 (IL-6). IL-6 induces complement expression during inflammation. Protein levels were quantitated by ELISA. Data is the mean of duplicate samples.

The ELISA kits for detection of complement C3, C4, C5 and C9 were obtained from AssayPro (St. Charles, Mo.), while the ELISA reagents for transferrin detection were from Bethyl Laboratories (Montgomery, Tex.). Data were collected on a Thermo Scientific Multiskan GO apparatus. Downregulation of expression of components of the complement cascade will result in reduced activity of the pathway and thus will constitute a positive result. Table 7: FIGS. 5 and 6 list the amount of C3, C4, C5 and C9 protein that are detected in the media of cells treated with RVX000222 (compared to DMSO).

Quantitation of additional secreted proteins from cultured cells using the ELISA method is being evaluated. This includes, but is not limited to, complement C6, C8, MBL2 or Factor H.

TABLE 7

Secretion of complement C3, C4, and C5 in Huh-7 and HepG2 cells.
Data are the percent maximum reduction in protein levels with
standard deviation derived from three independent experiments.

| Treatment | C3 | | C4 | | C5 | |
| --- | --- | --- | --- | --- | --- | --- |
| | Huh-7 | HepG2 | Huh-7 | HepG2 | Huh-7 | HepG2 |
| 30 uM RVX000222 | 87 ± 9% | 34 ± 5% | 79 ± 3% | 65 ± 5% | 53 ± 7% | 77 ± 4% |
| 0.75 uM JQ1 | 99 ± 1% | 54 ± 5% | 81 ± 6% | 81 ± 9% | 50 ± 13% | 82 ± 7% |

Example 5: Multi-Analyte Profiling

In this example, plasma samples from human subjects treated with placebo or RVX000222 was analyzed by Multi-Analyte Profiling (MAP) technology. The method can be used to determine the effect of compounds, including those in the present invention, on the levels of various analytes in plasma (Table 8).

Plasma collected from twenty RVX000222 treated subjects and ten placebo treated subjects at baseline and terminal time points (26 weeks) (from the previously completed ASSURE clinical trial; NCT01067820, was sent for MAP analysis. Using microsphere-based immuno-multiplexing, each sample was analyzed and the level of 107 different plasma proteins quantitated. The changes in values for each protein analyte were calculated versus the baseline measure, and statistically significant ($p<0.05$) and trending ($0.01>p>0.05$) values reported. Downregulation of expression of components of the complement cascade will result in reduced activity of the pathway and thus will constitute a positive result. Table 8 summarizes changes in plasma analytes observed with 26 week treatment with RVX000222.

TABLE 8

Changes in plasma analytes from the ASSURE trial (NCT01067820) measured
using multi-analyte profiling (week 26 vs. baseline $p < 0.05$)

| Analyte | N | Baseline | Units | Change from baseline | Percent Change from baseline | P-value vs baseline |
| --- | --- | --- | --- | --- | --- | --- |
| Complement Factor H (CFH) | 20 | 570.3 | ug/mL | −75.35 | −11.45 | 0.01 |
| Complement Factor H - Related Protein 1 (CFHR1) | 17 | 2353.5 | ug/mL | −291.76 | −10.75 | 0.003 |
| Complement C3 (C3) | 20 | 1.1 | mg/mL | −0.1 | −9.28 | 0.002 |

Example 6: Protein Quantitation Using LC-MRM/MS

In this example, plasma samples from human subjects treated with placebo or RVX000222 were analyzed by 1D LC-MRM/MS technology. The method can be used to determine the effect of compounds, including those in the present invention, on the levels of various analytes found in plasma.

Plasma collected from 74 RVX000222 treated subjects and 17 placebo treated subjects at baseline and terminal time points (26 weeks) (from the previously completed ASSURE clinical trial; NCT01067820) was sent for absolute protein quantification. Using mass spectrometric methods, including multiple reaction monitoring (MRM) mass spectrometry (MRM-MS), each sample is analyzed for the presence and amount of 43 different plasma proteins. The changes in values for each protein analyte are calculated versus the baseline measure, and statistically significant ($p<0.05$) and trending ($0.10>p>0.05$) values are reported (Table 9). Downregulation of expression of components of the complement cascade will result in reduced activity of the pathway and thus will constitute a positive result.

TABLE 9

Changes in plasma analytes from the ASSURE trial (NCT01067820)
measured using LC-MRM/MS (week 26 vs. baseline $p < 0.10$)

| Protein Peptide | Baseline (ng/mL) | Change from baseline (ng/mL) | Percent Change from baseline | P-value vs baseline |
| --- | --- | --- | --- | --- |
| Complement component C9 | 37,592 | −5,034 | −13.8 | 0.0001 |
| Complement component C8 alpha chain | *1,828* | *−120* | *−8.6* | 0.0001 |
| Complement C5 | 34,391 | −2,228 | −5.3 | 0.0001 |
| Complement factor 1 | 17,911 | −1,205 | −5.2 | 0.002 |
| Complement C4-B | 159,041 | −7,492 | −4.3 | 0.001 |
| Complement factor H | *206,226* | *−8,710* | *−4.2* | 0.0001 |
| Complement component C8 beta chain | 5,907 | −341 | −3.9 | 0.004 |
| Complement C3 | 769,753 | −34,105 | −3.6 | 0.02 |

TABLE 9-continued

Changes in plasma analytes from the ASSURE trial (NCT01067820)
measured using LC-MRM/MS (week 26 vs. baseline $p < 0.10$)

| Protein Peptide | Baseline (ng/mL) | Change from baseline (ng/mL) | Percent Change from baseline | P-value vs baseline |
| --- | --- | --- | --- | --- |
| Complement C1r subcomponent | 122,295 | −571 | −3.6 | 0.02 |
| Complement factor B | *131,959* | *−4,259* | *−4.2* | 0.06 |

Note:
Results are shown for peptide with highest concentration; italics indicate median

Example 7: Complement Activity Assays

In this example, serum samples from human subjects treated with placebo or RVX000222 were analyzed by the total hemolytic complement (CH50) assay and the complement alternative pathway (AH50) assay. The method can be used to determine the effect of compounds, including those in the present invention, on the activity of the classical and alternative complement system in clinical samples.

Figure 7A:
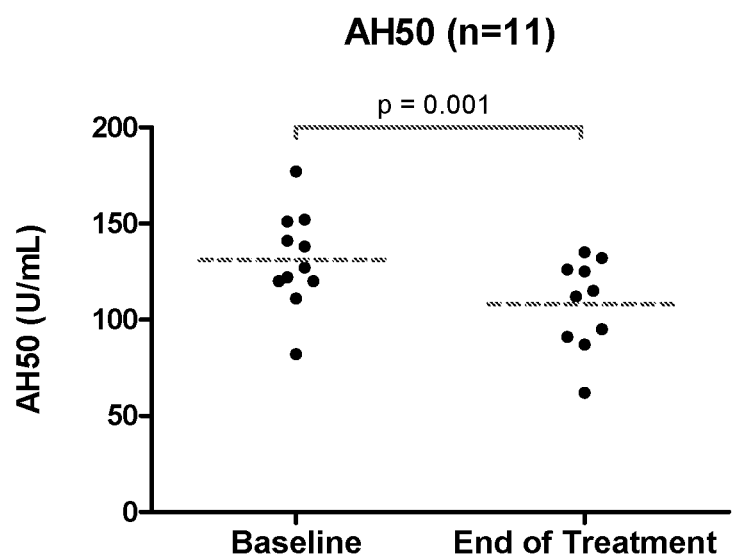
FIG. 7A: RVX000222 reduces complement activity in clinical samples as measured by AH50 assay.
Figure 7B:
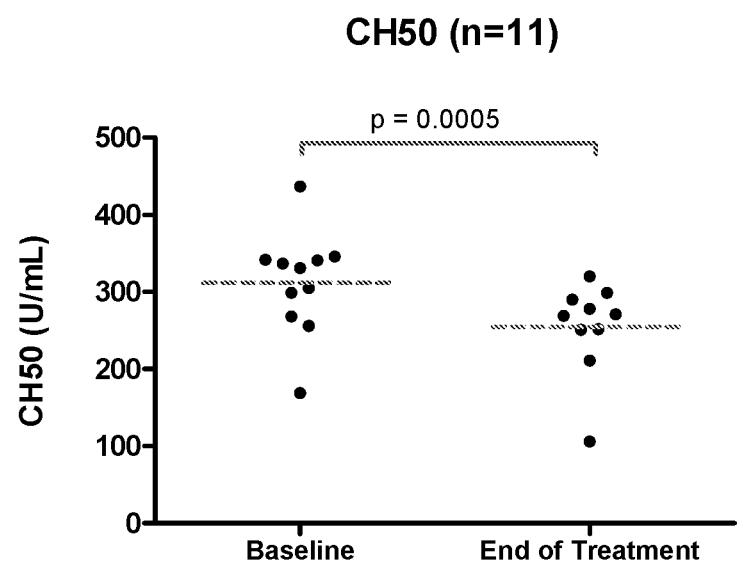
FIG. 7B: RVX000222 reduces complement activity in clinical samples as measured by CH50 assay.

Serum collected from RVX000222 treated subjects and placebo treated subjects at baseline and terminal time points (26 weeks) (from the previously completed ASSURE clinical trial; NCT01067820), was analyzed in the AH50 and CH50 assays. Using the CH50 screening assay to detect the hemolysis of sheep erythrocytes sensitized by specific antibodies, the hemolytic activity of the complement system in serum samples from treated and untreated subjects was measured. Likewise, using specific conditions to activate only the alternative pathway (AH50), activity of the complement response was measured. The degree of complement activation was measured at baseline and terminally to determine if there were any changes in the function of the complement system following drug treatment (FIG. 7). Reduced function of the complement system constitutes a positive result.

Example 8: Protein Quantitation in Clinical Samples Using SOMAScan™

In this example, plasma samples from human subjects treated with placebo or RVX000222 are analyzed by the SOMAscan™ assay (SomaLogic). The method can be used to determine the effect of compounds, including those in the present invention, on the abundance of proteins, including complement components, in clinical samples.

Plasma collected from 47 RVX000222 treated subjects at baseline and terminal time points (26 weeks) (from the previously completed ASSURE clinical trial; NCT01067820) was sent for analysis. Using the SOMAscan™ technology, each sample is analyzed for the relative presence and amount of 1,310 different proteins. The changes in values for each protein analyte are calculated versus the baseline measure, and statistically significant ($p<0.05$) values are reported (Table 10). Downregulation of expression of components of the complement cascade will result in reduced activity of the pathway and thus will constitute a positive result.

TABLE 10

Changes in serum analytes from the ASSURE trial measured using SOMAscan ™ (week 26 vs. baseline $p < 0.05$).

| | | RVX-208 at 200 mg/day | |
|---|---|---|---|
| Protein Name | Gene Symbol | % change vs. baseline | p-value vs baseline |
| Complement C3b | C3 | −52.7 | 0.001 |
| C-reactive protein | CRP | −43.6 | 0.0001 |

TABLE 10-continued

Changes in serum analytes from the ASSURE trial measured using SOMAscan ™ (week 26 vs. baseline $p < 0.05$).

| | | RVX-208 at 200 mg/day | |
|---|---|---|---|
| Protein Name | Gene Symbol | % change vs. baseline | p-value vs baseline |
| C5a anaphylatoxin | C5 | −28.7 | 0.0002 |
| Complement component C9 | C9 | −18.3 | 0.0001 |
| Mannose-binding protein C | MBL2 | −14.6 | 0.0002 |
| Complement component C6 | C6 | −14.3 | 0.0001 |
| Complement C5b-C6 complex | C5 C6 | −12.0 | 0.0001 |
| Complement C5 | C5 | −11.7 | 0.0001 |
| Complement component C8 | C8 | −10.1 | 0.004 |
| Complement factor B | CFB | −6.8 | 0.001 |
| Complement C2 | C2 | −6.7 | 0.001 |
| Complement factor I | CFI | −6.4 | 0.01 |
| Complement C1s subcomponent | C1S | −6.1 | 0.02 |
| Complement factor H | CFH | −5.6 | 0.0001 |
| Complement decay-accelerating factor | CD55 | −4.0 | 0.02 |
| Mannan-binding lectin serine protease 1 | MASP1 | 4.8 | 0.04 |

All references referred to herein are incorporated by reference in their entirety. Other embodiments of the invention will be apparent to those skilled in the art from consideration of the specification and practice of the invention disclosed herein.

What is claimed is:

1. A compound selected from:

2-{4-[2-(3,3-difluoropyrrolidin-1-yl)ethoxy]-3,5-dimethylphenyl}-5,7-dimethoxy-3,4-dihydroquinazolin-4-one;

methyl N-{2-[4-(5,7-dimethoxy-4-oxo-3,4-dihydroquinazolin-2-yl)-2,6-dimethylphenoxy]ethyl}carbamate;

and stereoisomers, tautomers, pharmaceutically acceptable salts, and hydrates thereof.

2. The compound of claim 1, wherein the compound is 2-{4-[2-(3,3-difluoropyrrolidin-1-yl)ethoxy]-3,5-dimethylphenyl}-5,7-dimethoxy-3,4-dihydroquinazolin-4-one.

3. The compound of claim 1, wherein the compound is methyl N-{2-[4-(5,7-dimethoxy-4-oxo-3,4-dihydroquinazolin-2-yl)-2,6-dimethylphenoxy]ethyl}carbamate.

4. A pharmaceutical composition comprising the compound of claim 1 and a pharmaceutically acceptable carrier.

5. A pharmaceutical composition comprising the compound of claim 2 and a pharmaceutically acceptable carrier.

6. A pharmaceutical composition comprising the compound of claim 3 and a pharmaceutically acceptable carrier.

\* \* \* \* \*